(12) United States Patent
Becker et al.

(10) Patent No.: US 9,187,448 B2
(45) Date of Patent: Nov. 17, 2015

(54) FLAVONOID COMPOUNDS

(75) Inventors: Cyrus K. Becker, Sunnyvale, CA (US);
George F. Schreiner, Sunnyvale, CA (US);
Sundeep Dugar, Sunnyvale, CA (US);
Dinesh Mahajan, Sunnyvale, CA (US)

(73) Assignee: CARDERO THERAPEUTICS, INC., Sunnyvale, CA (US)

( * ) Notice: Subject to any disclaimer, the term of this patent is extended or adjusted under 35 U.S.C. 154(b) by 0 days.

(21) Appl. No.: 14/237,167

(22) PCT Filed: Aug. 6, 2012

(86) PCT No.: PCT/US2012/049767
§ 371 (c)(1),
(2), (4) Date: May 23, 2014

(87) PCT Pub. No.: WO2013/022846
PCT Pub. Date: Feb. 14, 2013

(65) Prior Publication Data
US 2014/0256741 A1    Sep. 11, 2014

Related U.S. Application Data

(60) Provisional application No. 61/515,631, filed on Aug. 5, 2011.

(51) Int. Cl.
*C07D 311/62*    (2006.01)
*C07D 405/10*    (2006.01)
*A61K 31/353*    (2006.01)
*A61K 31/496*    (2006.01)

(52) U.S. Cl.
CPC ............ *C07D 311/62* (2013.01); *A61K 31/353* (2013.01); *A61K 31/496* (2013.01); *C07D 405/10* (2013.01)

(58) Field of Classification Search
USPC .............. 514/254.11, 456; 435/375; 549/399; 544/376
See application file for complete search history.

(56) References Cited

FOREIGN PATENT DOCUMENTS

WO    WO 2010121232 A1 * 10/2010 ............. A01N 43/16

* cited by examiner

*Primary Examiner* — Kristin Vajda
(74) *Attorney, Agent, or Firm* — Foley & Lardner LLP

(57) ABSTRACT

The present invention relates to compounds, compositions, and methods for treatment of conditions related to mitochondrial function. In various aspects, the present invention comprises administering one or more epicatechin derivatives in an amount effective to stimulate mitochondrial function in cells. The compounds, compositions, and methods described herein provide for reducing infarct size in the heart following permanent ischemia or ischemia/reperfusion event or method for delaying, attenuating or preventing adverse cardiac remodeling, and can assist in prevention of impaired mitochondria biogenesis and thus prevention of the consequences of impaired mitochondrial biogenesis in various diseases and conditions, as well as provide for the active therapy of mitochondrial depletion that may have already occurred.

3 Claims, 2 Drawing Sheets

FLAVONOID COMPOUNDS

CROSS-REFERENCE TO RELATED APPLICATIONS

This application is the National Phase of International Patent Application No. PCT/US2012/049767, filed Aug. 6, 2012, published as WO 2013-022846, which claims priority to U.S. Provisional Patent Application No. 61,515,631, filed Aug. 5, 2011, the contents of which is herein incorporated by reference in its entirety.

Disclosed herein are new flavonoid compounds and compositions and their application as pharmaceuticals for the treatment of disease. Methods of modulation of mitochondrial activity in a human or animal subject are also provided for the treatment diseases such as ischemia/reperfusion, myocardial infarction, acute ischemic renal injury, a disease of the aorta and its branches, ischemic injury arising from a medical intervention, acute ischemia, acute angina, acute kidney injury, total coronary occlusion, acute stroke, atrial fibrillation, temporary acute ischemia, CABG surgery, cardiac surgery involving cardiopulmonary bypass, aneurysm repair, angioplasty, administration of a radiocontrast agent, an inborn error of mitochondrial biogenesis or bioenergetics, a dietary deficiency, a vitamin deficiency, diabetes, metabolic syndrome, Friedreich's ataxia, pulmonary hypertension, chronic kidney disease (particularly that associated with glomerular epithelial injury or tubulointerstitial fibrosis, including diabetic nephropathy, focal segmental glomerulosclerosis, and chronic renal insufficiency), acute kidney injury (whether due to vascular insufficiency, drug effects, toxins, medical or surgical procedures, or otherwise), hypertension, dementia, heart failure, obesity, hyperlipidemia, insulin resistance, a muscular condition involving decreased mitochondrial function, impaired cognition related to aging, vascular disease, metabolic impairment or neurodegeneration, a neurological condition involving decreased mitochondrial function, myopathy, diabetes, weight gain, impaired cognition, loss of energy, fatigue, cardiovascular toxicity, hepatic toxicity, renal toxicity, and increased serum lipids.

Catechins are polyphenolic antioxidant found in plants and include, for example, monomeric flavan-3-ols catechin, epicatechin, gallocatechin, epigallocatechin, and epicatechin 3-O-gallate. Catechins are flavonoids and, to be more specific, flavan-3-ols. Catechin and epicatechin are epimers, with (−)-epicatechin and (+)-catechin being the most common optical isomers found in nature. Catechins constitute about 25% of the dry weight of fresh tea leaves although total the content varies widely depending on tea variety and growth conditions, and are also found in grapes and chocolate.

The bioavailability of (−)-epicatechin is controlled by a number of factors including metabolism, active transport, and binding to the food matrix. These factors combine to result in very low plasma levels of parent (−)-epicatechin. The major metabolic pathways in rat include glucuronidation by uridine 5'-diphosphate glucosyltransferase in the gut wall, followed by sulfation by phenolsulfotransferase in the liver, and O-methylation by catechol-O-methyltransferase in the liver and kidneys. (J. Nutr. 2001, 131, 2885-2891).

(−)-Epicatechin is absorbed from the small intestine by both passive and facilitated diffusion. (Ann. Nutr. Metab. 2006, 50, 59-65). These transport systems may include the mammalian bilirubin transporter bilitranslocase and chylomicron mediated transport. It is suggested that absorption of (−)-epicatechin is inhibited by (+)-catechin in rat. (J. Nutr. 2001, 131, 2885-2891). In a study of enterocyte absorption using human intestinal Caco-2 cells, (−)-epicatechin was found to be a substrate of the MRP2 efflux transporter. Inhibition of MRP2 with MK-571 increased absorption of (−)-epicatechin somewhat. In humans, (−)-epicatechin (ingested in chocolate) is approximately 30% absorbed and excreted as metabolites within hours. (Free Radic. Res. 2000, 33, 5, 635-641).

WO 2010/121232, which is hereby incorporated by reference in its entirety, describes the use of catechins for the treatment of conditions related to ischemic organ injury, and the related condition of ischemia/reperfusion injury. Such injuries are accompanied by changes in signaling molecules and metabolic effectors that can, independently or in concert, trigger cell death in its various forms. These include changes in intracellular pH, calcium, ceramide, free radicals, hypoxia and adenosine triphosphate (ATP) depletion. While all of these factors may be significantly altered as a consequence of acute necrotic cell death, they can also be specific effectors of apoptotic death under certain circumstances.

The contributions of apoptotic cell death and cellular necrosis to functional deterioration of the organ in ischemic conditions such as myocardial infarction and stroke are well established. Myocardial infarctions generally result in an immediate depression in ventricular function due to myocardial cell necrosis and apoptosis. These infarctions are also likely to expand, provoking a cascading sequence of myocellular and structural events which ultimately result in adverse cardiac remodeling. In many cases, this progressive myocardial infarct expansion and adverse ventricular remodeling (thinning of left ventricular wall, scar tissue formation) leads to deterioration in ventricular function and heart failure.

U.S. Provisional Application No. 61/493,932, which is hereby incorporated by reference in its entirety, describes the use of catechins for the treatment of conditions related to mitochondrial function. This term refers to those disorders that in one way or another result from or in failure of the mitochondria, specialized compartments present in cells that are responsible for creating more than 90% of the energy needed by the body to sustain life and support growth. When mitochondrial function fails, less energy is generated within the cell. Cell injury and ultimately cell death follow. Such conditions include those that have neuromuscular disease symptoms (often referred to as "mitochondrial myopathy"), diabetes mellitus, multiple sclerosis, subacute sclerosing encephalopathy, dementia, myoneurogenic gastrointestinal encephalopathy, Parkinson's disease, Huntington disease, Amyotrophic Lateral Sclerosis (ALS), mental retardation, deafness and blindness, obesity, hyperlipidemia, heart failure, stroke, lupus, ocular conditions such as age-related macular degeneration (AMD), and rheumatoid arthritis. Such conditions also include the relative ability to exercise. This includes, for example, recovery from immobilization of a body part or simply improving general exercise capacity.

In addition, a number of drug classes have recently been identified as inducing organ degeneration or other side effects which are mediated by their effects on mitochondrial bioenergetics. The most frequent targets in drug-induced mitochondrial dysfunction are the heart, liver and kidneys, although other organs can also be affected. U.S. Provisional Application No. 61/493,932 also describes the use of catechins in the treatment of such drug-induced effects.

There remains in the art a need for catechin compounds with improved therapeutic profiles for treatment of such diseases and conditions.

Novel compounds and pharmaceutical compositions, certain of which have been found to modulate mitochondrial function have been discovered, together with methods of synthesizing and using the compounds including methods for the treatment of mitochondrial-mediated diseases in a patient by administering the compounds.

In certain embodiments of the present invention, compounds have structural Formula I:

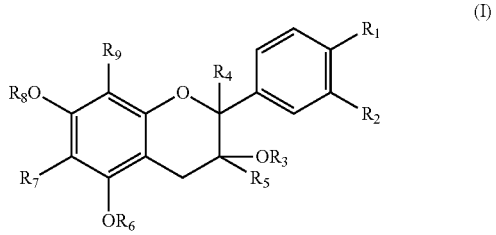

(I)

or pharmaceutically acceptable salts thereof, wherein the compound is the (2R,3R) diastereomer, or a racemic mixture of the (2R,3R) and (2S,3S) diastereomers;

$R_1$ and $R_2$ are independently in each occurrence selected from the group consisting of hydrogen; hydroxyl; —$C_{1-6}$ alkoxy, wherein the $C_{1-6}$ alkoxy is unsubstituted or substituted with 1 substituent selected from the group consisting of amino, hydroxyl, —C(O)OH, —C(O)NH$_2$, and —C(O)O—($C_{1-3}$ alkyl), —OCH$_2$-cyclopropyl, —NR$_{12}$R$_{13}$, —(CH$_2$)$_{1-2}$OR$_{11}$, —(CH$_2$)$_{1-2}$NR$_{12}$R$_{13}$, —C(O)R$_{11}$, —SO$_2$R$_{11}$, —C(O)OR$_{11}$, —SO$_2$NR$_{12}$R$_{13}$, —C(O)NR$_{12}$R$_{13}$, or, —P(O)OR$_{12}$OR$_{13}$; —OA; and —$R_1$ and —$R_2$ taken together with the atoms to which they attach form a 5- or 6-member carbocyclic, heterocyclic, aryl or heteroaryl ring which is unsubstituted or substituted with 1, 2, or 3 substituents independently selected from the list consisting of halo, methyl, and methoxy;

$R_3$ is —$C_{1-6}$ alkyl or —C(O)R$_{14}$, wherein the alkyl is unsubstituted or substituted with 1 substituent selected from the list consisting of —OR$_{11}$, —NR$_{12}$R$_{13}$, —SO$_2$R$_{11}$, —C(O)OR$_{11}$, —SO$_2$NR$_{12}$R$_{13}$, —C(O)NR$_{12}$R$_{13}$, —P(O)OR$_{12}$OR$_{13}$; or -A;

$R_4$ and $R_5$ are independently in each occurrence selected from the group consisting of hydrogen; —$C_{1-4}$ alkyl; and —$R_4$ and —$R_5$ taken together with the atoms to which they attach form a 3-member ring optionally incorporating O;

$R_6$ and $R_8$ are independently in each occurrence selected from the group consisting of hydrogen; —$C_{1-4}$ alkyl, wherein the $C_{1-4}$ alkyl is unsubstituted or substituted with 1 substituent selected from the group consisting of amino, hydroxyl, —C(O)OH, —C(O)NH$_2$, and —C(O)O—($C_{1-3}$ alkyl); —OCH$_2$-cyclopropyl; and -A;

$R_7$ and $R_9$ are independently in each occurrence selected from the group consisting of hydrogen; —$C_{1-6}$ alkyl, wherein the $C_{1-6}$ alkyl is unsubstituted or substituted with 1 substituent selected from the list consisting of amino, —C(O)OH, —C(O)NH$_2$, and —C(O)O—($C_{1-3}$ alkyl); —NR$_{12}$R$_{13}$; —(—CH$_2$)$_{1-2}$OR$_{11}$; —(CH$_2$)$_{1-2}$NR$_{12}$R$_{13}$; —C(O)R$_{11}$; —SO$_2$R$_{11}$; —C(O)OR$_{11}$; —SO$_2$NR$_{12}$R$_{13}$; —C(O)NR$_{12}$R$_{13}$; —P(O)OR$_{12}$OR$_{13}$; $R_7$ and $R_6$ or $R_8$ when taken together with the atoms to which they attach optionally form a 5- to 7-member ring optionally incorporating one or two ring heteroatoms chosen from N, O, or S, and which is unsubstituted or substituted with 1, 2, or 3 substituents independently selected from the list consisting of halo, methyl and methoxy; and $R_9$ and $R_8$ when taken together with the atoms to which they attach optionally form a 5- to 7-member ring optionally incorporating one or two ring heteroatoms chosen from N, O, or S, and which is unsubstituted or substituted with 1, 2, or 3 substituents independently selected from the list consisting of halo, methyl and methoxy; where n is 1, 2, 3, or 4;

each A is independently selected from the group consisting of

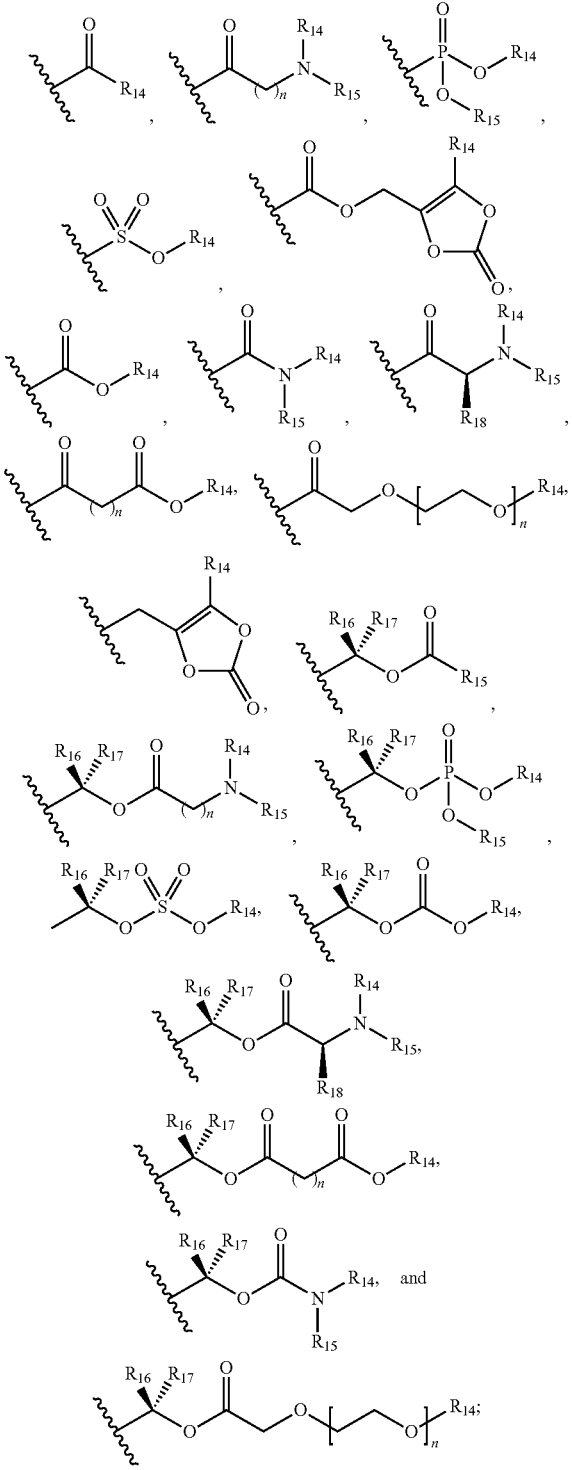

each $R_{11}$ is independently selected from the group consisting of hydrogen, $C_{1-3}$ alkyl, or $C_{1-3}$ haloalkyl;

each $R_{12}$ and $R_{13}$ is independently selected from the group consisting of H; $C_{1-3}$ alkyl; $C_{1-3}$ haloalkyl; and $R_{12}$ and $R_{13}$ taken together with the atoms to which they attach to form a 5- to 7-member ring optionally incorporating one or two ring heteroatoms chosen from N, O, or S, which is optionally substituted with 1 to 4 substituents selected from the list consisting of halo, methyl and methoxy;

each $R_{14}$ and $R_{15}$ is independently selected from the group consisting of H; $C_{1-6}$ alkyl; $C_{1-6}$ haloalkyl; phenyl or phenymethyl, wherein the phenyl portion of the phenyl or phenylmethyl groups are unsubstituted or substituted with 1, 2, or 3 substituents independently selected from the list consisting of halo, methoxy, trifluormethoxy, or amino; and $R_{14}$ and $R_{15}$ taken together with the atoms to which they attach form a 5- to 7-member ring optionally incorporating one or two ring heteroatoms chosen from N, O, or S, which is unsubstituted or substituted with 1, 2, or 3 substituents independently selected from the list consisting of halo, methyl and methoxy;

$R_{16}$ and $R_{17}$ are independently in each occurrence hydrogen or $C_{1-10}$ alkyl; and each $R_{18}$ is independently selected from the group consisting of hydrogen and $C_{1-6}$ alkyl, wherein the $C_{1-6}$ alkyl is unsubstituted or substituted with 1 substituent selected from the list consisting of hydroxyl, methoxy, amino, thio, methylthio, —C(O)OH, —C(O)O—($C_{1-3}$ alkyl), —CONH$_2$, phenyl, wherein the phenyl is unsubstituted or substituted from the list consisting of halo and hydroxyl; and Certain compounds disclosed herein may possess mitochondrial activity modulating activity, and may be used in the treatment or prophylaxis of a disease or condition in which mitochondrial activity plays an active role. Thus, in broad aspect, certain embodiments also provide pharmaceutical compositions comprising one or more compounds disclosed herein together with a pharmaceutically acceptable carrier, as well as methods of making and using the compounds and compositions. Certain embodiments provide methods for modulating mitochondrial function. Other embodiments provide methods for treating a mitochondrial-mediated disorder in a patient in need of such treatment, comprising administering to said patient a therapeutically effective amount of a compound or composition according to the present invention. Also provided is the use of certain compounds disclosed herein for use in the manufacture of a medicament for the treatment of a disease or condition ameliorated by the modulation of mitochondrial function.

In certain embodiments, when $R_7$ and $R_9$ are individually or in any combination halo or $C_{1-6}$ alkyl, wherein the $C_{1-6}$ alkyl is unsubstituted or substituted with phenyl, that the following are not all true, $R_1$ is methoxy, $R_2$ is methoxy, $R_6$ is methyl, and $R_8$ is methyl; when $R_7$ and $R_9$ are individually or in any combination halo or $C_{1-6}$ alkyl, wherein the $C_{1-6}$ alkyl is unsubstituted or substituted with phenyl, that the following are not all true: $R_1$ is hydroxyl, $R_2$ is hydroxyl, $R_6$ is H, and $R_8$ is H; when $R_4$, $R_5$, $R_7$, and $R_9$ are all H, the following are not all true: $R_1$ is hydroxyl or methoxy, $R_2$ is hydroxyl or methoxy, $R_3$ is H or methyl, $R_6$ is H or methyl, and $R_8$ is H or methyl.

In further embodiments, compounds have structural formula II:

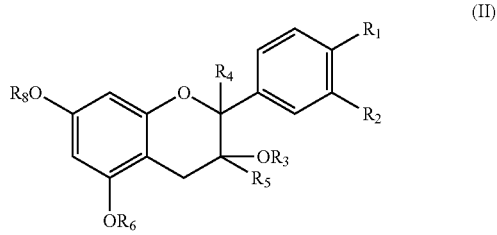

(II)

or pharmaceutically acceptable salts thereof, wherein the compound is the (2R,3R) diastereomer, or a racemic mixture of the (2R,3R) and (2S,3S) diastereomers;

$R_1$ and $R_2$ are independently in each occurrence selected from the group consisting of hydrogen; hydroxyl; —$C_{1-6}$ alkoxy, wherein the $C_{1-6}$ alkoxy is unsubstituted or substituted with 1 substituent selected from the group consisting of amino, —C(O)OH, —C(O)NH$_2$, and —C(O)O—($C_{1-3}$ alkyl); —OCH$_2$-cyclopropyl; —NR$_{12}$R$_{13}$; —(CH$_2$)$_{1-2}$OR$_{11}$; —(CH$_2$)$_{1-2}$NR$_{12}$R$_{13}$; —C(O)R$_{11}$; —SO$_2$R$_{11}$; —C(O)OR$_{11}$; —SO$_2$NR$_{12}$R$_{13}$; —C(O)NR$_{12}$R$_{13}$; —P(O)OR$_{12}$OR$_{13}$; —OA; and $R_1$ and $R_2$ taken together with the atoms to which they attach form a 5- or 6-member carbocyclic, heterocyclic, aryl or heteroaryl ring which is unsubstituted or substituted with 1, 2, or 3 substituents independently selected from the list consisting of halo, methyl and methoxy;

$R_3$ is selected from the group consisting of —$C_{1-6}$ alkyl, wherein the $C_{1-6}$ alkyl is unsubstituted or substituted with 1 substituent selected from the list consisting of —OR$_{11}$, —NR$_{12}$R$_{13}$, —SO$_2$R$_{11}$, —C(O)OR$_{11}$, —SO$_2$NR$_{12}$R$_{13}$, —C(O)NR$_{12}$R$_{13}$, —P(O)OR$_{12}$OR$_{13}$; and -A;

$R_4$ and $R_5$ are independently in each occurrence selected from the group consisting of hydrogen; —$C_{1-4}$ alkyl; and $R_4$ and $R_5$ taken together with the atoms to which they attach form a 3-member ring optionally incorporating O;

$R_6$ and $R_8$ are independently in each occurrence selected from the group consisting of hydrogen; —$C_{1-4}$ alkyl; and -A;

with the proviso that when $R_4$ are $R_5$ are both H, the following are not all true: $R_1$ is hydroxyl or methoxy, $R_2$ is hydroxyl or methoxy, $R_3$ is hydroxyl or methoxy, $R_6$ is H or methyl, and $R_8$ is H or methyl.

In further embodiments, compounds have structural formula III:

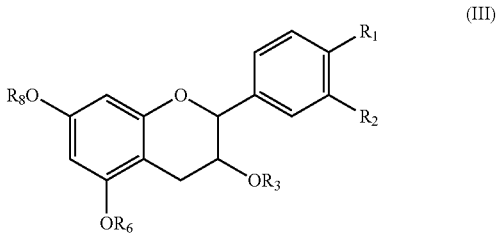

(III)

or pharmaceutically acceptable salts thereof, wherein the compound is the (2R,3R) diastereomer, or a racemic mixture of the (2R,3R) and (2S,3S) diastereomers;

R₁ and R₂ are independently in each occurrence selected from the group consisting of hydroxyl; —C₁₋₆ alkoxy, wherein the C₁₋₆ alkoxy is unsubstituted or substituted with 1 substituent selected from the group consisting of amino, hydroxyl, —C(O)OH, —C(O)NH₂, and —C(O)O—(C₁₋₃ alkyl); and —O-A;

R₃ is selected from the group consisting of hydrogen; —C₁₋₆ alkyl; -A;

R₆ and R₈ are independently in each occurrence selected from the group consisting of hydrogen; —C₁₋₄ alkyl; and -A; with the proviso that the following are not all true: R₁ is hydroxyl or methoxy, R₂ is hydroxyl or methoxy, R₃ is H or methyl, R₆ is H or methyl, and R₈ is H or methyl.

In further embodiments, compounds have structural formula III:

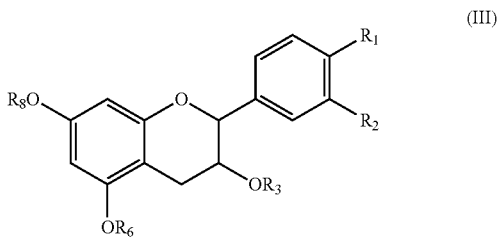

(III)

or pharmaceutically acceptable salts thereof, wherein
the compound is the (2R,3R) diastereomer, or a racemic mixture of the (2R,3R) and (2S,3S) diastereomers;

R₁ and R₂ are independently in each occurrence selected from the group consisting of hydroxyl; and —C₁₋₆ alkoxy, wherein the C₁₋₆ alkoxy is unsubstituted or substituted with 1 substituent selected from the group consisting of amino, hydroxyl, —C(O)OH, —C(O)NH₂, and —C(O)O—(C₁₋₃ alkyl);

R₃ is hydrogen or —C₁₋₆ alkyl;

R₆ and R₈ are independently in each occurrence hydrogen or —C₁₋₄ alkyl; with the proviso that the following are not all true: R₁ is hydroxyl or methoxy, R₂ is hydroxyl or methoxy, R₃ is H or methyl, R₆ is H or methyl, and R₈ is H or methyl.

In further embodiments, compounds have structural formula II:

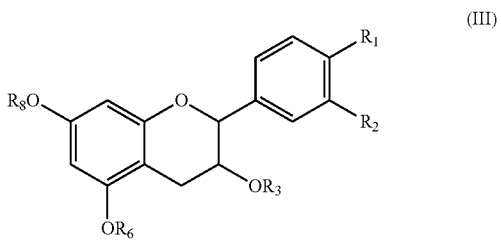

(III)

or pharmaceutically acceptable salts thereof, wherein
the compound is the (2R,3R) diastereomer, or a racemic mixture of the (2R,3R) and (2S,3S) diastereomers;

R₁ and R₂ are independently in each occurrence hydroxyl or —O-A;

R₃ is hydrogen or -A;

R₆ and R₈ are independently in each occurrence hydrogen or -A;

with the proviso that the compound is not epicatechin

In further embodiments, compounds disclosed herein are selected from the group consisting of:
2-(4-Hydroxy-3-propoxy-phenyl)-chroman-3,5,7-triol;
2-(3-Hydroxy-4-propoxy-phenyl)-chroman-3,5,7-triol;
2-(3-Ethoxy-4-hydroxy-phenyl)-chroman-3,5,7-triol;
2-(4-Ethoxy-3-hydroxy-phenyl)-chroman-3,5,7-triol;
2-(3,4-Dihydroxy-phenyl)-3-propoxy-chroman-5,7-diol;
methyl 4-((2R,3R)-3-hydroxy-5,7-dimethoxychroman-2-yl)-2-methoxybenzoate;
methyl 5-((2R,3R)-3-hydroxy-5,7-dimethoxychroman-2-yl)-2-methoxybenzoate;
(4-((2R,3R)-3-hydroxy-5,7-dimethoxychroman-2-yl)-2-methoxyphenyl)(4-methylpiperazin-1-yl)methanone;
ethyl 2-(4-((2R,3R)-3-hydroxy-5,7-dimethoxychroman-2-yl)-2-methoxyphenoxy)acetate;
ethyl 2-(5-((2R,3R)-3-hydroxy-5,7-dimethoxychroman-2-yl)-2-methoxyphenoxy)acetate;
2-(4-((2R,3R)-3-hydroxy-5,7-dimethoxychroman-2-yl)-2-methoxyphenoxy)acetic acid;
ethyl 2-(2-hydroxy-4-((2R,3R)-3,5,7-trihydroxychroman-2-yl)phenoxy)acetate;
ethyl 2-(2-hydroxy-5-((2R,3R)-3,5,7-trihydroxychroman-2-yl)phenoxy)acetate;
(2R,3R)-2-(3,4-dihydroxyphenyl)-3-methoxychroman-5,7-diol;
((2R,3R)-2-(3,4-dihydroxyphenyl)-3-ethoxychroman-5,7-diol;
(2R,3R)-2-(3,4-dihydroxyphenyl)-5,7-dihydroxychroman-3-yl acetate;
1-(((2R,3R)-2-(3,4-dihydroxyphenyl)-5,7-dihydroxychroman-3-yl)oxy)ethyl isobutyrate;
(((2R,3R)-2-(3,4-dihydroxyphenyl)-5,7-dihydroxychroman-3-yl)oxy)methyl diisopropylcarbamate;
tert-butyl ((((2R,3R)-2-(3,4-dihydroxyphenyl)-5,7-dihydroxychroman-3-yl)oxy)methyl)carbonate;
4-((2R,3R)-3,5,7-trihydroxychroman-2-yl)-1,2-phenylene dioctanoate;
(2R,3R)-2-(3,4-dihydroxyphenyl)-5,7-dihydroxychroman-3-yl octanoate;
(2R,3R)-2-(3,4-diacetoxyphenyl)chroman-3,5,7-triyl triacetate;
4-((2R,3R)-3,5,7-trihydroxychroman-2-yl)-1,2-phenylene diacetate;
4-((2R,3R)-3,5,7-trihydroxychroman-2-yl)-1,2-phenylene diacetate; and
(2R,3R)-2-(3,4-dihydroxyphenyl)-3-methylchroman-3,5,7-triol;
or a racemic mixture of the (2R,3R) and (2S,3S) diastereomers;
or a pharmaceutically acceptable salt thereof.

In further embodiments, disclosed herein is a pharmaceutical composition comprising a compound or pharmaceutically acceptable salt disclosed herein and a pharmaceutically acceptable excipient.

In further embodiments, disclosed herein is a pharmaceutical composition comprising a compound or pharmaceutically acceptable salt disclosed herein and a pharmaceutically acceptable excipient.

In further embodiments, disclosed herein is a pharmaceutical composition formulated for a parenteral route of administration.

In further embodiments, disclosed herein is a pharmaceutical composition further comprising one or more compounds independently selected from the group consisting of nicorandil, a nicorandil derivative, tetracycline antibiotics, glycoprotein IIb/IIIa inhibitors, ADP receptor/P2Y12 inhibitors, prostaglandin analogues, COX inhibitors, antiplatelet drugs, anticoagulants, heparins, direct factor Xa inhibitors, direct thrombin (II) inhibitors, and vasodilators.

In further embodiments, disclosed herein is a method for treating an ischemic or ischemia/reperfusion condition in an animal, or for prophylaxis in an animal at risk of an ischemic or ischemia/reperfusion condition, comprising: administering to said animal by a parenteral or enteral route an effective amount of a derivative or pharmaceutically acceptable salt disclosed herein.

In further embodiments, said method comprises administering to said animal a pharmaceutical composition disclosed herein.

In further embodiments, said animal is a mammal.

In further embodiments, said animal is a human.

In further embodiments, said administering is via a parenteral route.

In further embodiments, said animal is administered a derivative or pharmaceutically acceptable salt disclosed herein within 48 hours of the onset of an acute ischemic or ischemia/reperfusion event or within 48 hours of presentation for medical treatment for an acute ischemia/reperfusion event.

In further embodiments, said derivative or pharmaceutically acceptable salt is administered together with one or more compounds independently selected from the group consisting of nicroandil, a nicorandil derivative, tetracycline antibiotics, glycoprotein IIb/IIIa inhibitors, ADP receptor/P2Y12 inhibitors, prostaglandin analogues, COX inhibitors, antiplatelet drugs, anticoagulants, heparins, direct factor Xa inhibitors, direct thrombin (II) inhibitors, and vasodilators.

In further embodiments, said animal is suffering or at immediate risk of suffering from an acute ischemic or ischemia/reperfusion event selected from the group consisting of myocardial infarction, acute ischemic renal injury, a disease of the aorta and its branches, and an ischemic injury arising from a medical intervention.

In further embodiments, said ischemic or ischemia/reperfusion event is an acute ischemic or ischemia/reperfusion event.

In further embodiments, disclosed herein is a method of treating an ischemic or ischemia/reperfusion (IR) condition in a subject, comprising: administering to a subject in need thereof an effective amount of a compound or pharmaceutically acceptable salt disclosed herein, together with one or more second compounds independently selected from the group consisting of nicorandil, a nicorandil derivative, glycoprotein IIb/IIIa inhibitors, ADP receptor/P2Y12 inhibitors, prostaglandin analogues, COX inhibitors, antiplatelet drugs, anticoagulants, heparins; direct factor Xa inhibitors, direct thrombin (II) inhibitors, and vasodilators.

In further embodiments, said ischemic or ischemia/reperfusion (IR) condition is an acute ischemic event.

In further embodiments, said acute ischemic event is a myocardial infarction.

In further embodiments, said acute ischemic event is an acute angina event.

In further embodiments, said acute ischemic event is acute kidney injury.

In further embodiments, said acute ischemic event is a total coronary occlusion.

In further embodiments, said acute ischemic event is an acute stroke.

In further embodiments, said acute ischemic event is atrial fibrillation.

In further embodiments, said ischemic or ischemia/reperfusion (IR) condition is the occurrence of medical intervention causing temporary acute ischemia.

In further embodiments, the medical intervention is selected from the group consisting of CABG surgery, cardiac surgery involving cardiopulmonary bypass, aneurysm repair, angioplasty, and administration of a radiocontrast agent.

In further embodiments, said drug combination is administered between 48 hours prior to said medical intervention and 48 hours following said medical intervention.

In further embodiments, said one or more second compounds are selected from the group consisting of eptifibatide, tirofiban, abciximab, clopidogrel, ticlopidine, prasgurel, betaprost, iloprost, treprostinil, asprin, aloxiprin, ditazole, cloricromen, dipyridamole, indobufen, picotamide, triflusal, coumarins, a 1,3-indandione anticoagulant, heparin, bivalirudin, nicorandil, fendoldopam, hydralazine, nesiritide, nicardipine, nitroglycerine, and nitroprusside.

In further embodiments, said drug combination further comprises one or more tetracycline antibiotics.

In further embodiments, wherein said first compound and said one or more second compounds are each delivered by enteral routes of administration.

In further embodiments, said first compound and said one or more second compounds are each delivered by parenteral routes of administration.

In further embodiments, disclosed herein is a method of reducing tolerance development to vasodilator drugs, comprising administering to a subject in need thereof an effective amount of a drug combination comprising a compound or pharmaceutically acceptable salt disclosed herein together with one or more vasodilators.

In further embodiments, said one or more vasodilators are independently selected from the group consisting of nicorandil, a nicorandil derivative, nitrate donor vasodilators, ACE inhibitors, and anigotensin receptor blockers.

In further embodiments, said one or more vasodilators are selected from the group consisting of nicorandil, nitroprusside and nitroglycerine.

In further embodiments, said first compound and said one or more vasodilators are each delivered by enteral routes of administration.

In further embodiments, disclosed herein is a method of stimulating mitochondrial function in cells, comprising administering one or more compounds or pharmaceutically acceptable salts disclosed herein in an amount effective to stimulate mitochondrial function in said cells.

In further embodiments, said stimulation of mitochondrial function in said cells comprises stimulation of mitochondrial respiration in said cells.

In further embodiments, said stimulation of mitochondrial function in said cells comprises stimulation of mitochondrial biogenesis in said cells.

In further embodiments, said administration comprises administering at least 0.1 µM of a compound or pharmaceutically acceptable salt disclosed herein to said cells.

In further embodiments, said at least 0.1 µM of a compound or pharmaceutically acceptable salt disclosed herein is maintained at least 30 minutes, 1 hour, 3 hours, 12 hours, 24 hours, or 48 hours.

In further embodiments, disclosed herein is a said administering step comprises delivering said one or more compounds or pharmaceutically acceptable salts disclosed herein to an animal by a parenteral or enteral route in an amount effective to stimulate mitochondrial function in cells of said animal.

In further embodiments, said animal is a human.

In further embodiments, said animal is selected for said administering step based on a diagnosis that said animal is suffering from or at immediate risk of suffering from one or more conditions selected from the group consisting of an inborn error of mitochondrial biogenesis or bioenergetics, a dietary deficiency, a vitamin deficiency, diabetes, metabolic syndrome, Friedreich's ataxia, pulmonary hypertension, chronic kidney disease (particularly that associated with glomerular epithelial injury or tubulointerstitial fibrosis, including diabetic nephropathy, focal segmental glomerulosclerosis, and chronic renal insufficiency), acute kidney injury (whether due to vascular insufficiency, drug effects, toxins, medical or surgical procedures, or otherwise), hypertension, dementia, heart failure, obesity, hyperlipidemia, insulin resistance, a muscular condition involving decreased mitochondrial function, impaired cognition related to aging, vascular disease, metabolic impairment or neurodegeneration, and a neurological condition involving decreased mitochondrial function.

In further embodiments, said animal is selected for said administering step based on age of said animal.

In further embodiments, said animal is selected for said administering step based on an activity state of said animal.

In further embodiments, said administering step comprises delivering said one or more compounds or pharmaceutically acceptable salts disclosed herein to an animal by an oral route in an amount effective to maintain a plasma concentration of at least 0.1 μM of said compound in said animal for at least 30 minutes, 1 hour, 3 hours, 12 hours, 24 hours, or 48 hours.

In further embodiments, said one or more compounds or pharmaceutically acceptable salts disclosed herein to an animal by an oral route in an amount effective to maintain a plasma concentration of at least 1 μM of said compound in said animal for at least 30 minutes, 1 hour, 3 hours, 12 hours, 24 hours, or 48 hours.

In further embodiments, disclosed herein is a method of treating a condition involving decreased mitochondrial function in an animal, said method comprising delivering to said animal one or more compounds or pharmaceutically acceptable salts disclosed herein by a parenteral or enteral route in an amount effective to stimulate mitochondrial function in cells of said animal.

In further embodiments, said condition involving decreased mitochondrial function is selected from the group consisting of an inborn error of mitochondrial biogenesis or bioenergetics, a dietary deficiency, a vitamin deficiency, diabetes, metabolic syndrome, Friedreich's ataxia, pulmonary hypertension, chronic kidney disease (particularly that associated with glomerular epithelial injury or tubulointerstitial fibrosis, including diabetic nephropathy, focal segmental glomerulosclerosis, and chronic renal insufficiency), acute kidney injury (whether due to vascular insufficiency, drug effects, toxins, medical or surgical procedures, or otherwise), hypertension, dementia, heart failure, obesity, hyperlipidemia, insulin resistance, a muscular condition involving decreased mitochondrial function, impaired cognition related to aging, vascular disease, metabolic impairment or neurodegeneration, and a neurological condition involving decreased mitochondrial function.

In further embodiments, said condition involving decreased mitochondrial function is related to the age and/or activity state of said animal.

In further embodiments, said condition involving decreased mitochondrial function is related to a nutritional state of said animal.

In further embodiments, said administering step comprises delivering to said animal said one or more compounds or pharmaceutically acceptable salts disclosed herein by an oral route in an amount effective to maintain a plasma concentration of at least 0.1 μM of said compound in said animal for at least 30 minutes, 1 hour, 3 hours, 12 hours, 24 hours, or 48 hours.

In further embodiments, said method comprises delivering to said animal said one or more compounds or pharmaceutically acceptable salts disclosed herein by an oral route in an amount effective to maintain a plasma concentration of at least 1 μM of said compound in said animal for at least 30 minutes, 1 hour, 3 hours, 12 hours, 24 hours, or 48 hours.

In further embodiments, disclosed herein is a method for improving muscle structure or function in an animal, comprising: administering one or more compounds or pharmaceutically acceptable salts disclosed herein to said animal in an amount effective to stimulate mitochondrial function in cells, thereby improving muscle structure or function in said animal.

In further embodiments, disclosed herein is a method for improving mitochondrial effects associated with exercise in an animal, comprising administering one or more compounds or pharmaceutically acceptable salts disclosed herein to said animal in an amount effective to stimulate mitochondrial function in cells, thereby improving mitochondrial effects associated with exercise in said animal.

In further embodiments, disclosed herein is a method for enhancing the capacity for exercise in an animal, comprising: administering one or more compounds or pharmaceutically acceptable salts disclosed herein to said animal in an amount effective to stimulate mitochondrial function in cells, thereby enhancing the capacity for exercise in said animal.

In further embodiments, disclosed herein is a method for enhancing muscle health and function in response to exercise in an animal, comprising administering one or more compounds or pharmaceutically acceptable salts disclosed herein to said animal in an amount effective to stimulate mitochondrial function in cells, thereby enhancing muscle health and function in response to exercise in said animal.

In further embodiments, disclosed herein is a method for enhancing muscle health and function in a clinical setting of restricted capacity for exercise in an animal, comprising administering one or more compounds or pharmaceutically acceptable salts disclosed herein to said animal in an amount effective to stimulate mitochondrial function in cells, thereby enhancing muscle health and function in said animal.

In further embodiments, disclosed herein is a method for enhancing recovery of muscles from vigorous activity or from injury associated with vigorous or sustained activity in an animal, comprising administering one or more compounds or pharmaceutically acceptable salts disclosed herein to said animal in an amount effective to stimulate mitochondrial function in cells, thereby enhancing recovery of muscles in said animal.

In further embodiments, said administration comprises administering at least 0.1 μM of said one or more compounds or pharmaceutically acceptable salts disclosed herein to said cells.

In further embodiments, said at least 0.1 μM of said one or more compounds or pharmaceutically acceptable salts disclosed herein is maintained at least 30 minutes, 1 hour, 3 hours, 12 hours, 24 hours, or 48 hours.

In further embodiments, said at least 1 μM of said one or more compounds or pharmaceutically acceptable salts disclosed herein is maintained for at least 30 minutes, 1 hour, 3 hours, 12 hours, 24 hours, or 48 hours.

In further embodiments, said one or more compounds or pharmaceutically acceptable salts disclosed herein is delivered in a manner that achieves a plasma concentration in said animal of at least 0.1 μM at least once during a first 12 hour period, and a plasma concentration of at least 0.1 µM at least once during a second 12 hour period immediately following said first 12 hour period, and optionally in one or more subsequent 12 hour periods continuous with said first and second 12 hour periods.

In further embodiments, said one or more compounds or pharmaceutically acceptable salts disclosed herein is delivered in a manner that achieves a plasma concentration in said animal of at least 0.1 µM at least once during a first 24 hour period, and a plasma concentration of at least 0.1 µM at least once during a second 24 hour period immediately following said first 24 hour period, and optionally in one or more subsequent 24 hour periods continuous with said first and second 24 hour periods.

In further embodiments, said administering step comprises delivering said one or more compounds or pharmaceutically acceptable salts disclosed herein to an animal by a parenteral or enteral route.

In further embodiments, said animal is a human.

In further embodiments, disclosed herein is a pharmaceutical or nutraceutical composition comprising one or more compounds or pharmaceutically acceptable salts disclosed herein and nicorandil or a nicorandil derivative.

In further embodiments, disclosed herein is a pharmaceutical or nutraceutical composition comprising an admixture of one or more compounds or pharmaceutically acceptable salts disclosed herein with nicorandil or a nicorandil derivative.

In further embodiments, disclosed herein is the use of one or more compounds or pharmaceutically acceptable salts disclosed herein for treatment of one or more conditions selected from the group consisting of an inborn error of mitochondrial biogenesis or bioenergetics, a dietary deficiency, a vitamin deficiency, diabetes, metabolic syndrome, Friedreich's ataxia, pulmonary hypertension, chronic kidney disease (particularly that associated with glomerular epithelial injury or tubulointerstitial fibrosis, including diabetic nephropathy, focal segmental glomerulosclerosis, and chronic renal insufficiency), acute kidney injury (whether due to vascular insufficiency, drug effects, toxins, medical or surgical procedures, or otherwise), hypertension, dementia, heart failure, obesity, hyperlipidemia, insulin resistance, a muscular condition involving decreased mitochondrial function, impaired cognition related to aging, vascular disease, metabolic impairment or neurodegeneration, and a neurological condition involving decreased mitochondrial function; or a method for treatment of one or more conditions selected from the group consisting of an inborn error of mitochondrial biogenesis or bioenergetics, a dietary deficiency, a vitamin deficiency, diabetes, metabolic syndrome, Friedreich's ataxia, pulmonary hypertension, chronic kidney disease (particularly that associated with glomerular epithelial injury or tubulointerstitial fibrosis, including diabetic nephropathy, focal segmental glomerulosclerosis, and chronic renal insufficiency), acute kidney injury (whether due to vascular insufficiency, drug effects, toxins, medical or surgical procedures, or otherwise), hypertension, dementia, heart failure, obesity, hyperlipidemia, insulin resistance, a muscular condition involving decreased mitochondrial function, impaired cognition related to aging, vascular disease, metabolic impairment or neurodegeneration, and a neurological condition involving decreased mitochondrial function comprising administering epicatechin or an epicatechin derivative to a patient in need thereof; or a method for prophylaxis in an animal at risk of impairment of mitochondrial biogenesis or bioenergetics, comprising administering epicatechin or an epicatechin derivative to a patient in need thereof.

In further embodiments, disclosed herein is the use of one or more compounds or pharmaceutically acceptable salts disclosed herein in combination with nicorandil or a nicorandil derivative for treatment of one or more conditions selected from the group consisting of an inborn error of mitochondrial biogenesis or bioenergetics, a dietary deficiency, a vitamin deficiency, diabetes, metabolic syndrome, Friedreich's ataxia, pulmonary hypertension, chronic kidney disease (particularly that associated with glomerular epithelial injury or tubulointerstitial fibrosis, including diabetic nephropathy, focal segmental glomerulosclerosis, and chronic renal insufficiency), acute kidney injury (whether due to vascular insufficiency, drug effects, toxins, medical or surgical procedures, or otherwise), hypertension, dementia, heart failure, obesity, hyperlipidemia, insulin resistance, a muscular condition involving decreased mitochondrial function, impaired cognition related to aging, vascular disease, metabolic impairment or neurodegeneration, and a neurological condition involving decreased mitochondrial function; or a method for treatment of one or more conditions selected from the group consisting of an inborn error of mitochondrial biogenesis or bioenergetics, a dietary deficiency, a vitamin deficiency, diabetes, metabolic syndrome, Friedreich's ataxia, pulmonary hypertension, chronic kidney disease (particularly that associated with glomerular epithelial injury or tubulointerstitial fibrosis, including diabetic nephropathy, focal segmental glomerulosclerosis, and chronic renal insufficiency), acute kidney injury (whether due to vascular insufficiency, drug effects, toxins, medical or surgical procedures, or otherwise), hypertension, dementia, heart failure, obesity, hyperlipidemia, insulin resistance, a muscular condition involving decreased mitochondrial function, impaired cognition related to aging, vascular disease, metabolic impairment or neurodegeneration, and a neurological condition involving decreased mitochondrial function comprising administering epicatechin or an epicatechin derivative in combination with nicorandil or a nicorandil derivative to a patient in need thereof; or a method for prophylaxis in an animal at risk of impairment of mitochondrial biogenesis or bioenergetics, comprising administering epicatechin or an epicatechin derivative in combination with nicorandil or a nicorandil derivative to a patient in need thereof.

In further embodiments, disclosed herein is a method of ameliorating the effects of a chemical composition which causes a perturbation in mitochondrial number, function, or structure in a subject, comprising administering an effective amount of one or more compounds or pharmaceutically acceptable salts disclosed herein to said subject.

In further embodiments, said effective amount achieves a plasma concentration of said one or more compounds which stimulates mitochondrial function in cell culture.

In further embodiments, said stimulation of mitochondrial function comprises stimulation of mitochondrial respiration in said cell culture.

In further embodiments, said stimulation of mitochondrial function comprises stimulation of mitochondrial biogenesis in said cell culture.

In further embodiments, said one or more compounds or pharmaceutically acceptable salts disclosed herein are administered to said subject together with the chemical composition which causes mitochondrial toxicity.

In further embodiments, said one or more compounds or pharmaceutically acceptable salts disclosed herein are administered prophylactically to said subject prior to administration of the chemical composition which causes mitochondrial toxicity.

In further embodiments, said one or more compounds or pharmaceutically acceptable salts disclosed herein are administered to said subject following manifestation of mitochondrial toxicity by said subject.

In further embodiments, said one or more compounds or pharmaceutically acceptable salts disclosed herein are administered to said subject to treat or prevent one or more conditions selected from the group consisting of myopathy, diabetes, weight gain, impaired cognition, loss of energy, fatigue, cardiovascular toxicity, hepatic toxicity, renal toxicity, and increased serum lipids.

In further embodiments, said administering step comprises delivering one or more compounds or pharmaceutically acceptable salts disclosed herein free of polyphenols naturally occurring in green tea or chocolate.

In further embodiments, said administering step comprises delivering one or more compounds or pharmaceutically acceptable salts disclosed herein to an animal by a parenteral or enteral route in an amount effective to stimulate mitochondrial function in cells of said subject.

In further embodiments, said subject is a human.

In further embodiments, said method further comprises an increased duration of treatment, wherein the duration of treatment with the chemical composition which causes mitochondrial toxicity would otherwise be limited by its toxicity.

In further embodiments, said method further comprises administering an increased concentration of the chemical composition which causes mitochondrial toxicity, wherein said increased concentration would otherwise be limited by its toxicity.

In further embodiments, said administering step comprises administering an effective amount of one or more compounds or pharmaceutically acceptable salts disclosed herein together with an effective amount of one or more compounds selected from the group consisting of an antipsychotic, olanzepine, clozapine, risperidone, quetiapnie, a nucleoside reverse transcriptase inhibitor, zidovudine, bupivacaine, lidocaine, thiazolidinediones, doxorubicin, sorafenib, daunorubicin, epirubicin, idarubicin, celecoxib, diclofenac, ibuprofen, indomethacin, mefenamic acid, meloxicam, naproxen, piroxicam, sulindac, atenolol, pioglitazone, rosiglitazone, isoniazid, valproic acid, tamoxifen, flutamide, lamivudine, zalcitabine, phenoformin, metformin, nefazodone, abacavir, didanosine, nevirapine, tenofovir, stavudine, ketoconazole, divalproex sodium, cysplatin, gentamicin, ifosfamide, a statin, tenofovir, metformin, a corticosteroid, cortisol, prednisone, dexamethasone, triamcinalone, prednisolone, an inotrope, epinephrine, isoproterenol, a fibrate, clofibrate, gemfibrizole, cyprofibrate, and bezafibrate.

In further embodiments, said administering step comprises administering an effective amount of one or more compounds selected from the group consisting of epicatechin and an epicatechin derivative.

In further embodiments, said administering step comprises administering chocolate and/or a green tea extract.

In further embodiments, disclosed herein is a pharmaceutical composition comprising a chemical composition which causes a perturbation in mitochondrial number, function, or structure when administered to a subject, and one or more compounds or pharmaceutically acceptable salts disclosed herein.

In further embodiments, disclosed herein is a pharmaceutical composition comprising: one or more compounds or pharmaceutically acceptable salts disclosed herein; and one or more compounds selected from the group consisting of an antipsychotic, olanzepine, clozapine, risperidone, quetiapnie, a nucleoside reverse transcriptase inhibitor, zidovudine, bupivacaine, lidocaine, thiazolidinediones, doxorubicin, sorafenib, daunorubicin, epirubicin, idarubicin, celecoxib, diclofenac, ibuprofen, indomethacin, mefenamic acid, meloxicam, naproxen, piroxicam, sulindac, atenolol, pioglitazone, rosiglitazone, isoniazid, valproic acid, tamoxifen, flutamide, lamivudine, zalcitabine, phenoformin, metformin, nefazodone, abacavir, didanosine, nevirapine, tenofovir, stavudine, ketoconazole, divalproex sodium, cysplatin, gentamicin, a cyclosporin, ifosfamide, a statin, tenofovir, metformin, a corticosteroid, cortisol, prednisone, dexamethasone, triamcinalone, prednisolone, an inotrope, epinephrine, isoproterenol, a fibrate, clofibrate, gemfibrizole, cyprofibrate, and bezafibrate.

In further embodiments, disclosed herein is the use of one or more compounds or pharmaceutically acceptable salts disclosed herein for ameliorating a perturbation in mitochondrial number, function, or structure induced by a chemical composition administered to a subject.

Figure 1:
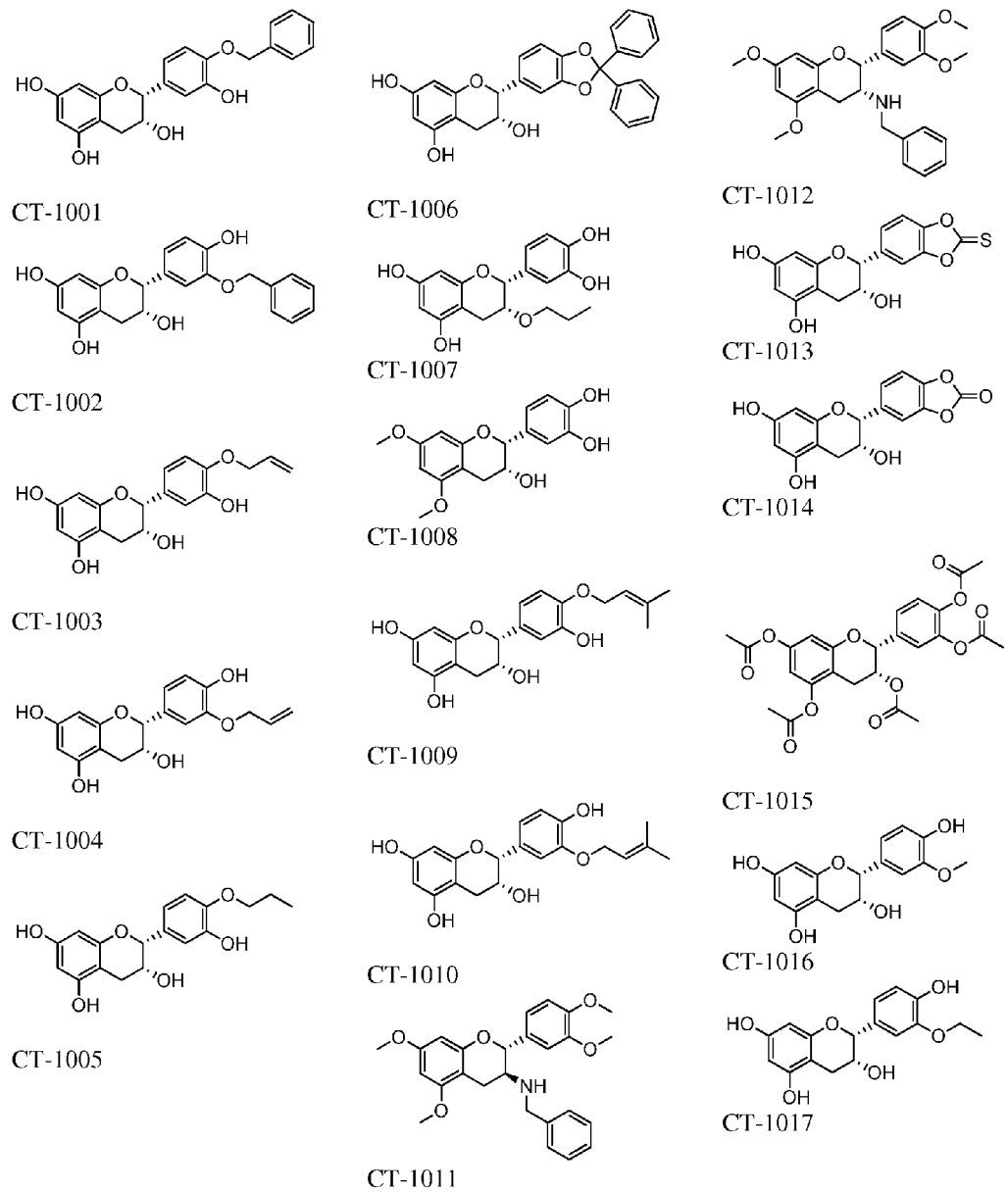
FIG. 1 depicts the structures of certain epicatechin derivatives tested in the assays disclosed herein.

As used herein, the terms below have the meanings indicated.

The term "epicatechin derivative" as used herein refers to any compound which retains the ring structure and 3R(−) stereochemistry of epicatechin itself, but which contains one or more substituent groups relative to epicatechin. Certain naturally occurring epicatechin derivatives are known, such as (−)-epigallocatechin (EGC), (−)-epicatechin-3-gallate (ECG) and (−)-epigallocatechin-3-gallate (EGCG). The term also includes combination molecules or prodrugs which release epicatechin or a derivative thereof when administered to a subject. Such a combination molecule may include, for example, epicatechin and nicorandil joined by a hydrolysable linger group. Similarly, the term "catechin derivative" as used herein refers to any compound which retains the ring structure and 3R(+) stereochemistry of catechin itself, but which contains one or more substituent groups relative to catechin Basic Flavonoid Structure

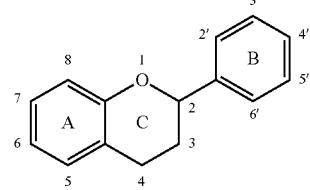

Formula A

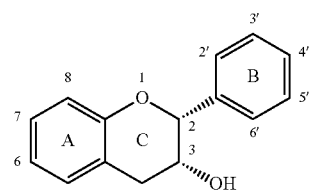

(−)-Epicatechin (2R, 3R)

-continued

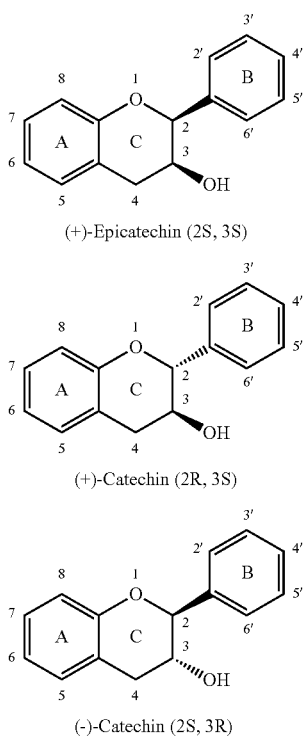

(+)-Epicatechin (2S, 3S)

(+)-Catechin (2R, 3S)

(−)-Catechin (2S, 3R)

Formula A describes the basic flavonoid structure, numbering and ring designation. The flavonoids are further subdivided depending on modification of the C ring. The catechin (or flavan-3-ol) family possesses a 3-hydroxy group. Important members of the catechin family include (+)-catechin which has (2R,3S) stereochemistry and (−)-epicatechin which has (2R,3R) stereochemistry. For purposes of this disclosure, IUPAC nomenclature was typically generated using the Cambridgesoft Struct=Name algorithm in ChemDraw 9.0.1. For example, (−)-epicatechin is named "(2R,3R)-2-(3,4-dihydroxyphenyl)chroman-3,5,7-triol." Similarly, a compound of Formula I:

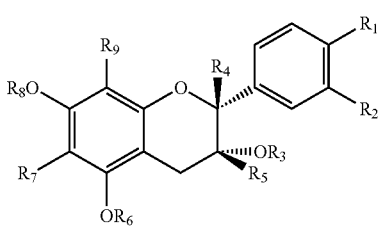

where $R_1$ is —O—$(CH_2)_2CH_3$; $R_2$ and $R_3$ are —OH; and $R_4$, $R_5$, $R_6$, $R_7$, $R_8$ and $R_9$ are —H, is named "(2R,3R)-2-(3-hydroxy-4-propoxyphenyl)chroman-3,5,7-triol." A compound of Formula I where $R_1$ is —C(O)O$CH_3$; $R_2$ is —O$CH_3$; $R_3$ is —OH; and $R_4$, $R_5$, $R_7$, and $R_9$ are —H; and $R_6$ and $R_9$ are —$CH_3$, is named "methyl 4-((2R,3R)-3-hydroxy-5,7-dimethoxychroman-2-yl)-2-methoxybenzoate."

The terms "ischemia," "ischemic," or "ischemic condition" as used herein, refer to a medical event which is pathological in origin, or to a surgical intervention which is imposed on a subject, wherein circulation to a region of the tissue is impeded or blocked, either temporarily, as in vasospasm or transient ischemic attach (TIA) in cerebral ischemia or permanently, as in thrombolic occlusion in cerebral ischemia. The affected region is deprived of oxygen and nutrients as a consequence of the ischemic event. This deprivation leads to the injuries of infarction or in the region affected. The disclosure encompasses cerebral ischemia; intestinal ischemia; spinal cord ischemia; cardiovascular ischemia; peripheral arterial insufficiency and/or other forms of peripheral vascular disease, ischemia associated with chronic heart failure, liver ischemia; kidney ischemia; dermal ischemia; vasoconstriction-induced tissue ischemia, such as a consequence of Raynaud's disorder; penile ischemia as a consequence of priapism; and ischemia associated with thromboembolytic disease; microvascular disease; such as for example diabetes and vasculitis; diabetic ulcers; gangrenous conditions; post-trauma syndrome; cardiac arrest resuscitation; and peripheral nerve damage and neuropathies; and other ischemias, including ischemia associated with ocular health concerns, such as for example, age related macular degeneration (AMD). Ischemia occurs in the brain during, for example, a stroke, cardiac arrest, severe blood loss due to injury or internal hemorrhage and other similar conditions that disrupt normal blood flow. Ischemia occurs in myocardial tissue as a result of, for example, atherosclerosis and chronic heart failure. It may also occur after a trauma to the tissue since the pressure caused by edema presses against and flattens the arteries and veins inside the tissue, thereby reducing their ability to carry blood through the tissue. Cerebral ischemia may also occur as a result of macro- or micro-emboli, such as may occur subsequent to cardiopulmonary bypass surgery. Age-related macular degeneration may be associated with oxidative damage to the retina as a result of an ischemic condition.

The term "non-cardiovascular ischemic condition," as used herein specifically excludes an ischemic condition of the cardio-pulmonary system or circulatory system.

The term "non-cerebral ischemic condition," as used herein specifically excludes an ischemic condition of the brain.

The terms "cerebral ischemia," "cerebral ischemic," or "cerebral ischemic condition," as used herein, refer to a medical event which is pathological in origin, or to a surgical intervention which is imposed on a subject, wherein circulation to a region of the brain is impeded or blocked, either temporarily, as in vasospasm or transient ischemic attach (TIA) or permanently, as in thrombolic occlusion. The affected region is deprived of oxygen and nutrients as a consequence of the ischemic event. This deprivation leads to the injuries of infarction or in the region affected. Ischemia occurs in the brain during, for example, a thromboembolic stroke, hemorrhagic stroke, cerebral vasospasm, head trauma, cardiac arrest, severe blood loss due to injury or internal hemorrhage and other similar conditions that disrupt normal blood flow. It may also occur after a head trauma, since the pressure caused by edema presses against and flattens the arteries and veins inside the brain, thereby reducing their ability to carry blood through the brain. Cerebral ischemia may also occur as a result of macro- or micro-emboli, such as may occur subsequent to cardiopulmonary bypass surgery.

The terms "acute ischemia" or "acute ischemic event," as used herein, refer to an event having a sudden onset, as opposed to a chronic event which is ongoing.

The term "adverse cardiac remodeling," as used herein, refers to the changes in size, shape, and associated function of the heart after injury to the left and right ventricle and/or right and left atrium. The injury is typically due to acute myocardial infarction (such as, for example transmural or ST segment elevation infarction) or induced injury (such as for example, heart surgery), but may be from a number of causes that result in increased pressure or volume overload (forms of strain) on the heart. Cardiac remodeling includes hypertrophy, thinning of the myocardium, scar formation of the myocardium, atrophy of the myocardium, heart failure progression and combinations thereof. Chronic hypertension, Kawasaki's disease, congenital heart disease with intracardiac shunting, and valvular heart disease may lead to remodeling. Additionally remodeling may stem from coronary artery bypass surgery, cardiac transplant and application of a mechanical support device, such as a left ventricular assist device (LVAD).

The term "reduced myocardial infarct size," used herein, refers to a decrease in the size of a myocardial infarct in subjects treated with the compositions of the present invention compared to the size of a myocardial infarct in control subjects receiving no treatment. In the disclosed methods, "reducing" can refer to any one of a 5%, 10%, a 20%, a 30%, a 40%, or even a 50% decrease in myocardial infarct size. Alternately "reducing" can refer to any one of a 60%, 70% or 80% decrease in myocardial infarct size. As is known to those of skill in the art, changes to the myocardium, particularly determination of the size of a myocardial infarct, can be made using imaging techniques such as echocardiography, cardiac MRI, cardiac CT, and cardiac nuclear scans. Additionally, elevation of one or more biomarkers, including troponin, CK-MB (creatine kinase mb), and CPK (creatine phosphokinase), is known to be indicative of dead or dying myocardium. There is also evidence that the biomarker BNP (B-type Naturetic Peptide) can be used as a marker for cardiac remodeling.

The term "favorable cardiac remodeling," as used herein, refers to preservation of chamber size, shape, function and the prevention of ventricular wall thinning and scarring which occurs after injury to the heart.

The terms "atrial fibrillation" and "atrial flutter," as used herein, each refer to an arrhythmia where the atria do not beat effectively in coordination with the ventricle with often an accompanying decrease in cardiac output.

As used herein in reference to heart tissue "induced injury" refers to damaged myocardium, such as damage that results from heart surgery, including but not limited to, coronary artery bypass surgery, cardiac transplant and application of a mechanical support device, such as a left ventricular assist device (LVAD).

When ranges of values are disclosed, and the notation "from $n_1 \ldots$ to $n_2$" or "between $n_1 \ldots$ and $n_2$" is used, where $n_1$ and $n_2$ are the numbers, then unless otherwise specified, this notation is intended to include the numbers themselves and the range between them. This range may be integral or continuous between and including the end values. By way of example, the range "from 2 to 6 carbons" is intended to include two, three, four, five, and six carbons, since carbons come in integer units. Compare, by way of example, the range "from 1 to 3 μM (micromolar)," which is intended to include 1 μM, 3 μM, and everything in between to any number of significant figures (e.g., 1.255 μM, 2.1 μM, 2.9999 μM, etc.).

The term "about," as used herein, is intended to qualify the numerical values which it modifies, denoting such a value as variable within a margin of error. When no particular margin of error, such as a standard deviation to a mean value given in a chart or table of data, is recited, the term "about" should be understood to mean that range which would encompass the recited value and the range which would be included by rounding up or down to that figure as well, taking into account significant figures.

The term "acyl," as used herein, alone or in combination, refers to a carbonyl attached to an alkenyl, alkyl, aryl, cycloalkyl, heteroaryl, heterocycle, or any other moiety were the atom attached to the carbonyl is carbon. An "acetyl" group refers to a —C(O)CH$_3$ group. An "alkylcarbonyl" or "alkanoyl" group refers to an alkyl group attached to the parent molecular moiety through a carbonyl group. Examples of such groups include methylcarbonyl and ethylcarbonyl. Examples of acyl groups include formyl, alkanoyl and aroyl.

The term "alkenyl," as used herein, alone or in combination, refers to a straight-chain or branched-chain hydrocarbon radical having one or more double bonds and containing from 2 to 20 carbon atoms. In certain embodiments, said alkenyl will comprise from 2 to 6 carbon atoms. The term "alkenylene" refers to a carbon-carbon double bond system attached at two or more positions such as ethenylene [(—CH═CH—),(—C::C—)]. Examples of suitable alkenyl radicals include ethenyl, propenyl, 2-methylpropenyl, 1,4-butadienyl and the like. Unless otherwise specified, the term "alkenyl" may include "alkenylene" groups.

The term "alkoxy," as used herein, alone or in combination, refers to an alkyl ether radical, wherein the term alkyl is as defined below. Examples of suitable alkyl ether radicals include methoxy, ethoxy, n-propoxy, isopropoxy, n-butoxy, iso-butoxy, sec-butoxy, tert-butoxy, and the like.

The term "alkyl," as used herein, alone or in combination, refers to a straight-chain or branched-chain alkyl radical containing from 1 to 20 carbon atoms. In certain embodiments, said alkyl will comprise from 1 to 10 carbon atoms. In further embodiments, said alkyl will comprise from 1 to 6 carbon atoms. Alkyl groups may be optionally substituted as defined herein. Examples of alkyl radicals include methyl, ethyl, n-propyl, isopropyl, n-butyl, isobutyl, sec-butyl, tert-butyl, pentyl, iso-amyl, hexyl, octyl, noyl and the like. The term "alkylene," as used herein, alone or in combination, refers to a saturated aliphatic group derived from a straight or branched chain saturated hydrocarbon attached at two or more positions, such as methylene (—CH$_2$—). Unless otherwise specified, the term "alkyl" may include "alkylene" groups.

The term "alkylamino," as used herein, alone or in combination, refers to an alkyl group attached to the parent molecular moiety through an amino group. Suitable alkylamino groups may be mono- or dialkylated, forming groups such as, for example, N-methylamino, N-ethylamino, N,N-dimethylamino, N,N-ethylmethylamino and the like.

The term "alkylidene," as used herein, alone or in combination, refers to an alkenyl group in which one carbon atom of the carbon-carbon double bond belongs to the moiety to which the alkenyl group is attached.

The term "alkylthio," as used herein, alone or in combination, refers to an alkyl thioether (R—S—) radical wherein the term alkyl is as defined above and wherein the sulfur may be singly or doubly oxidized. Examples of suitable alkyl thioether radicals include methylthio, ethylthio, n-propylthio, isopropylthio, n-butylthio, iso-butylthio, sec-butylthio, tert-butylthio, methanesulfonyl, ethanesulfinyl, and the like.

The term "alkynyl," as used herein, alone or in combination, refers to a straight-chain or branched chain hydrocarbon radical having one or more triple bonds and containing from 2 to 20 carbon atoms. In certain embodiments, said alkynyl comprises from 2 to 6 carbon atoms. In further embodiments, said alkynyl comprises from 2 to 4 carbon atoms. The term "alkynylene" refers to a carbon-carbon triple bond attached at two positions such as ethynylene (—C:::C—, —C≡C—). Examples of alkynyl radicals include ethynyl, propynyl, hydroxypropynyl, butyn-1-yl, butyn-2-yl, pentyn-1-yl, 3-methylbutyn-1-yl, hexyn-2-yl, and the like. Unless otherwise specified, the term "alkynyl" may include "alkynylene" groups.

The terms "amido" and "carbamoyl," as used herein, alone or in combination, refer to an amino group as described below attached to the parent molecular moiety through a carbonyl group, or vice versa. The term "C-amido" as used herein, alone or in combination, refers to a —C(O)N(RR') group with R and R' as defined herein or as defined by the specifically enumerated "R" groups designated. The term "N-amido" as used herein, alone or in combination, refers to a RC(O)N(R')— group, with R and R' as defined herein or as defined by the specifically enumerated "R" groups designated. The term "acylamino" as used herein, alone or in combination, embraces an acyl group attached to the parent moiety through an amino group. An example of an "acylamino" group is acetylamino ($CH_3C(O)NH$—).

The term "amino," as used herein, alone or in combination, refers to —NRR', wherein R and R' are independently selected from the group consisting of hydrogen, alkyl, acyl, heteroalkyl, aryl, cycloalkyl, heteroaryl, and heterocycloalkyl, any of which may themselves be optionally substituted. Additionally, R and R' may combine to form heterocycloalkyl, either of which may be optionally substituted.

The term "aryl," as used herein, alone or in combination, means a carbocyclic aromatic system containing one, two or three rings wherein such polycyclic ring systems are fused together. The term "aryl" embraces aromatic groups such as phenyl, naphthyl, anthracenyl, and phenanthryl.

The term "arylalkenyl" or "aralkenyl," as used herein, alone or in combination, refers to an aryl group attached to the parent molecular moiety through an alkenyl group.

The term "arylalkoxy" or "aralkoxy," as used herein, alone or in combination, refers to an aryl group attached to the parent molecular moiety through an alkoxy group.

The term "arylalkyl" or "aralkyl," as used herein, alone or in combination, refers to an aryl group attached to the parent molecular moiety through an alkyl group.

The term "arylalkynyl" or "aralkynyl," as used herein, alone or in combination, refers to an aryl group attached to the parent molecular moiety through an alkynyl group.

The term "arylalkanoyl" or "aralkanoyl" or "aroyl," as used herein, alone or in combination, refers to an acyl radical derived from an aryl-substituted alkanecarboxylic acid such as benzoyl, napthoyl, phenylacetyl, 3-phenylpropionyl (hydrocinnamoyl), 4-phenylbutyryl, (2-naphthyl)acetyl, 4-chlorohydrocinnamoyl, and the like.

The term aryloxy as used herein, alone or in combination, refers to an aryl group attached to the parent molecular moiety through an oxy.

The terms "benzo" and "benz," as used herein, alone or in combination, refer to the divalent radical $C_6H_4$= derived from benzene. Examples include benzothiophene and benzimidazole.

The term "carbamate," as used herein, alone or in combination, refers to an ester of carbamic acid (—NHCOO—) which may be attached to the parent molecular moiety from either the nitrogen or acid end, and which may be optionally substituted as defined herein.

The term "O-carbamyl" as used herein, alone or in combination, refers to a —OC(O)NRR', group-with R and R' as defined herein.

The term "N-carbamyl" as used herein, alone or in combination, refers to a ROC(O)NR'— group, with R and R' as defined herein.

The term "carbonyl," as used herein, when alone includes formyl [—C(O)H] and in combination is a —C(O)— group.

The term "carboxyl" or "carboxy," as used herein, refers to —C(O)OH or the corresponding "carboxylate" anion, such as is in a carboxylic acid salt. An "O-carboxy" group refers to a RC(O)O— group, where R is as defined herein. A "C-carboxy" group refers to a —C(O)OR groups where R is as defined herein.

The term "cyano," as used herein, alone or in combination, refers to —CN.

The term "cycloalkyl," or, alternatively, "carbocycle," as used herein, alone or in combination, refers to a saturated or partially saturated monocyclic, bicyclic or tricyclic alkyl group wherein each cyclic moiety contains from 3 to 12 carbon atom ring members and which may optionally be a benzo fused ring system which is optionally substituted as defined herein. In certain embodiments, said cycloalkyl will comprise from 5 to 7 carbon atoms. Examples of such cycloalkyl groups include cyclopropyl, cyclobutyl, cyclopentyl, cyclohexyl, cycloheptyl, tetrahydronapthyl, indanyl, octahydronaphthyl, 2,3-dihydro-1H-indenyl, adamantyl and the like. "Bicyclic" and "tricyclic" as used herein are intended to include both fused ring systems, such as decahydronaphthalene, octahydronaphthalene as well as the multicyclic (multicentered) saturated or partially unsaturated type. The latter type of isomer is exemplified in general by, bicyclo[1,1,1]pentane, camphor, adamantane, and bicyclo[3,2,1]octane.

The term "ester," as used herein, alone or in combination, refers to a carboxy group bridging two moieties linked at carbon atoms.

The term "ether," as used herein, alone or in combination, refers to an oxy group bridging two moieties linked at carbon atoms.

The term "halo," or "halogen," as used herein, alone or in combination, refers to fluorine, chlorine, bromine, or iodine.

The term "haloalkoxy," as used herein, alone or in combination, refers to a haloalkyl group attached to the parent molecular moiety through an oxygen atom.

The term "haloalkyl," as used herein, alone or in combination, refers to an alkyl radical having the meaning as defined above wherein one or more hydrogens are replaced with a halogen. Specifically embraced are monohaloalkyl, dihaloalkyl and polyhaloalkyl radicals. A monohaloalkyl radical, for one example, may have an iodo, bromo, chloro or fluoro atom within the radical. Dihalo and polyhaloalkyl radicals may have two or more of the same halo atoms or a combination of different halo radicals. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Haloalkylene" refers to a haloalkyl group attached at two or more positions. Examples include fluoromethylene (—CFH—), difluoromethylene (—$CF_2$—), chloromethylene (—CHCl—) and the like.

The term "heteroalkyl," as used herein, alone or in combination, refers to a stable straight or branched chain, or cyclic hydrocarbon radical, or combinations thereof, fully saturated or containing from 1 to 3 degrees of unsaturation, consisting of the stated number of carbon atoms and from one to three heteroatoms selected from the group consisting of O, N, and S, and wherein the nitrogen and sulfur atoms may optionally be oxidized and the nitrogen heteroatom may optionally be quaternized. The heteroatom(s) O, N and S may be placed at any interior position of the heteroalkyl group. Up to two heteroatoms may be consecutive, such as, for example, —$CH_2$—NH—$OCH_3$.

The term "heteroaryl," as used herein, alone or in combination, refers to a 3 to 15 membered unsaturated heteromonocyclic ring, or a fused monocyclic, bicyclic, or tricyclic ring system in which at least one of the fused rings is aromatic, which contains at least one atom selected from the group consisting of O, S, and N. In certain embodiments, said heteroaryl will comprise from 5 to 7 carbon atoms. The term also embraces fused polycyclic groups wherein heterocyclic rings are fused with aryl rings, wherein heteroaryl rings are fused with other heteroaryl rings, wherein heteroaryl rings are fused with heterocycloalkyl rings, or wherein heteroaryl rings are fused with cycloalkyl rings. Examples of heteroaryl groups include pyrrolyl, pyrrolinyl, imidazolyl, pyrazolyl, pyridyl, pyrimidinyl, pyrazinyl, pyridazinyl, triazolyl, pyranyl, furyl, thienyl, oxazolyl, isoxazolyl, oxadiazolyl, thiazolyl, thiadiazolyl, isothiazolyl, indolyl, isoindolyl, indolizinyl, benzimidazolyl, quinolyl, isoquinolyl, quinoxalinyl, quinazolinyl, indazolyl, benzotriazolyl, benzodioxolyl, benzopyranyl, benzoxazolyl, benzoxadiazolyl, benzothiazolyl, benzothiadiazolyl, benzofuryl, benzothienyl, chromonyl, coumarinyl, benzopyranyl, tetrahydroquinolinyl, tetrazolopyridazinyl, tetrahydroisoquinolinyl, thienopyridinyl, furopyridinyl, pyrrolopyridinyl and the like. Exemplary tricyclic heterocyclic groups include carbazolyl, benzidolyl, phenanthrolinyl, dibenzofuranyl, acridinyl, phenanthridinyl, xanthenyl and the like.

The terms "heterocycloalkyl" and, interchangeably, "heterocycle," as used herein, alone or in combination, each refer to a saturated, partially unsaturated, or fully unsaturated monocyclic, bicyclic, or tricyclic heterocyclic group containing at least one heteroatom as a ring member, wherein each said heteroatom may be independently selected from the group consisting of nitrogen, oxygen, and sulfur In certain embodiments, said heterocycloalkyl will comprise from 1 to 4 heteroatoms as ring members. In further embodiments, said heterocycloalkyl will comprise from 1 to 2 heteroatoms as ring members. In certain embodiments, said heterocycloalkyl will comprise from 3 to 8 ring members in each ring. In further embodiments, said heterocycloalkyl will comprise from 3 to 7 ring members in each ring. In yet further embodiments, said heterocycloalkyl will comprise from 5 to 6 ring members in each ring. "Heterocycloalkyl" and "heterocycle" are intended to include sulfones, sulfoxides, N-oxides of tertiary nitrogen ring members, and carbocyclic fused and benzo fused ring systems; additionally, both terms also include systems where a heterocycle ring is fused to an aryl group, as defined herein, or an additional heterocycle group. Examples of heterocycle groups include aziridinyl, azetidinyl, 1,3-benzodioxolyl, dihydroisoindolyl, dihydroisoquinolinyl, dihydrocinnolinyl, dihydrobenzodioxinyl, dihydro[1,3]oxazolo[4,5-b]pyridinyl, benzothiazolyl, dihydroindolyl, dihydropyridinyl, 1,3-dioxanyl, 1,4-dioxanyl, 1,3-dioxolanyl, isoindolinyl, morpholinyl, piperazinyl, pyrrolidinyl, tetrahydropyridinyl, piperidinyl, thiomorpholinyl, and the like. The heterocycle groups may be optionally substituted unless specifically prohibited.

The term "hydrazinyl" as used herein, alone or in combination, refers to two amino groups joined by a single bond, i.e., —N—N—.

The term "hydroxy," as used herein, alone or in combination, refers to —OH.

The term "hydroxyalkyl," as used herein, alone or in combination, refers to a hydroxy group attached to the parent molecular moiety through an alkyl group.

The term "imino," as used herein, alone or in combination, refers to =N—.

The term "iminohydroxy," as used herein, alone or in combination, refers to =N(OH) and =N—O—.

The phrase "in the main chain" refers to the longest contiguous or adjacent chain of carbon atoms starting at the point of attachment of a group to the compounds of any one of the formulas disclosed herein.

The term "isocyanato" refers to a —NCO group.

The term "isothiocyanato" refers to a —NCS group.

The phrase "linear chain of atoms" refers to the longest straight chain of atoms independently selected from carbon, nitrogen, oxygen and sulfur.

The term "lower," as used herein, alone or in a combination, where not otherwise specifically defined, means containing from 1 to and including 6 carbon atoms.

The term "lower aryl," as used herein, alone or in combination, means phenyl or naphthyl, either of which may be optionally substituted as provided.

The term "lower heteroaryl," as used herein, alone or in combination, means either 1) monocyclic heteroaryl comprising five or six ring members, of which between one and four said members may be heteroatoms selected from the group consisting of O, S, and N, or 2) bicyclic heteroaryl, wherein each of the fused rings comprises five or six ring members, comprising between them one to four heteroatoms selected from the group consisting of O, S, and N.

The term "lower cycloalkyl," as used herein, alone or in combination, means a monocyclic cycloalkyl having between three and six ring members. Lower cycloalkyls may be unsaturated. Examples of lower cycloalkyl include cyclopropyl, cyclobutyl, cyclopentyl, and cyclohexyl.

The term "lower heterocycloalkyl," as used herein, alone or in combination, means a monocyclic heterocycloalkyl having between three and six ring members, of which between one and four may be heteroatoms selected from the group consisting of O, S, and N. Examples of lower heterocycloalkyls include pyrrolidinyl, imidazolidinyl, pyrazolidinyl, piperidinyl, piperazinyl, and morpholinyl. Lower heterocycloalkyls may be unsaturated.

The term "lower amino," as used herein, alone or in combination, refers to —NRR', wherein R and R' are independently selected from the group consisting of hydrogen, lower alkyl, and lower heteroalkyl, any of which may be optionally substituted. Additionally, the R and R' of a lower amino group may combine to form a five- or six-membered heterocycloalkyl, either of which may be optionally substituted.

The term "mercaptyl" as used herein, alone or in combination, refers to an RS— group, where R is as defined herein.

The term "nitro," as used herein, alone or in combination, refers to —NO$_2$.

The terms "oxy" or "oxa," as used herein, alone or in combination, refer to —O—.

The term "oxo," as used herein, alone or in combination, refers to =O.

The term "perhaloalkoxy" refers to an alkoxy group where all of the hydrogen atoms are replaced by halogen atoms.

The term "perhaloalkyl" as used herein, alone or in combination, refers to an alkyl group where all of the hydrogen atoms are replaced by halogen atoms.

The terms "sulfonate," "sulfonic acid," and "sulfonic," as used herein, alone or in combination, refer the —SO$_3$H group and its anion as the sulfonic acid is used in salt formation.

The term "sulfanyl," as used herein, alone or in combination, refers to —S—.

The term "sulfinyl," as used herein, alone or in combination, refers to —S(O)—.

The term "sulfonyl," as used herein, alone or in combination, refers to —S(O)$_2$—.

The term "N-sulfonamido" refers to a RS(=O)₂NR'— group with R and R' as defined herein.

The term "S-sulfonamido" refers to a —S(=O)₂NRR', group, with R and R' as defined herein.

The terms "thia" and "thio," as used herein, alone or in combination, refer to a —S— group or an ether wherein the oxygen is replaced with sulfur. The oxidized derivatives of the thio group, namely sulfinyl and sulfonyl, are included in the definition of thia and thio.

The term "thiol," as used herein, alone or in combination, refers to an —SH group.

The term "thiocarbonyl," as used herein, when alone includes thioformyl —C(S)H and in combination is a —C(S)— group.

The term "N-thiocarbamyl" refers to an ROC(S)NR'— group, with R and R' as defined herein.

The term "O-thiocarbamyl" refers to a —OC(S)NRR', group with R and R' as defined herein.

The term "thiocyanato" refers to a —CNS group.

The term "trihalomethanesulfonamido" refers to a X₃CS(O)₂NR— group with X is a halogen and R as defined herein.

The term "trihalomethanesulfonyl" refers to a X₃CS(O)₂— group where X is a halogen.

The term "trihalomethoxy" refers to a X₃CO— group where X is a halogen.

The term "trisubstituted silyl," as used herein, alone or in combination, refers to a silicone group substituted at its three free valences with groups as listed herein under the definition of substituted amino. Examples include trimethysilyl, tert-butyldimethylsilyl, triphenylsilyl and the like.

Any definition herein may be used in combination with any other definition to describe a composite structural group. By convention, the trailing element of any such definition is that which attaches to the parent moiety. For example, the composite group alkylamido would represent an alkyl group attached to the parent molecule through an amido group, and the term alkoxyalkyl would represent an alkoxy group attached to the parent molecule through an alkyl group.

When a group is defined to be "null," what is meant is that said group is absent.

The term "optionally substituted" means the anteceding group may be substituted or unsubstituted. When substituted, the substituents of an "optionally substituted" group may include, without limitation, one or more substituents independently selected from the following groups or a particular designated set of groups, alone or in combination: lower alkyl, lower alkenyl, lower alkynyl, lower alkanoyl, lower heteroalkyl, lower heterocycloalkyl, lower haloalkyl, lower haloalkenyl, lower haloalkynyl, lower perhaloalkyl, lower perhaloalkoxy, lower cycloalkyl, phenyl, aryl, aryloxy, lower alkoxy, lower haloalkoxy, oxo, lower acyloxy, carbonyl, carboxyl, lower alkylcarbonyl, lower carboxyester, lower carboxamido, cyano, hydrogen, halogen, hydroxy, amino, lower alkylamino, arylamino, amido, nitro, thiol, lower alkylthio, lower haloalkylthio, lower perhaloalkylthio, arylthio, sulfonate, sulfonic acid, trisubstituted silyl, $N_3$, SH, $SCH_3$, $C(O)CH_3$, $CO_2CH_3$, $CO_2H$, pyridinyl, thiophene, furanyl, lower carbamate, and lower urea. Two substituents may be joined together to form a fused five-, six-, or seven-membered carbocyclic or heterocyclic ring consisting of zero to three heteroatoms, for example forming methylenedioxy or ethylenedioxy. An optionally substituted group may be unsubstituted (e.g., —$CH_2CH_3$), fully substituted (e.g., —$CF_2CF_3$), mono-substituted (e.g., —$CH_2CH_2F$) or substituted at a level anywhere in-between fully substituted and monosubstituted (e.g., —$CH_2CF_3$). Where substituents are recited without qualification as to substitution, both substituted and unsubstituted forms are encompassed. Where a substituent is qualified as "substituted," the substituted form is specifically intended. Additionally, different sets of optional substituents to a particular moiety may be defined as needed; in these cases, the optional substitution will be as defined, often immediately following the phrase, "optionally substituted with."

The term R or the term R', appearing by itself and without a number designation, unless otherwise defined, refers to a moiety selected from the group consisting of hydrogen, alkyl, cycloalkyl, heteroalkyl, aryl, heteroaryl and heterocycloalkyl, any of which may be optionally substituted. Such R and R' groups should be understood to be optionally substituted as defined herein. Whether an R group has a number designation or not, every R group, including R, R' and R" where n=(1, 2, 3, . . . n), every substituent, and every term should be understood to be independent of every other in terms of selection from a group. Should any variable, substituent, or term (e.g. aryl, heterocycle, R, etc.) occur more than one time in a formula or generic structure, its definition at each occurrence is independent of the definition at every other occurrence. Those of skill in the art will further recognize that certain groups may be attached to a parent molecule or may occupy a position in a chain of elements from either end as written. Thus, by way of example only, an unsymmetrical group such as —C(O)N(R)— may be attached to the parent moiety at either the carbon or the nitrogen.

Asymmetric centers exist in the compounds disclosed herein. These centers are designated by the symbols "R" or "S," depending on the configuration of substituents around the chiral carbon atom. It should be understood that the invention encompasses all stereochemical isomeric forms, including diastereomeric, enantiomeric, and epimeric forms, as well as d-isomers and 1-isomers, and mixtures thereof. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. Starting compounds of particular stereochemistry are either commercially available or can be made and resolved by techniques known in the art. Additionally, the compounds disclosed herein may exist as geometric isomers. The present invention includes all cis, trans, syn, anti, entgegen (E), and zusammen (Z) isomers as well as the appropriate mixtures thereof. Additionally, compounds may exist as tautomers; all tautomeric isomers are provided by this invention. Additionally, the compounds disclosed herein can exist in unsolvated as well as solvated forms with pharmaceutically acceptable solvents such as water, ethanol, and the like. In general, the solvated forms are considered equivalent to the unsolvated forms.

The term "bond" refers to a covalent linkage between two atoms, or two moieties when the atoms joined by the bond are considered to be part of larger substructure. A bond may be single, double, or triple unless otherwise specified. A dashed line between two atoms in a drawing of a molecule indicates that an additional bond may be present or absent at that position.

The term "disease" as used herein is intended to be generally synonymous, and is used interchangeably with, the terms "disorder," "syndrome," and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

The term "combination therapy" means the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner. In either case, the treatment regimen will provide beneficial effects of the drug combination in treating the conditions or disorders described herein.

The term "mitochondrial activity modulator" is used herein to refer to a compound that exhibits an effective concentration with respect to increased mitochondrial activity of no more than about 100 µM and more typically not more than about 50 µM, as measured in the assays described generally hereinbelow.

The phrase "therapeutically effective" is intended to qualify the amount of active ingredients used in the treatment of a disease or disorder or on the effecting of a clinical endpoint.

The term "therapeutically acceptable" refers to those compounds (or salts, prodrugs, tautomers, zwitterionic forms, etc.) which are suitable for use in contact with the tissues of patients without undue toxicity, irritation, and allergic response, are commensurate with a reasonable benefit/risk ratio, and are effective for their intended use.

As used herein, reference to "treatment" of a patient is intended to include prophylaxis. Treatment may also be pre-emptive in nature, i.e., it may include prevention of disease. Prevention of a disease may involve complete protection from disease, for example as in the case of prevention of infection with a pathogen, or may involve prevention of disease progression. For example, prevention of a disease may not mean complete foreclosure of any effect related to the diseases at any level, but instead may mean prevention of the symptoms of a disease to a clinically significant or detectable level. Prevention of diseases may also mean prevention of progression of a disease to a later stage of the disease.

The term "patient" is generally synonymous with the term "subject" and includes all mammals including humans. Examples of patients include humans, livestock such as cows, goats, sheep, pigs, and rabbits, and companion animals such as dogs, cats, rabbits, and horses. Preferably, the patient is a human.

The term "prodrug" refers to a compound that is made more active in vivo. Certain compounds disclosed herein may also exist as prodrugs, as described in *Hydrolysis in Drug and Prodrug Metabolism: Chemistry, Biochemistry, and Enzymology* (Testa, Bernard and Mayer, Joachim M. Wiley-VHCA, Zurich, Switzerland 2003). Prodrugs of the compounds described herein are structurally modified forms of the compound that readily undergo chemical changes under physiological conditions to provide the compound. Additionally, prodrugs can be converted to the compound by chemical or biochemical methods in an ex vivo environment. For example, prodrugs can be slowly converted to a compound when placed in a transdermal patch reservoir with a suitable enzyme or chemical reagent. Prodrugs are often useful because, in some situations, they may be easier to administer than the compound, or parent drug. They may, for instance, be bioavailable by oral administration whereas the parent drug is not. The prodrug may also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug would be a compound which is administered as a ester (the "prodrug"), but then is metabolically hydrolyzed to the carboxylic acid, the active entity. Additional examples include peptidyl derivatives of a compound.

The compounds disclosed herein can exist as therapeutically acceptable salts. The present invention includes compounds listed above in the form of salts, including acid addition salts. Suitable salts include those formed with both organic and inorganic acids. Such acid addition salts will normally be pharmaceutically acceptable. However, salts of non-pharmaceutically acceptable salts may be of utility in the preparation and purification of the compound in question. Basic addition salts may also be formed and be pharmaceutically acceptable. For a more complete discussion of the preparation and selection of salts, refer to *Pharmaceutical Salts Properties, Selection, and Use* (Stahl, P. Heinrich. Wiley-VCHA, Zurich, Switzerland, 2002).

The term "therapeutically acceptable salt," as used herein, represents salts or zwitterionic forms of the compounds disclosed herein which are water or oil-soluble or dispersible and therapeutically acceptable as defined herein. The salts can be prepared during the final isolation and purification of the compounds or separately by reacting the appropriate compound in the form of the free base with a suitable acid. Representative acid addition salts include acetate, adipate, alginate, L-ascorbate, aspartate, benzoate, benzenesulfonate (besylate), bisulfate, butyrate, camphorate, camphorsulfonate, citrate, digluconate, formate, fumarate, gentisate, glutarate, glycerophosphate, glycolate, hemisulfate, heptanoate, hexanoate, hippurate, hydrochloride, hydrobromide, hydroiodide, 2-hydroxyethansulfonate (isethionate), lactate, maleate, malonate, DL-mandelate, mesitylenesulfonate, methanesulfonate, naphthylenesulfonate, nicotinate, 2-naphthalenesulfonate, oxalate, pamoate, pectinate, persulfate, 3-phenylproprionate, phosphonate, picrate, pivalate, propionate, pyroglutamate, succinate, sulfonate, tartrate, L-tartrate, trichloroacetate, trifluoroacetate, phosphate, glutamate, bicarbonate, para-toluenesulfonate (p-tosylate), and undecanoate. Also, basic groups in the compounds disclosed herein can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric. Salts can also be formed by coordination of the compounds with an alkali metal or alkaline earth ion. Hence, the present invention contemplates sodium, potassium, magnesium, and calcium salts of the compounds disclosed herein, and the like.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of therapeutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N-dibenzylethylenediamine. Other representative organic amines useful for the formation of base addition salts include ethylenediamine, ethanolamine, diethanolamine, piperidine, and piperazine.

A salt of a compound can be made by reacting the appropriate compound in the form of the free base with the appropriate acid.

While it may be possible for the compounds of the subject invention to be administered as the raw chemical, it is also possible to present them as a pharmaceutical formulation. Accordingly, provided herein are pharmaceutical formulations which comprise one or more of certain compounds disclosed herein, or one or more pharmaceutically acceptable salts, esters, prodrugs, amides, or solvates thereof, together with one or more pharmaceutically acceptable carriers thereof and optionally one or more other therapeutic ingredients. The carrier(s) must be "acceptable" in the sense of being compatible with the other ingredients of the formulation and not deleterious to the recipient thereof. Proper formulation is dependent upon the route of administration chosen. Any of the well-known techniques, carriers, and excipients may be used as suitable and as understood in the art; e.g., in Remington's Pharmaceutical Sciences. The pharmaceutical compositions disclosed herein may be manufactured in any manner known in the art, e.g., by means of conventional mixing, dissolving, granulating, dragee-making, levigating, emulsifying, encapsulating, entrapping or compression processes.

The formulations include those suitable for oral, parenteral (including subcutaneous, intradermal, intramuscular, intravenous, intraarticular, and intramedullary), intraperitoneal, transmucosal, transdermal, rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. Typically, these methods include the step of bringing into association a compound of the subject invention or a pharmaceutically acceptable salt, ester, amide, prodrug or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the compounds disclosed herein suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

Pharmaceutical preparations which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. The tablets may optionally be coated or scored and may be formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The formulations may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Formulations for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

The compounds may also be formulated in rectal compositions such as suppositories or retention enemas, e.g., containing conventional suppository bases such as cocoa butter, polyethylene glycol, or other glycerides.

Certain compounds disclosed herein may be administered topically, that is by non-systemic administration. This includes the application of a compound disclosed herein externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as gels, liniments, lotions, creams, ointments or pastes, and drops suitable for administration to the eye, ear or nose. The active ingredient for topical administration may comprise, for example, from 0.001% to 10% w/w (by weight) of the formulation. In certain embodiments, the active ingredient may comprise as much as 10% w/w. In other embodiments, it may comprise less than 5% w/w. In certain embodiments, the active ingredient may comprise from 2% w/w to 5% w/w. In other embodiments, it may comprise from 0.1% to 1% w/w of the formulation.

Formulations for topical administration in the mouth, for example buccally or sublingually, include lozenges comprising the active ingredient in a flavored basis such as sucrose and acacia or tragacanth, and pastilles comprising the active ingredient in a basis such as gelatin and glycerin or sucrose and acacia.

For administration by inhalation, compounds may be conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, the compounds according to the invention may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

Preferred unit dosage formulations are those containing an effective dose, as herein below recited, or an appropriate fraction thereof, of the active ingredient.

It should be understood that in addition to the ingredients particularly mentioned above, the formulations described above may include other agents conventional in the art having regard to the type of formulation in question, for example those suitable for oral administration may include flavoring agents.

The compositions of the present invention may also be formulated as nutraceutical compositions. The term "nutraceutical composition" as used herein refers to a food product, foodstuff, dietary supplement, nutritional supplement or a supplement composition for a food product or a foodstuff comprising exogenously added catechin and/or epicatechin Details on techniques for formulation and administration of such compositions may be found in Remington, The Science and Practice of Pharmacy 21st Edition (Mack Publishing Co., Easton, Pa.) and Nielloud and Marti-Mestres, Pharmaceutical Emulsions and Suspensions: 2nd Edition (Marcel Dekker, Inc, New York).

As used herein, the term food product refers to any food or feed suitable for consumption by humans or animals. The food product may be a prepared and packaged food (e.g., mayonnaise, salad dressing, bread, grain bar, beverage, etc.) or an animal feed (e.g., extruded and pelleted animal feed, coarse mixed feed or pet food composition). As used herein, the term foodstuff refers to any substance fit for human or animal consumption. Food products or foodstuffs are for example beverages such as nonalcoholic and alcoholic drinks as well as liquid preparation to be added to drinking water and liquid food, non-alcoholic drinks are for instance soft drinks, sport drinks, fruit juices, such as for example orange juice, apple juice and grapefruit juice; lemonades, teas, near-water drinks and milk and other dairy drinks such as for example yoghurt drinks, and diet drinks. In another embodiment food products or foodstuffs refer to solid or semi-solid foods comprising the composition according to the invention. These forms can include, but are not limited to baked goods such as cakes and cookies, puddings, dairy products, confections, snack foods, or frozen confections or novelties (e.g., ice cream, milk shakes), prepared frozen meals, candy, snack products (e.g., chips), liquid food such as soups, spreads, sauces, salad dressings, prepared meat products, cheese, yogurt and any other fat or oil containing foods, and food ingredients (e.g., wheat flour).

Animal feed including pet food compositions advantageously include food intended to supply necessary dietary requirements, as well as treats (e.g., dog biscuits) or other food supplements. The animal feed comprising the composition according to the invention may be in the form of a dry composition (for example, kibble), semi-moist composition, wet composition, or any mixture thereof. Alternatively or additionally, the animal feed is a supplement, such as a gravy, drinking water, yogurt, powder, suspension, chew, treat (e.g., biscuits) or any other delivery form.

The term dietary supplement refers to a small amount of a compound for supplementation of a human or animal diet packaged in single or multiple dose units. Dietary supplements do not generally provide significant amounts of calories but may contain other micronutrients (e.g., vitamins or minerals). The term food products or foodstuffs also includes functional foods and prepared food products pre-packaged for human consumption.

The term nutritional supplement refers to a composition comprising a dietary supplement in combination with a source of calories. In some embodiments, nutritional supplements are meal replacements or supplements (e.g., nutrient or energy bars or nutrient beverages or concentrates).

Dietary supplements of the present invention may be delivered in any suitable format. In preferred embodiments, dietary supplements are formulated for oral delivery. The ingredients of the dietary supplement of this invention are contained in acceptable excipients and/or carriers for oral consumption. The actual form of the carrier, and thus, the dietary supplement itself, is not critical. The carrier may be a liquid, gel, gelcap, capsule, powder, solid tablet (coated or non-coated), tea, or the like. The dietary supplement is preferably in the form of a tablet or capsule and most preferably in the form of a hard (shell) capsule. Suitable excipient and/or carriers include maltodextrin, calcium carbonate, dicalcium phosphate, tricalcium phosphate, microcrystalline cellulose, dextrose, rice flour, magnesium stearate, stearic acid, croscarmellose sodium, sodium starch glycolate, crospovidone, sucrose, vegetable gums, lactose, methylcellulose, povidone, carboxymethylcellulose, corn starch, and the like (including mixtures thereof). Preferred carriers include calcium carbonate, magnesium stearate, maltodextrin, and mixtures thereof.

The various ingredients and the excipient and/or carrier are mixed and formed into the desired form using conventional techniques. The tablet or capsule of the present invention may be coated with an enteric coating that dissolves at a pH of about 6.0 to 7.0. A suitable enteric coating that dissolves in the small intestine but not in the stomach is cellulose acetate phthalate.

In other embodiments, the dietary supplement is provided as a powder or liquid suitable for adding by the consumer to a food or beverage. For example, in some embodiments, the dietary supplement can be administered to an individual in the form of a powder, for instance to be used by mixing into a beverage, or by stirring into a semisolid food such as a pudding, topping, sauce, puree, cooked cereal, or salad dressing, for instance, or by otherwise adding to a food or the dietary supplement e.g. enclosed in caps of food or beverage container for release immediately before consumption. The dietary supplement may comprise one or more inert ingredients, especially if it is desirable to limit the number of calories added to the diet by the dietary supplement. For example, the dietary supplement of the present invention may also contain optional ingredients including, for example, herbs, vitamins, minerals, enhancers, colorants, sweeteners, flavorants, inert ingredients, and the like.

In some embodiments, the dietary supplements further comprise vitamins and minerals including, but not limited to, calcium phosphate or acetate, tribasic; potassium phosphate, dibasic; magnesium sulfate or oxide; salt (sodium chloride); potassium chloride or acetate; ascorbic acid; ferric orthophosphate; niacinamide; zinc sulfate or oxide; calcium pantothenate; copper gluconate; riboflavin; beta-carotene; pyridoxine hydrochloride; thiamin mononitrate; folic acid; biotin; chromium chloride or picolonate; potassium iodide; sodium selenate; sodium molybdate; phylloquinone; vitamin D3; cyanocobalamin; sodium selenite; copper sulfate; vitamin A; vitamin C; inositol; potassium iodide. Suitable dosages for vitamins and minerals may be obtained, for example, by consulting the U.S. RDA guidelines.

In other embodiments, the present invention provides nutritional supplements (e.g., energy bars or meal replacement bars or beverages) comprising the composition according to the invention. The nutritional supplement may serve as meal or snack replacement and generally provide nutrient calories. Preferably, the nutritional supplements provide carbohydrates, proteins, and fats in balanced amounts. The nutritional supplement can further comprise carbohydrate, simple, medium chain length, or polysaccharides, or a combination thereof. A simple sugar can be chosen for desirable organoleptic properties. Uncooked cornstarch is one example of a complex carbohydrate. If it is desired that it should maintain its high molecular weight structure, it should be included only in food formulations or portions thereof which are not cooked or heat processed since the heat will break down the complex carbohydrate into simple carbohydrates, wherein simple carbohydrates are mono- or disaccharides. The nutritional supplement contains, in one embodiment, combinations of sources of carbohydrate of three levels of chain length (simple, medium and complex; e.g., sucrose, maltodextrins, and uncooked cornstarch).

Sources of protein to be incorporated into the nutritional supplement of the invention can be any suitable protein utilized in nutritional formulations and can include whey protein, whey protein concentrate, whey powder, egg, soy flour, soy milk soy protein, soy protein isolate, caseinate (e.g., sodium caseinate, sodium calcium caseinate, calcium caseinate, potassium caseinate), animal and vegetable protein and hydrolysates or mixtures thereof. When choosing a protein source, the biological value of the protein should be considered first, with the highest biological values being found in caseinate, whey, lactalbumin, egg albumin and whole egg proteins. In a preferred embodiment, the protein is a combination of whey protein concentrate and calcium caseinate. These proteins have high biological value; that is, they have a high proportion of the essential amino acids. See Modern Nutrition in Health and Disease, 8th ed., Lea & Febiger, 1986, especially Volume 1, pages 30-32. The nutritional supplement can also contain other ingredients, such as one or a combination of other vitamins, minerals, antioxidants, fiber and other dietary supplements (e.g., protein, amino acids, choline, lecithin). Selection of one or several of these ingredients is a matter of formulation, design, consumer preferences and end-user. The amounts of these ingredients added to the dietary supplements of this invention are readily known to the skilled artisan. Guidance to such amounts can be provided by the U.S. RDA doses for children and adults. Further vitamins and minerals that can be added include, but are not limited to, calcium phosphate or acetate, tribasic; potassium phosphate, dibasic; magnesium sulfate or oxide; salt (sodium chloride); potassium chloride or acetate; ascorbic acid; ferric orthophosphate; niacinamide; zinc sulfate or oxide; calcium pantothenate; copper gluconate; riboflavin; beta-carotene; pyridoxine hydrochloride; thiamin mononitrate; folic acid; biotin; chromium chloride or picolonate; potassium iodide; sodium selenate; sodium molybdate; phylloquinone; vitamin D3; cyanocobalamin; sodium selenite; copper sulfate; vitamin A; vitamin C; inositol; potassium iodide.

The nutritional supplement can be provided in a variety of forms, and by a variety of production methods. In a preferred embodiment, to manufacture a food bar, the liquid ingredients are cooked; the dry ingredients are added with the liquid ingredients in a mixer and mixed until the dough phase is reached; the dough is put into an extruder, and extruded; the extruded dough is cut into appropriate lengths; and the product is cooled. The bars may contain other nutrients and fillers to enhance taste, in addition to the ingredients specifically listed herein.

It is understood by those of skill in the art that other ingredients can be added to those described herein, for example, fillers, emulsifiers, preservatives, etc. for the processing or manufacture of a nutritional supplement.

Additionally, flavors, coloring agents, spices, nuts and the like may be incorporated into the nutraceutical composition. Flavorings can be in the form of flavored extracts, volatile oils, chocolate flavorings, peanut butter flavoring, cookie crumbs, crisp rice, vanilla or any commercially available flavoring. Examples of useful flavoring include, but are not limited to, pure anise extract, imitation banana extract, imitation cherry extract, chocolate extract, pure lemon extract, pure orange extract, pure peppermint extract, imitation pineapple extract, imitation rum extract, imitation strawberry extract, or pure vanilla extract; or volatile oils, such as balm oil, bay oil, bergamot oil, cedarwood oil, walnut oil, cherry oil, cinnamon oil, clove oil, or peppermint oil; peanut butter, chocolate flavoring, vanilla cookie crumb, butterscotch or toffee. In one embodiment, the dietary supplement contains cocoa or chocolate.

Emulsifiers may be added for stability of the nutraceutical compositions. Examples of suitable emulsifiers include, but are not limited to, lecithin (e.g., from egg or soy), and/or mono- and di-glycerides. Other emulsifiers are readily apparent to the skilled artisan and selection of suitable emulsifier(s) will depend, in part, upon the formulation and final product. Preservatives may also be added to the nutritional supplement to extend product shelf life. Preferably, preservatives such as potassium sorbate, sodium sorbate, potassium benzoate, sodium benzoate or calcium disodium EDTA are used.

In addition to the carbohydrates described above, the nutraceutical composition can contain natural or artificial (preferably low calorie) sweeteners, e.g., saccharides, cyclamates, aspartamine, aspartame, acesulfame K, and/or sorbitol. Such artificial sweeteners can be desirable if the nutritional supplement is intended to be consumed by an overweight or obese individual, or an individual with type II diabetes who is prone to hyperglycemia.

Moreover, a multi-vitamin and mineral supplement may be added to the nutraceutical compositions of the present invention to obtain an adequate amount of an essential nutrient, which is missing in some diets. The multi-vitamin and mineral supplement may also be useful for disease prevention and protection against nutritional losses and deficiencies due to lifestyle patterns.

The dosage and ratios of catechin and/or epicatechin and additional components administered via a nutraceutical will vary depending upon known factors, such as the physiological characteristics of the particular composition and its mode and route of administration; the age, health and weight of the recipient; the nature and extent of the symptoms; the kind of concurrent treatment; the frequency of treatment; and the effect desired which can determined by the expert in the field with normal trials, or with the usual considerations regarding the formulation of a nutraceutical composition.

Compounds may be administered orally or via injection at a dose of from 0.1 to 500 mg/kg per day. The dose range for adult humans is generally from 5 mg to 2 g/day. Tablets or other forms of presentation provided in discrete units may conveniently contain an amount of one or more compounds which is effective at such dosage or as a multiple of the same, for instance, units containing 5 mg to 500 mg, usually around 10 mg to 200 mg.

In certain embodiments, the compounds disclosed herein are administered so as to acheive a plasma or cellular concentration of at least 0.1 µM, at least 0.25 µM, at least 0.5 µM, and at least 1 µM.

In various embodiments, desired concentration is maintained for at least 30 minutes, 1 hour, 3 hours, 6 hours, 12 hours, 24 hours, 48 hours, 72 hours, or more. In various other embodiments, the desired concentration is achieved at least once during each 12 hour period over at least 24 hours, 48 hours, 72 hours, 1 week, one month, or more; or at least once during each 24 hour period over at least 48 hours, 72 hours, 1 week, one month, or more. In order to maintain a desired concentration for a desired time, multiple doses of one or more compounds may be employed. The dosing interval may be determined based on the half-life for the clearances of each compound of interest from the body.

The amount of active ingredient that may be combined with the carrier materials to produce a single dosage form will vary depending upon the host treated and the particular mode of administration.

The compounds can be administered in various modes, e.g. orally, topically, or by injection. The precise amount of compound administered to a patient will be the responsibility of the attendant physician. The specific dose level for any particular patient will depend upon a variety of factors including the activity of the specific compound employed, the age, body weight, general health, sex, diets, time of administration, route of administration, rate of excretion, drug combination, the precise disorder being treated, and the severity of the indication or condition being treated. Also, the route of administration may vary depending on the condition and its severity.

In certain instances, it may be appropriate to administer at least one of the compounds described herein (or a pharmaceutically acceptable salt, ester, or prodrug thereof) in combination with another therapeutic agent. By way of example only, if one of the side effects experienced by a patient upon receiving one of the compounds herein is hypertension, then it may be appropriate to administer an anti-hypertensive agent in combination with the initial therapeutic agent. Or, by way of example only, the therapeutic effectiveness of one of the compounds described herein may be enhanced by administration of an adjuvant (i.e., by itself the adjuvant may only have minimal therapeutic benefit, but in combination with another therapeutic agent, the overall therapeutic benefit to the patient is enhanced). Or, by way of example only, the benefit of experienced by a patient may be increased by administering one of the compounds described herein with another therapeutic agent (which also includes a therapeutic regimen) that also has therapeutic benefit. By way of example only, in a treatment for diabetes involving administration of one of the compounds described herein, increased therapeutic benefit may result by also providing the patient with another therapeutic agent for diabetes. In any case, regardless of the disease, disorder or condition being treated, the overall benefit experienced by the patient may simply be additive of the two therapeutic agents or the patient may experience a synergistic benefit.

Specific, non-limiting examples of possible combination therapies include use of certain compounds of the invention with: nicroandil, a nicorandil derivative, tetracycline antibiotics, glycoprotein IIb/IIIa inhibitors, ADP receptor/P2Y12 inhibitors, prostaglandin analogues, COX inhibitors, antiplatelet drugs, anticoagulants, heparins, direct factor Xa inhibitors, direct thrombin (II) inhibitors, vasodilators, eptifibatide, tirofiban, abciximab, clopidogrel, ticlopidine, prasgurel, betaprost, iloprost, treprostinil, asprin, aloxiprin, ditazole, cloricromen, dipyridamole, indobufen, picotamide, triflusal, coumarins, a 1,3-indandione anticoagulant, heparin, bivalirudin, nicorandil, fendoldopam, hydralazine, nesiritide, nicardipine, nitroglycerine, and nitroprusside, nitrate donor vasodilators, ACE inhibitors, and anigotensin receptor blockers, an antipsychotic, olanzepine, clozapine, risperidone, quetiapnie, a nucleoside reverse transcriptase inhibitor, zidovudine, bupivacaine, lidocaine, thiazolidinediones, doxorubicin, sorafenib, daunorubicin, epirubicin, idarubicin, celecoxib, diclofenac, ibuprofen, indomethacin, mefenamic acid, meloxicam, naproxen, piroxicam, sulindac, atenolol, pioglitazone, rosiglitazone, isoniazid, valproic acid, tamoxifen, flutamide, lamivudine, zalcitabine, phenoformin, metformin, nefazodone, abacavir, didanosine, nevirapine, tenofovir, stavudine, ketoconazole, divalproex sodium, cysplatin, gentamicin, a cyclosporin, ifosfamide, a statin, tenofovir, metformin, a corticosteroid, cortisol, prednisone, dexamethasone, triamcinalone, prednisolone, an inotrope, epinephrine, isoproterenol, a fibrate, clofibrate, gemfibrizole, cyprofibrate, and bezafibrate.

In further embodiments, a compound of the invention is administered together with one or more tetracycline antibiotics such as doxycycline. In further embodiments, such administration is intravenous. In further embodiments, such combination is administered in a single pharmaceutical composition.

The epicatechin derivatives of the present invention can be formulated as disclosed herein or its presence otherwise can be created or increased, in combination with other agents commonly used in cardiac patients including, but not limited to, ACE inhibitors, beta blockers, diuretics, thrombolytic agents, NMDA receptor antagonists, spin-trap agents and aspirin. In addition, the epicatechin derivatives of the present invention can be formulated with other naturally occurring agents including, but not limited to, resveratrol and vitamin E. The epicatechin derivatives of the present invention can also be formulated with other agents administered to healthy individuals including, but not limited to, protein, vitamins, minerals, antioxidants, and the like.

In any case, the multiple therapeutic agents (at least one of which is a compound disclosed herein) may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may be any duration of time ranging from a few minutes to four weeks.

Thus, in another aspect, certain embodiments provide methods for treating mitochondrial-mediated disorders in a human or animal subject in need of such treatment comprising administering to said subject an amount of a compound disclosed herein effective to reduce or prevent said disorder in the subject, in combination with at least one additional agent for the treatment of said disorder that is known in the art. In a related aspect, certain embodiments provide therapeutic compositions comprising at least one compound disclosed herein in combination with one or more additional agents for the treatment of mitochondrial-mediated disorders.

Specific diseases to be treated by the compounds, compositions, and methods disclosed herein include diseases and conditions related to apoptosis and cellular necrosis caused by ischemia; acute coronary syndromes, including but not limited to myocardial infarction and angina; acute ischemic events in other organs and tissues, including but not limited to renal injury, renal ischemia and diseases of the aorta and its branches; injuries arising from medical interventions, including but not limited to coronary artery bypass grafting (CABG) procedures and aneurysm repair; and metabolic diseases, including but not limited to diabetes mellitus.

Further diseases to be treated by the compounds, compositions, and methods disclosed herein include conditions involving decreased mitochondrial function. Such conditions can include inborn errors of mitochondrial metabolism, aging of the skin (e.g., due to light exposure), a nutritional or vitamin deficiency, mitochondrial myopathy, diabetes mellitus, insulin resistance, metabolic syndrome, Friedreich's ataxia, pulmonary hypertension, chronic kidney disease (particularly that associated with glomerular epithelial injury or tubulointerstitial fibrosis, including diabetic nephropathy, focal segmental glomerulosclerosis, and chronic renal insufficiency), acute kidney injury (whether due to vascular insufficiency, drug effects, toxins, medical or surgical procedures, or otherwise), hypertension, multiple sclerosis, subacute sclerosing encephalopathy, dementia or other conditions of impaired cognition related to aging, vascular disease, metabolic impairment or neurodegeneration (e.g., Alzheimer's disease or other dementia), myoneurogenic gastrointestinal encephalopathy, Parkinson's disease, Huntington disease, Amyotrophic Lateral Sclerosis (ALS), mental retardation, deafness and blindness, obesity, hyperlipidemia, heart failure, stroke, lupus, and rheumatoid arthritis.

Further diseases to be treated by the compounds, compositions, and methods disclosed herein include conditions related to mitochondrial function. In certain embodiments, a compound or composition disclosed herein is administered in an amount effective to stimulate mitochondrial function in cells. Stimulation of mitochondrial function in cells may comprise stimulation of one or more of mitochondrial respiration and mitochondrial biogenesis. The compounds, compositions, and methods disclosed herein can assist in the prevention of impaired mitochondria biogenesis and thus prevention of the consequences of impaired mitochondrial biogenesis in various diseases and conditions, as well as provide for the active therapy of mitochondrial depletion that may have already occurred.

Further diseases to be treated by the compounds, compositions, and methods disclosed herein include conditions related to mitochondrial toxicity. In certain embodiments, a compound or composition disclosed herein is administered in an amount effective to stimulate mitochondrial function in cells. Stimulation of mitochondrial function in cells may comprise stimulation of one or more of mitochondrial respiration and mitochondrial biogenesis. The methods and compositions described herein can assist in prevention of impaired mitochondria function and biogenesis and thus prevention of the consequences of impaired mitochondrial biogenesis resulting from administration of chemical compositions that exhibit mitochondrial toxicity.

The present disclosure also provides a method for prophylaxis and/or treatment of, and/or ameliorating the symptoms of, a condition related to mitochondrial function in a mammalian subject, comprising administering to the subject an effective amount one or more epicatechin derivatives of the present invention.

Individuals at risk for a condition related to mitochondrial function can decrease the risk of necrosis in future events by taking epicatechin, catechin, nicorandil, or pharmaceutically acceptable salts, or derivatives thereof prophylactically up to an indefinite period of time. In the event that there is a present condition related to mitochondrial function, it is contemplated that the prophylactic administration of the compositions of the present invention will reduce symptoms from such condition.

Ischemia and reperfusion are physiologically different events and do not necessarily occur at the same time. As ischemia refers to deficiency of blood to a part typically due to a thrombus or embolus and reperfusion injury results when the obstruction or constriction is removed, it is possible and desirable to reduce the potential infarct size and adverse remodeling during the ischemia/reperfusion event. The disclosure provides methods and compositions useful for inhibiting ischemic and/or reperfusion injury comprising, for example, administering the epicatechin derivatives of the present invention (or pharmaceutically acceptable salts and prodrugs thereof) during the ischemia or alternatively after the ischemia, but before reperfusion has occurred, or alternatively after the ischemia and at the time of reperfusion. Disclosed herein are methods wherein the epicatechin derivatives of the present invention (or pharmaceutically acceptable salts and prodrugs thereof) are administered during, prior to, or after an ischemia/reperfusion event.

Tissues deprived of blood and oxygen suffer ischemic necrosis or infarction, often resulting in permanent tissue damage. Cardiac ischemia is often termed "angina," "heart disease," or a "heart attack," and cerebral ischemia is often termed a "stroke". Both cardiac and cerebral ischemia result from decreased blood and oxygen flow which is often followed by some degree of brain damage, damage to heart tissue, or both. The decrease in blood flow and oxygenation may be the result of occlusion of arteries, rupture of vessels, developmental malformation, altered viscosity or other quality of blood, or physical traumas. Diabetes is a risk factor for ischemia. Accordingly, methods and compositions of the disclosure can be used to prevent or inhibit the risk of ischemia or inhibit and reduce the damage caused by ischemic injury in diabetic patients. This can include ischemia resulting in vision loss and ulcerations in addition to cardiac and cerebral ischemic injury.

Loss of blood flow to a particular vascular region is known as focal ischemia; loss of blood flow to the entire brain, global ischemia. When deprived of blood, and thus, oxygen and glucose, brain tissue may undergo ischemic necrosis or infarction. The metabolic events thought to underlie such cell degeneration and death include: energy failure through ATP depletion; cellular acidosis; glutamate release; calcium ion influx; stimulation of membrane phospholipid degradation and subsequent free-fatty-acid accumulation; and free radical generation.

Spinal cord injury is the most serious complication of spinal column trauma and also of operations on the aorta for treatment of thoracic and thoracoabdominal aneurysms (Kouchoukos, J. Thorac. Cardiovasc. Surg. 99:659-664, (1990)). As described in U.S. Pat. No. 5,648,331, the spinal cord is the organ most sensitive to ischemia during cross-clamping of the aorta, where the resultant injury may produce paraparesis or paraplegia. Spinal cord ischemia and paraplegia develop in approximately eleven percent (11%) of patients undergoing elective descending thoracic and thoracoabdominal aneurysm repair and nearly forty percent (40%) undergoing emergent repairs (Crawford, J. Vas. Surg. 3:389-402, (1986)).

Myocardial ischemia occurs when the heart muscle does not receive an adequate blood supply and is thus deprived of necessary levels of oxygen and nutrients. A common cause of myocardial ischemia is atherosclerosis, which causes blockages in the blood vessels (coronary arteries) that provide blood flow to the heart muscle. Congestive heart failure (CHF) can also result in myocardial infarction.

Ischemic events affecting the intestines play a major role of the mortality and morbidity or numerous patients. As described in U.S. Pat. No. 6,191,109, ischemic injury to the small intestine leads to mucosal destruction, bacterial translocation and perforation.

Age-related macular degeneration (AMD) is the leading cause of visual impairment and blindness in the United States and elsewhere among people 65 years or older. Oxidative damage to the retina may be involved in the pathogenesis of AMD.

Reactive oxygen species (ROS), also designated free radicals, include among other compounds singlet oxygen, the superoxide anion ($O_2-$), nitric oxide (NO), and hydroxyl radicals. Mitochondria are particularly susceptible to damage included by ROS, as these are generated continuously by the mitochondrial respiratory chain. Production of ROS increases when cells experience a variety of stresses, including organ ischemia and reperfusion, ultraviolet light exposure and other forms of radiation. Reiter et al. (1998) Ann N.Y. Acad. Sci. 854:410-424; Saini et al. (1998) Res. Comm Mol. Pathol. Pharmacol. 101:259-268; Gebicki et al. (1999) Biochem. J. 338:629-636. ROS are also produced in response to cerebral ischemia, including that caused by stroke, traumatic head injury and spinal injury. In addition, when metabolism increases or a body is subjected to extreme exercise, the endogenous antioxidant systems are overwhelmed, and free radical damage can take place. Free radicals are reported to cause the tissue-damage associated with some toxins and unhealthful conditions, including toxin-induced liver injury. Obata (1997) J. Pharm. Pharmacol. 49:724-730; Brent et al. (1992) J. Toxicol. Clin. Toxicol. 31:173-196; Rizzo et al. (1994) Zentralbl. Veterinarmed. 41:81-90; Lecanu et al. (1998) Neuroreport 9:559-663.

The disclosure provides a method for treating and/or ameliorating the symptoms of an ischemic condition in a mammalian subject, and for treating and/or ameliorating the symptoms of an ischemic condition in a mammalian subject. In some embodiments, the ischemic condition is selected from the group consisting of cerebral ischemia; intestinal ischemia; spinal cord ischemia; cardiovascular ischemia; myocardial ischemia associated with myocardial infarction; myocardial ischemia associated with CHF, ischemia associated with age-related macular degeneration (AME); liver ischemia; kidney/renal ischemia; dermal ischemia; vasoconstriction-induced tissue ischemia; penile ischemia as a consequence of priapism and erectile dysfunction; ischemia associated with thromboembolytic disease; ischemia associated with microvascular disease; and ischemia associated with diabetic ulcers, gangrenous conditions, post-trauma syndrome, cardiac arrest resuscitation, hypothermia, peripheral nerve damage or neuropathies. In some embodiments, the tissue ischemic condition is cerebral ischemia.

In one aspect, methods of the disclosure relate to preventing neuronal damage in a mammalian subject at risk of developing injury due to a cerebral ischemic condition, e.g. for example, by an infarct in the brain. The methods of reducing neuronal damage relate to minimizing the extent and/or severity of injury in the brain associated with or due to a cerebral ischemic condition by ameliorating or reducing the injury that would otherwise occur. The disclosure provides prophylactic treatments for neuronal damage including cell death and/or presence of tissue edema and/or cognitive dysfunction and/or cerebral infarcts which may be due to ischemic, hypoxic/anoxic, or hemorrhagic events. The method is intended for a subject at risk of neuronal damage that is associated with, or results from, an acute or chronic medical condition. Such conditions might arise as a result of medical or surgical treatment planned for the subject (e.g., angioplasty) or as a result of an emergent medical condition such as a stroke or severe blood loss. Other conditions which place a subject at risk for neuronal damage associated with a cerebral ischemic condition include a genetic predisposition to stroke or a condition that is understood to increase the probability of incurring a cerebral infarct such as atherosclerosis, previous stroke or transient ischemic attacks, diabetes mellitus, hypertension, hypercholesterolemia, a history of smoking and may also include schizophrenia, epilepsy, neurodegenerative disorders, Alzheimer's disease and Huntington's disease. Diagnostic and/or pathological characterization of stroke victims has identified numerous additional medical conditions producing stroke that are widely known to practitioners of internal and neurological medicine.

In certain embodiments, the compounds and compositions disclosed herein are administered together with one or more compounds independently selected from the group consisting of tetracycline antibiotics, glycoprotein Hb/IIIa inhibitors, ADP receptor/P2Y12 inhibitors, prostaglandin analogues, COX inhibitors, antiplatelet drugs, anticoagulants, heparins, direct factor Xa inhibitors, direct thrombin (II) inhibitors, and vasodilators (e.g., nicroandil or a derivative thereof).

In certain embodiments, the compounds and compositions disclosed herein are administered together with one or more compounds which exhibit mitochondrial toxicity. Such compounds include, but are not limited to, those described above in regard to drug-induced mitochondrial dysfunction of the heart, liver and kidneys. A number of drug classes have recently been identified as inducing organ degeneration or other side effects which are mediated by their effects on mitochondrial bioenergetics. The most frequent targets in drug-induced mitochondrial dysfunction are the heart, liver and kidneys, although other organs can also be affected. A recent summary by Pereira et al. in Current Drug Safety, 4: 34-54, 2009 (hereby incorporated by reference in its entirety) includes the following non-limiting list of exemplary drugs and drug classes:

1. Cardiovascular Toxicity

Nucleoside reverse transcriptase inhibitors (NRTIs); Zidovudine (AZT); Bupivacaine; Lidocaine; Thiazolidinediones (TZD); Doxorubicin (DOX); Sorafenib; Daunorubicin; Epirubicin; Idarubicin; Celecoxib; Diclofenac; Ibuprofen; Indomethacin; Mefenamic acid; Meloxicam; Naproxen; Piroxicam; Sulindac; Atenolol; Pioglitazone; Rosiglitazone.

2. Hepatic Toxicity

Isoniazid; Valproic acid; Tamoxifen; Flutamide; Lamivudine; Zidovudine (AZT); Zalcitabine; Phenoformin; Metformin; Nefazodone; Abacavir; Didanosine; Nevirapine; Tenofovir; Stavudine; Ketoconazole; Divalproex Sodium.

3. Renal Toxicity

Doxorubicin (DOX); Cisplatin; Gentamicin; Cyclosporin A; Ifosfamide; Statins; Tenofovir.

In certain embodiments, the compounds and compositions disclosed herein result in an increased ability to exercise. This includes, for example, recovery from immobilization of a body part, sarcopenia, aging, administration of one or more drugs, infections, chronic illness, impaired nutrition, other causes, or simply improving general exercise capacity. A subject may be selected based on age, an activity state, or a nutritional state (e.g., subjects receiving total parenteral nutrition, infant formula, etc.) of said animal.

In certain embodiments, administration of the compounds and compositions disclosed herein provide a method for improving muscle structure or function; a method for improving mitochondrial effects associated with exercise; a method for enhancing the capacity for exercise in those limited by age, inactivity, diet, or any of the aforementioned diseases and conditions; a method for enhancing muscle health and function in response to exercise; a method for enhancing muscle health and function in the clinical setting of restricted capacity for exercise, whether due to injury, inactivity, obesity, hyperlipidemia, or any of the aforementioned diseases and conditions; and/or a method to enhance recovery of muscles from vigorous activity or from injury associated with vigorous or sustained activity.

In certain embodiments, administration of the compounds and compositions disclosed herein provide a method for treating a condition involving decreased mitochondrial function in an animal.

In certain embodiments, administration of the compounds and compositions disclosed herein provide a method for treatment of a condition related to mitochondrial function in a subject caused by one or more chemical compositions which cause mitochondrial toxicity. Mechanisms that perturb mitochondrial function or number can be broadly divided into three categories: (1) modulation of mitochondrial metabolism; (2) injury to the mitochondria such that structural damage or alteration inhibits the important functions of mitochondria such as oxidative phosphorylation or calcium sequestration; and (3) decreased number of mitochondria arising from persistent or extreme injury to the mitochondria and resulting in sustained impairment of mitochondrial function in the absence of biogenesis. Chronic mitochondrial depletion and the symptoms arising thereof can occur as a result of drug-associated toxicity or as a combination of drug associated toxicity occurring within a background of biological depletion of mitochondrial number, as occurs in diabetes, obesity, hyperlipidemia, and during the course of aging.

Examples of drugs whose adverse side effects are associated with perturbation of mitochondrial number, function or structure are nucleoside reverse transcriptase inhibitors, zidovudine, bupivacaine, lidocaine, thiazolidinediones, doxorubicin, sorafenib, daunorubicin, epirubicin, idarubicin, celecoxib, diclofenac, ibuprofen, indomethacin, mefenamic acid, meloxicam, naproxen, piroxicam, sulindac, atenolol, pioglitazone, rosiglitazone, isoniazid, valproic acid, tamoxifen, flutamide, lamivudine, zalcitabine, phenoformin, metformin, nefazodone, abacavir, didanosine, nevirapine, tenofovir, stavudine, ketoconazole, divalproex sodium, cysplatin, gentamicin, a cyclosporin, ifosfamide, a statin, and tenofovir, metformin, corticosteroids including cortisol and predisone and dexamethasone and triamcinalone and prednisolone, inotropes such as epinephrine, isoproterenol, and other compounds that augment myocardial contractility, fibrates as a class, including clofibrate, gemfibrizole, cyprofibrate, and bezafibrate. Perturbing effects on mitochondrial function or number are not part of the intended therapeutic mechanism of these drugs, but rather are an unintended side effect of such drugs, limiting their therapeutic usefulness because of the side effects adversely affecting mitochondria, the predominant energy source for effective cellular function. Individuals at risk for a condition related to mitochondrial toxicity can decrease the risk of such toxicity in future events prophylactically. In the event that there is a present condition related to mitochondrial toxicity, it is contemplated that the administration of the compounds or compositions disclosed herein will reduce symptoms from such condition.

In certain embodiments, administration of the compounds and compositions disclosed herein provide a method for treating ischemia. In further embodiments, said method provides a method for preventing myocardial damage in a subject at risk of developing injury due to a cardiovascular ischemic condition, e.g. for example, by a myocardial infarction or chronic heart failure. The methods of reducing myocardial damage relate to minimizing the extent and/or severity of injury in the heart associated with or due to a myocardial ischemic condition by ameliorating or reducing the injury that would otherwise occur. The disclosure provides prophylactic treatments for myocardial damage including cell death and/or presence of myocardial edema and/or myocardial infarcts which may be due to ischemic, hypoxic/anoxic, or hemorrhagic events. The method is intended for a subject at risk of myocardial damage that is associated with, or results from, an acute or chronic medical condition. Such conditions might arise as a result of medical or surgical treatment planned for the subject (e.g., angioplasty) or as a result of an emergent medical condition such as a myocardial infarction or severe blood loss. Other conditions which place a subject at risk for myocardial damage associated with a myocardial ischemic condition include a genetic predisposition to myocardial infarction or a condition that is understood to increase the probability of incurring a myocardial infarct such as atherosclerosis, chronic heart failure, previous myocardial infarction or transient ischemic attacks, diabetes mellitus, hypertension, hypercholesterolemia, and a history of smoking.

Besides being useful for human treatment, certain compounds and formulations disclosed herein may also be useful for veterinary treatment of companion animals, exotic animals and farm animals, including mammals, rodents, and the like. More preferred animals include horses, dogs, and cats.

The invention is further illustrated by the following examples.

EXAMPLES 1-2

2-(4-Allyloxy-3-hydroxy-phenyl)-chroman-3,5,7-triol (Example 1)

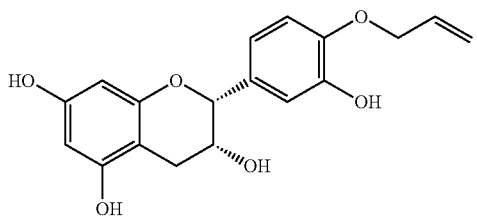 [SMILES: C=CCOc1ccc([C@H]2Oc3cc(O)cc(O)c3C[C@H]2O)cc1O]

and 2-(3-Allyloxy-4-hydroxy-phenyl)-chroman-3,5,7-triol (Example 2)

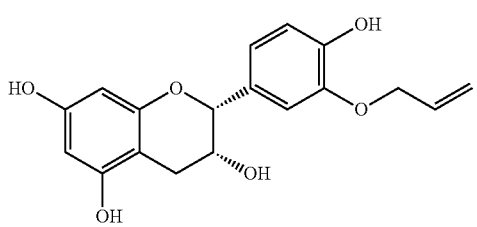 [SMILES: C=CCOc1cc([C@H]2Oc3cc(O)cc(O)c3C[C@H]2O)ccc1O]

To a mixture of (−)-epicatechin (1.16 g, 4 0 mmol) and potassium carbonate (1.10 g, 8.0 mmol) in dry acetone was added allyl bromide (0.41 mL, 4.8 mmol). The reaction was heated at reflux, under nitrogen, protected from light with vigorous stirring for 4 h. The reaction was filtered and concentrated onto silica gel. The crude product was purified on a Biotage 50 g silica gel column eluting with a gradient of 40-70% ethyl acetate/hexane and then 70% ethyl acetate/hexane. The major peak, corresponding to a mixture of monoallylated products, was isolated. This mixture was further purified by preparative reverse phase HPLC using a gradient of 1:9 to 8:2 acetonitrile/(0.2% formic acid/water) over 20 min. The appropriate fractions were frozen and lyophilized to give as white powders to provide 2-(4-Allyloxy-3-hydroxy-phenyl)-chroman-3,5,7-triol and 2-(3-Allyloxy-4-hydroxy-phenyl)-chroman-3,5,7-triol.

2-(4-Allyloxy-3-hydroxy-phenyl)-chroman-3,5,7-triol

1H NMR (300 MHz, acetone-$d_6$) δ (ppm): ~2.7-2.9 (m, 2H, $CH_2$, $H_2O$), 3.64 (d, 1H, J=5.7 Hz, OH), 4.21 (m, 1H, CH), 4.59 (d, 2H, J=5.7 Hz, allyl $CH_2$), 4.91 (s, 1H, CH), 5.22 (dd, 1H, J=10.5, 1.2 Hz, vinyl $CH_2$), 5.42 (dd, 1H, J=17.4, 1.5 Hz, vinyl $CH_2$), 5.91 (d, 1H, J=2.1, ArH), 6.02 (d, 1H, J=1.8 Hz, ArH) ~6.1 (m, 1H, vinyl CH), 6.80 (d, 1H, J=8.1 Hz, ArH), 6.96 (dd, 1H, J=7.8, 1.5 Hz, ArH), 7.18 (d, 1H, J=1.2, ArH), 7.4-8.4 (br, 3H, ArOH)

2-(3-Allyloxy-4-hydroxy-phenyl)-chroman-3,5,7-triol

1H NMR (300 MHz, acetone-$d_6$) δ (ppm): 2.74 (dd, 1H, J=16.5, 3.3, $CH_2$), ~2.80-2.94 (m, 1H, $CH_2$, $H_2O$), 3.61 (d, 1H, J=5.4, OH), 4.22 (m, 1H, CH), 4.60 (d, 2H, J=5.1 Hz, allyl $CH_2$), 4.91 (s, 1H, CH), 5.23 (dd, 1H, J=10.8, 1.5 Hz, vinyl $CH_2$), 5.42 (dd, 1H, J=17.4, 1.5 Hz, vinyl $CH_2$), 5.91 (d, 1H, J=2.1, ArH), 6.02 (d, 1H, J=1.8 Hz, ArH) ~6.1 (m, 1H, vinyl CH), 6.91 (m, 2H, ArH) 7.07 (s, 1H, ArH), 7.4-8.2 (br, 3H, ArOH).

EXAMPLE 3

2-(3-Hydroxy-4-propoxy-phenyl)-chroman-3,5,7-triol

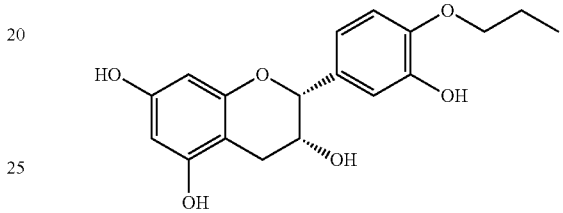

To a suspension of 10% palladium on carbon (5 mg, 10 mol %) in 5 mL ethanol which had been stirred vigorously under 1 atmosphere of hydrogen for 10 minutes then cooled with an ice/methanol bath was added a solution of 2-(4-Allyloxy-3-hydroxy-phenyl)-chroman-3,5,7-triol (50 mg) in 2 mL ethanol. The ice bath was removed and the reaction was stirred for 3 h under 1 atmosphere of hydrogen. The mixture was passed through a 0.22 micron nylon syringe filter and concentrated to a foam which was dissolved in acetonitrile/water, frozen, and lyophilized give 2-(3-Hydroxy-4-propoxy-phenyl)-chroman-3,5,7-triol as a white powder.

1H NMR (300 MHz, acetone-$d_6$) δ (ppm): 1.03 (t, 3H, J=7.8 Hz, $CH_3$), 1.80 (sept, 2H, J=6.6 Hz, $CH_2$), 2.68-2.94 (m, 2H, $CH_2$), 3.56 (d, 1H, J=5.4, OH), 4.00 (t, 2H, J=6.6 Hz, $CH_2$), 4.22 (m, 1H, CH), 4.91 (s, 1H, CH), 5.92 (d, 1H, J=2.4 Hz, ArH), 6.01 (d, 1H, J=2.1 Hz, ArH), 6.90 (m, 2H, ArH), 7.05 (s, 1H, ArH), 7.38 (s, 1H, ArOH), 7.91 (s, 1H, ArOH), 8.07 (s, 1H, ArOH).

EXAMPLE 4

2-(4-Hydroxy-3-propoxy-phenyl)-chroman-3,5,7-triol

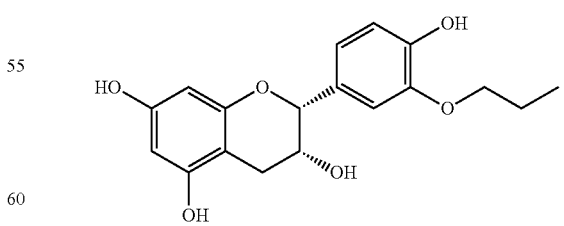

Following the procedures described in Example 3, but replacing 2-(4-Allyloxy-3-hydroxy-phenyl)-chroman-3,5,7-triol with other appropriate compounds, and utilizing modifications known to those skilled in the art, 2-(4-Hydroxy-3-propoxy-phenyl)-chroman-3,5,7-triol was prepared.

1H NMR (300 MHz, dmso-d$_6$) δ (ppm): 0.98 (t, 3H, J=7.2 Hz, CH$_3$), 1.73 (sept, 2H, J=6.9 Hz, CH$_2$), 2.65 (br d, 1H, J=3.9 Hz, CH$_2$), 2.71 (br d, 1H, J=4.5, CH$_2$), 3.87 (t, 2H, J=6.3 Hz, CH$_2$), 4.01 (s, 1H, OH), 4.69 (d, 1H, J=4.5, CH), 4.77 (s, 1H, CH), 5.71 (s, 1H, ArH), 5.88 (s, 1H, ArH), 6.71 (d, 1H, J=8.1 Hz, ArH), 6.79 (d, 1H, J=8.4 Hz, ArH), 6.99 (s, 1H, ArH), 8.75 (s, 1H, ArOH), 8.90 (s, 1H, ArOH), 9.07 (s, 1H, ArOH).

EXAMPLE 5

2-(3,4-Dihydroxy-phenyl)-3-propoxy-chroman-5,7-diol

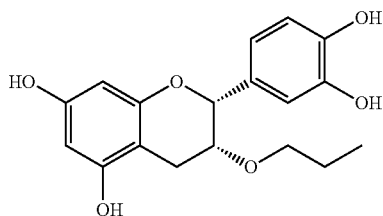 [SMILES: CCCO[C@@H]1Cc2c(O)cc(O)cc2O[C@@H]1c1ccc(O)c(O)c1]

To a suspension of 20% palladium on carbon (80 mg) in 1:1 ethyl acetate/ethanol (15 mL) which had been stirred vigorously under 1 atmosphere of hydrogen for 10 minutes then cooled with an ice/methanol bath was added 3-Allyloxy-5,7-bis-benzyloxy-2-(3,4-bis-benzyloxy-phenyl)-chroman (200 mg). The ice bath was removed and the reaction was stirred for 2 h under 1 atmosphere of hydrogen. The mixture was filtered and concentrated, and purified by preparative reverse phase HPLC using a gradient of 5% to 100% acetonitrile/water over 10 min The appropriate fractions were frozen and lyophilized to yield 2-(3,4-Dihydroxy-phenyl)-3-propoxy-chroman-5,7-diol as a white powder.

1H NMR (300 MHz, acetone-d$_6$) δ (ppm): 0.76 (t, 3H, J=7.2 Hz, CH$_3$), 1.40 (sext, 2H, J=6.9 Hz, CH$_2$), 2.68-2.98 (m, 2H, CH$_2$), 3.19 (m, 2H, CH$_2$), 5.90 (d, 1H, J=2.4 Hz, ArH), 6.00 (d, 1H, J=2.1, ArH), 6.76 (d, 1H, J=8.1, ArH), 6.81 (dd, 1H, J=8.4, 1.8 Hz), 7.03 (s, 1H, ArH), 7.6-8.2 (m, 3H, ArOH).

EXAMPLE 6

4-((2R,3R)-3-hydroxy-5,7-dimethoxychroman-2-yl)-2-methoxyphenyl trifluoromethanesulfonate

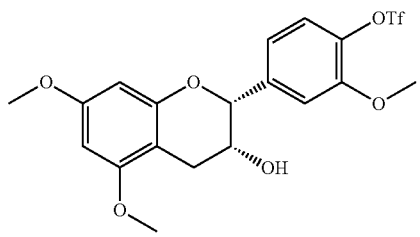

To a suspension of (2R,3R)-2-(4-hydroxy-3-methoxyphenyl)-5,7-dimethoxychroman-3-ol (400 mg, 1.1 mmol) and potassium carbonate (607 mg, 4.4 mmol) in acetone (20 mL) was added dimethyl sulfate (420 mL, 4.4 mmol). The reaction was heated at reflux for 5 hours, cooled to RT, treated with 7 N NH$_3$/MeOH (0.5 mL), stirred for 0.5 hours filtered and concentrated to give 381 mg crude solid. To a solution of this solid in 20:1:1 THF/MeOH/water (20 mL) was added 20% Pd(OH)2 (130 mg). The reaction mixture was stirred under 1 atm hydrogen for 2 hours, filtered through celite, and concentrated to 274 mg crude white solid. To a solution of this solid (0.8 mmol) in DCM (5 mL) at −10° C. was added N-phenyl-bis(trifluoromethanesulfonimide) (320 mg, 0.88 mmol) followed by triethylamine (270 mL, 1.9 mL). The reaction was allowed to warm to RT and stirred ON. The reaction mixture was diluted with ethyl acetate, washed with brine, 1 N NaOH, brine, dried over sodium sulfate and concentrated to give 319 mg white foam.

1H NMR (300 MHz, DMSO-d$_6$) δ (ppm): 2.63 (m, 1H, CH$_2$), 2.79 (m, 1H, CH$_2$), 3.71 (s, 3H, OCH$_3$), 3.75 (s, 3H, OCH$_3$), 3.90 (s, 3H, OCH$_3$), 4.18 (m, 1H, OH), 4.80 (d, 1H, J=4.8 Hz, CH), 5.03 (s, 1H, CH), 6.11 (s, 1H, ArH), 6.14 (s, 1H, ArH), 7.15 (d, 1H, J=8.4 Hz, ArH), 7.35-7.46 (m, 2H, ArH).

EXAMPLE 7

Methyl 4-((2R,3R)-3-hydroxy-5,7-dimethoxychroman-2-yl)-2-methoxybenzoate

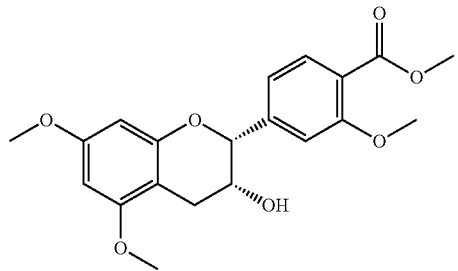

A solution of 4-((2R,3R)-3-hydroxy-5,7-dimethoxychroman-2-yl)-2-methoxyphenyl trifluoromethanesulfonate (200 mg, 0.4 mmol) and triethylamine (123 μL, 0.88 mmol) in MeOH (3 mL)/DMSO (4 mL) was sparged with CO for 5 min. To the mixture was added Pd(OAc)$_2$ (9 mg, 0.04 mmol) and dppf (44 mg, 0.08 mmol). The reaction was heated to 70° C. while sparging with CO or 10 min and stirred at 70° C. under 1 atm. of CO for 4 hr. The mixture was diluted with ethyl acetate, washed with 10% citric acid, brine, dried over magnesium sulfate, and concentrated. The residue was purified by a Biotage silica gel column eluting with 20% to 50% ethyl acetate/hexane to yield 130 mg methyl 4-((2R,3R)-3-hydroxy-5,7-dimethoxychroman-2-yl)-2-methoxybenzoate as a white foam.

1H NMR (300 MHz, DMSO-d$_6$) δ (ppm): 2.61 (dd, 1H, J=17.1, 2.1 Hz, CH$_2$), 2.80 (dd, 1H, J=16.5, 3.9 Hz, CH$_2$), 3.71 (s, 3H, OCH$_3$), 3.74 (s, 3H, OCH$_3$), 3.78 (s, 3H, OCH$_3$), 3.82 (s, 3H, OCH$_3$), 4.19 (m, 1H, OH), 4.84 (d, 1H, J=4.8 HZ, CH), 5.03 (s, 1H, CH), 6.13 (m, 2H, ArH), 7.10 (d, 1H, J=7.8 Hz, ArH), 7.22 (s, 1H, ArH), 7.64 (d, 1H, J=7.8 Hz, ArH).

EXAMPLE 8

4-((2R,3R)-3-hydroxy-5,7-dimethoxychroman-2-yl)-2-methoxybenzoic acid

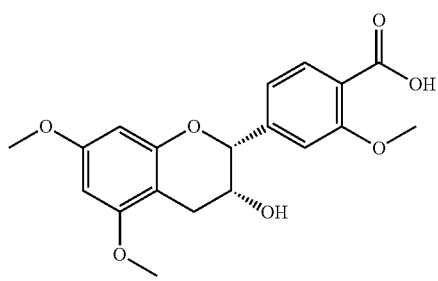

A solution of 4-((2R,3R)-3-hydroxy-5,7-dimethoxychroman-2-yl)-2-methoxyphenyl trifluoromethanesulfonate (200 mg, 0.4 mmol) and triethylamine (123 mL, 0.88 mmol) in MeOH (3 mL)/DMSO (4 mL) was sparged with CO for 5 min. To the mixture was added Pd(OAc)$_2$ (9 mg, 0.04 mmol) and dppf (44 mg, 0.08 mmol). The reaction was heated to 70° C. while sparging with CO or 10 min and stirred at 70° C. under 1 atm. of CO for 4 hr. The mixture was diluted with ethyl acetate, washed with 10% citric acid, brine, dried over magnesium sulfate, and concentrated. The residue was purified by a Biotage silica gel column eluting with 20% to 50% ethyl acetate/hexane to yield 130 mg 4-((2R,3R)-3-hydroxy-5,7-dimethoxychroman-2-yl)-2-methoxybenzoic acid as a white foam.

1H NMR (300 MHz, DMSO-d$_6$) δ (ppm): 2.60 (d, 1H, J=15.3 Hz, CH$_2$), 2.80 (dd, 1H, J=16.5, 3.9 Hz, CH$_2$), 3.71 (s, 3H, OCH$_3$), 3.74 (s, 3H, OCH$_3$), 3.81 (s, 3H, OCH$_3$), 4.18 (m, 1H, OH), 4.84 (d, 1H, J=4.2 HZ, CH), 5.02 (s, 1H, CH), 6.12 (2, 1H, ArH), 6.13 (2, 1H, ArH), 7.08 (d, 1H, J=7.8 Hz, ArH), 7.20 (s, 1H, ArH), 7.62 (d, 1H, J=7.8 Hz, ArH).

EXAMPLE 9

(4-((2R,3R)-3-hydroxy-5,7-dimethoxychroman-2-yl)-2-methoxyphenyl)(4-methylpiperazin-1-yl)methanone

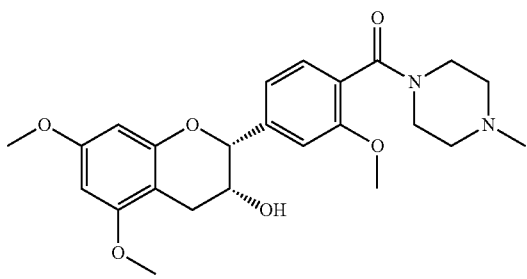

To a solution of 4-((2R,3R)-3-hydroxy-5,7-dimethoxychroman-2-yl)-2-methoxybenzoic acid (20 mg, 0.08 mmol) and triethylamine (22 μL, 0.16 mmol) in DMF (1 mL) was added HATU (38 mg, 0.1 mmol). The mixture was stirred for 0.5 hr and N-methylpiperazine (20 μL, 0.16 mmol) was added and the reaction was stirred for 12 hr. The mixture was diluted with ethyl acetate, washed with sat. sodium carbonate and brine, dried over sodium sulfate, and concentrated. The crude product was purified by preparative reverse phase HPLC using a gradient of 5% to 30% acetonitrile/(0.2% formic acid/water) over 10 min, analyzing at 280 nm. The appropriate fractions were frozen and lyophilized to give (4-((2R,3R)-3-hydroxy-5,7-dimethoxychroman-2-yl)-2 methoxyphenyl)(4-methylpiperazin-1-yl)methanone.

m/z 443 [M+H]+

EXAMPLES 10-11

Ethyl 2-(2-hydroxy-4-((2R,3R)-3,5,7-trihydroxychroman-2-yl)phenoxy)acetate (Example 10)

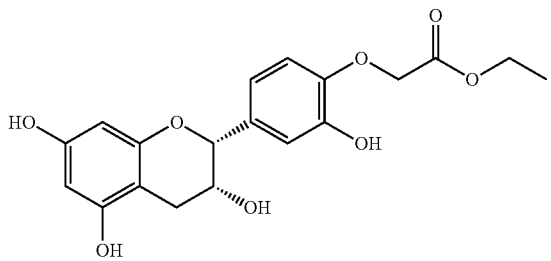 [SMILES: CCOC(=O)COc1ccc([C@H]2Oc3cc(O)cc(O)c3C[C@H]2O)cc1O]

and

Ethyl 2-(2-hydroxy-5-((2R,3R)-3,5,7-trihydroxychroman-2-yl)phenoxy)acetate (Example 11)

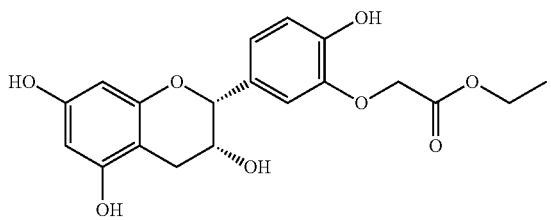 [SMILES: CCOC(=O)COc1cc([C@H]2Oc3cc(O)cc(O)c3C[C@H]2O)ccc1O]

To a solution of (−)-epicatechin (1.16 g, 4 mmol) and potassium carbonate (1.1 g, 8 mmol) in DMF (10 mL) at −20° C. was added ethyl bromoacetate (490 mL, 4.4 mmol). The reaction was stirred at the same temperature for 2 hr, allowed to warm to RT, and stirred for 2 hr. The reaction was diluted with ethyl acetate, washed with citric acid then brine, dried over sodium sulfate, and concentrated. The residue was purified by preparative reverse phase HPLC using a gradient of 10% to 80% acetonitrile/(0.2% formic acid/water) over 20 min, analyzing at 280 nm. The appropriate fractions were frozen and lyophilized to give as white powders:

Ethyl 2-(2-hydroxy-4-((2R,3R)-3,5,7-trihydroxychroman-2-yl)phenoxy)acetate

1H NMR (300 MHz, DMSO-d$_6$) δ (ppm): 1.22 (t, 3H, J=7.2, CH$_3$), 2.45 (m, 1H, CH$_2$), 2.69 (dd, 1H, J=16.2, 4.2 Hz, CH$_2$), 4.01 (m, 1H, OH), 4.16 (q, 2H, J=7.2, CH$_2$), 4.70 (m, 1H, CH), 4.77 (s, 1H, CH), 5.71 (s, 1H, ArH), 5.88 (s, 1H, ArH), 6.75 (m, 2H, ArH), 6.95 (s, 1H, ArH), 8.8-9.2 (m, 3H, ArOH).

Ethyl 2-(2-hydroxy-5-((2R,3R)-3,5,7-trihydroxy-chroman-2-yl)phenoxy)acetate

1H NMR (300 MHz, DMSO-d6) δ (ppm): 1.22 (t, 3H, J=7.2, CH3), 2.45 (m, 1H, CH2), 2.69 (dd, 1H, J=16.2, 4.2 Hz, CH2), 4.03 (m, 1H, OH), 4.16 (q, 2H, J=7.2, CH2), 4.67-4.85 (m, 4H, CH, CH, CH2), 5.71 (s, 1H, ArH), 5.89 (s, 1H, ArH), 6.88 (d, 1H, J=8.7, ArH), 6.96 (m, 1H, ArH), 7.02 (s, 1H, ArH), 8.91 (s, 1H, ArOH), 9.13 (s, 1H, ArOH).

EXAMPLE 12

Ethyl 2-(4-((2R,3R)-3-hydroxy-5,7-dimethoxychroman-2-yl)-2-methoxyphenoxy)acetate

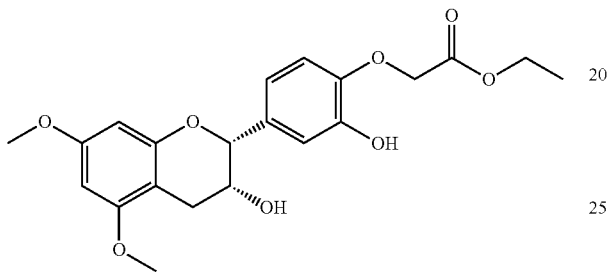

To a suspension of ethyl 2-(2-hydroxy-4-((2R,3R)-3,5,7-trihydroxychroman-2-yl)phenoxy)acetate (250 mg, 0 7 mmol) and potassium carbonate (386 mg, 2 8 mmol) in DMA (5 mL) was added iodomethane (180 mL, 2.8 mmol). The reaction was stirred at RT for 72 hr then diluted with ethyl acetate, washed with sat. sodium carbonate and brine, dried over magnesium sulfate and concentrated. The residue was purified by preparative reverse phase HPLC using a gradient of 10% to 80% acetonitrile/(0.2% formic acid/water) over 20 min, analyzing at 280 nm. The appropriate fractions were frozen and lyophilized to give (12) as a white solid.

1H NMR (300 MHz, DMSO-d6) δ (ppm): 1.22 (t, 3H, J=15.3, CH3), 2.58 (m, 1H, CH2), 2.76 (m, 1H, CH2), 3.70 (s, 3H, OCH3), 3.74 (s, 3H, OCH3), 3.77 (s, 3H, OCH3), 4.1 (m, 1H, OH), 4.73 (s, 2H, CH2), 4.81 (d, 1H, J=15.5, CH), 4.89 (s, 1H, CH), 6.06 (s, 1H, ArH), 6.11 (s, 1H, ArH), 6.83 (d, 1H, J=8.4, ArH), 6.93 (d, 1H, J=8.1, ArH), 7.11 (s, 1H, ArH).

EXAMPLE 13

2-(4-((2R,3R)-3-hydroxy-5,7-dimethoxychroman-2-yl)-2-methoxyphenoxy)acetic acid

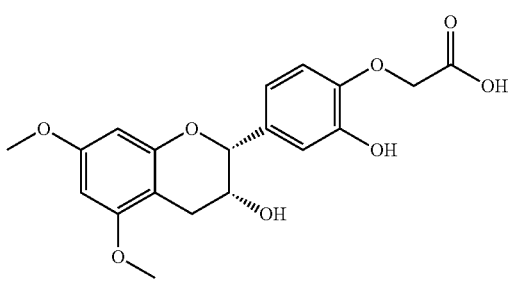 [SMILES: COc1cc(OC)c2c(c1)O[C@H](c1ccc(OCC(=O)O)c(O)c1)[C@H](O)C2]

To a solution of ethyl 2-(4-((2R,3R)-3-hydroxy-5,7-dimethoxychroman-2-yl)-2-methoxyphenoxy)acetate (80 mg, 0.2 mmol) in MeOH (5 mL) was added 1N LiOH (250 μL). The reaction was stirred at RT for 2 hrs, diluted with ethyl acetate, washed with 10% citric acid and brine, dried over magnesium sulfate, and concentrated. The residue was purified by preparative reverse phase HPLC using a gradient of 5% to 100% acetonitrile/(0.2% formic acid/water) over 10 min, analyzing at 280 nm. The appropriate fractions were frozen and lyophilized to give (13) as a white solid.

1H NMR (300 MHz, DMSO-d6) δ (ppm): 2.58 (d, 1H, J=16.5 Hz, CH2), 2.76 (m, 1H, CH2), 3.70 (s, 3H, OCH3), 3.74 (s, 3H, OCH3), 3.76 (s, 3H, OCH3), 4.1 (m, 1H, OH), 4.62 (s, 2H, CH2), 4.81 (br, 1H, CH), 4.89 (s, 1H, CH), 6.06 (d, 1H, J=2.4, ArH), 6.11 (d, 1H, J=2.1, ArH), 6.81 (d, 1H, J=8.4, ArH), 6.93 (d, 1H, J=8.1, ArH), 7.10 (s, 1H, ArH).

EXAMPLE 14

(2R,3R)-2-(3,4-dihydroxyphenyl)-3-methoxychroman-5,7-diol

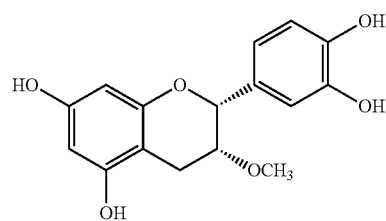 [SMILES: CO[C@@H]1Cc2c(O)cc(O)cc2O[C@@H]1c1ccc(O)c(O)c1]

Step 1

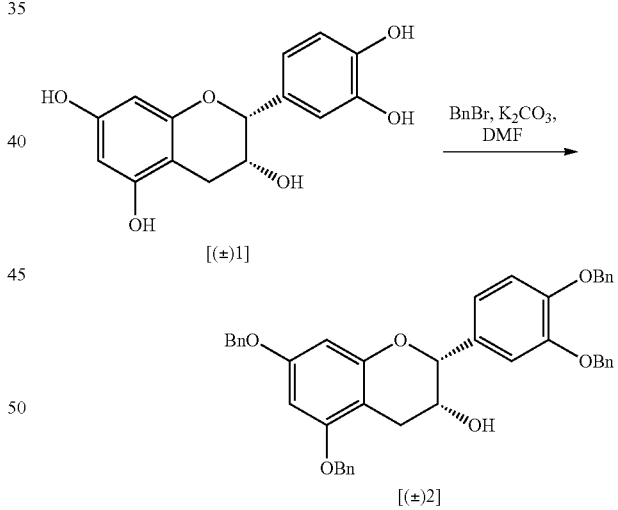

To a stirred solution of 1 (1.0 gm, 3 4 mmol) in DMF, anhydrous K2CO3 (2.3 gm, 17.0 mmol) was added at 0° C. under nitrogen atmosphere. After 15 minutes of stirring at same temperature, benzyl bromide (2.0 ml, 17 0 mmol) was added drop-wise. The reaction temperature was allowed to increase upto 25° C. and stirring was continued for overnight. Consumption of 1 was monitored by TLC. After complete consumption of 1, water (50 ml) was added and organic layer was extracted with ethyl acetate (2×100 ml). The combined organic layers were washed with water, brine and dried over sodium sulphate. The organic layer was concentrated to afford light brown sticky material which was further purified using silica gel column chromatography and 8% ethyl acetate in hexane as eluent to afford 2 as white powder (1.5 gm, 68%).

ESIMS: 651 [M$^+$+1]

Step 2

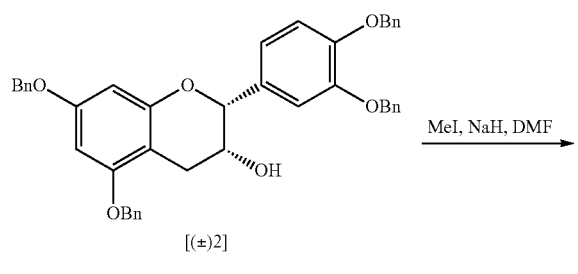

[(±)2]

[(±)3]

To a stirred solution of 2 (0.2 gm, 0 3 mmol) in DMF, NaH was added portion wise (0.025 gm, 0.6 mmol) at 0° C. under nitrogen atmosphere. After 1 hr stirring at this temperature, methyl iodide (0.03 ml, 0.45 mmol) was added and reaction temperature was allowed to increase to 25° C. followed by overnight stirring. Consumption of 2 was monitored by TLC. After complete consumption of 2, water (50 ml) was added and organic layer was extracted with ethyl acetate (2×100 ml). The organic layer was concentrated to afford light brown sticky material 3 (0.18 gm, 90%), which was used as such for further without purification.

ESIMS: 665 [M$^+$+1]

Step 3

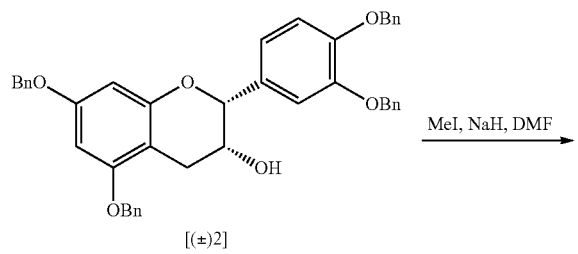

[(±)2]

[(±)3]

To a stirred solution of 2 (0.2 gm, 0.3 mmol) in DMF, NaH was added portion wise (0.025 gm, 0.6 mmol) at 0° C. under nitrogen atmosphere. After 1 hr stirring at this temperature, methyl iodide (0.03 ml, 0.45 mmol) was added and reaction temperature was allowed to increase to 25° C. followed by overnight stirring. Consumption of 2 was monitored by TLC. After complete consumption of 2, water (50 ml) was added and organic layer was extracted with ethyl acetate (2×100 ml). The organic layer was concentrated to afford light brown sticky material 3 (0.18 gm, 90%), which was used as such for further without purification.

ESIMS: 665 [M$^+$+1]

Step 4

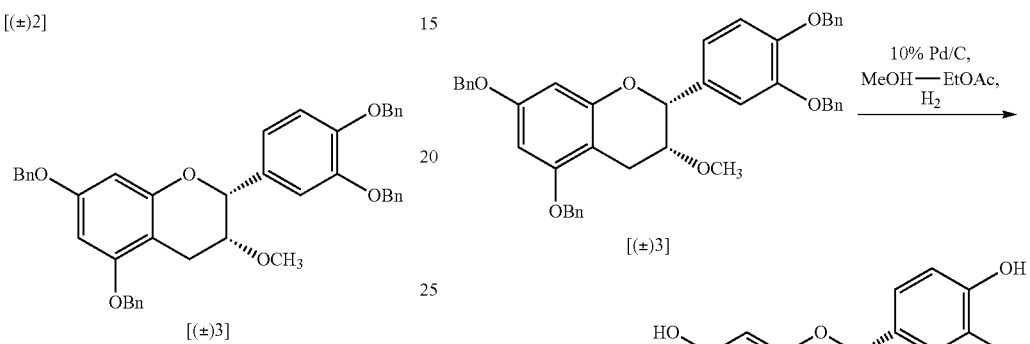

[(±)3]

To a stirred solution of 3 (0.18 g, 0.27 mmol) in a mixture of ethyl acetate and methanol (1;1, 5 ml), was added a slurry of 10% Pd/C (0.02 g) at room temperature. The reaction mixture was stirred for 1 hr at RT, followed by additional stirring of overnight at 50° C.-55° C. Reaction was monitored using TLC. The reaction mass was filtered over celite and excess of solvent was removed under vacuum to afford light brown sticky material, which was further purified using silica gel column and 4% methanol in dichloromethane as eluent to afford (2R,3R)-2-(3,4-dihydroxyphenyl)-3-methoxychroman-5,7-diol as off white sticky material (0.03 gm, 41%).

ESIMS: 305 [M$^+$+1]

EXAMPLE 15

((2R,3R)-2-(3,4-dihydroxyphenyl)-3-ethoxychroman-5,7-diol

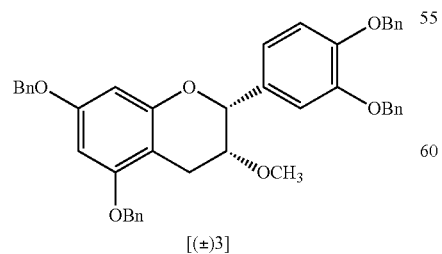

The compound of Example 15 was synthesized according to the procedure of Example 14.

EXAMPLE 16

(2R,3R)-2-(3,4-dihydroxyphenyl)-5,7-dihydroxy-chroman-3-yl acetate

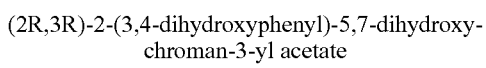

Step 1

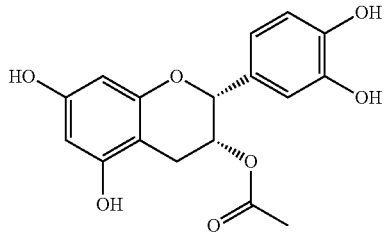

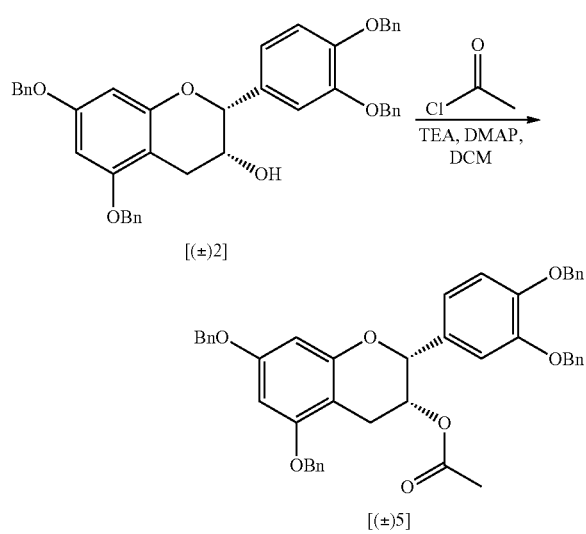

To a stirred solution of 2 (0.15 gm, 0.23 mmol) in dry DCM, TEA (0.05 ml, 0.34 mmol) was added drop wise at 0° C. under nitrogen atmosphere. Stirring was continued for 15 minutes and acetyl chloride (0.02 ml, 0.34 mmol) was added drop-wise followed by the addition of a crystal of DMAP. The reaction temperature was allowed to increase upto 25° C. and stirring was continued for overnight. After complete consumption of 2, saturated NaHCO$_3$ (25 ml) was added and organic layer was extracted with ethyl acetate (2×50 ml). The combined organic layers were washed with water, brine and dried over sodium sulphate. The organic layer was concentrated to afford light brown sticky product 5 (0.11 gm, 82%), which was used further without any purification.

ESIMS: 693 [M$^+$+1]

Step 2

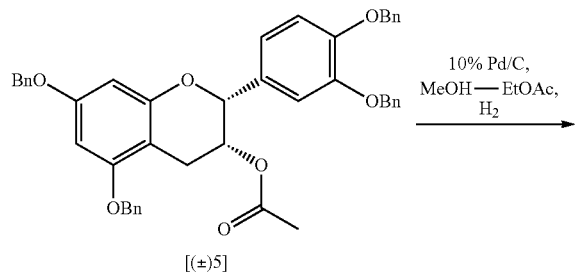

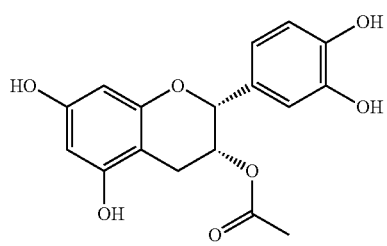 [SMILES: CC(=O)O[C@@H]1Cc2c(O)cc(O)cc2O[C@@H]1c1ccc(O)c(O)c1]

To a stirred solution of 5 (0.11 g, 0.15 mmol) in a mixture of ethyl acetate and methanol (1;1, 5 ml), was added a slurry of 10% Pd/C (0.02 g) at room temperature. The reaction mixture was stirred for 1 hr at RT, followed by additional stirring of overnight at 50° C.-55° C. Reaction was monitored using TLC. The reaction mass was filtered over celite and excess of solvent was removed under vacuum to afford light brown sticky material, which was further purified using silica gel column and 4% methanol in dichloromethane as eluent to afford (2R,3R)-2-(3,4-dihydroxyphenyl)-5,7-dihydroxy-chroman-3-yl acetate as off white sticky material (0.012 gm, 25%).

ESIMS: 333 [M$^+$+1]

EXAMPLE 17

1-(((2R,3R)-2-(3,4-dihydroxyphenyl)-5,7-dihydroxy-chroman-3-yl)oxy)ethyl isobutyrate

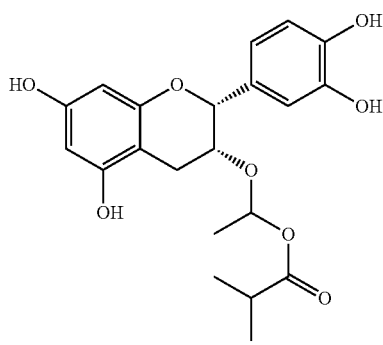 [SMILES: CC(OC(=O)C(C)C)O[C@@H]1Cc2c(O)cc(O)cc2O[C@@H]1c1ccc(O)c(O)c1]

Step 1

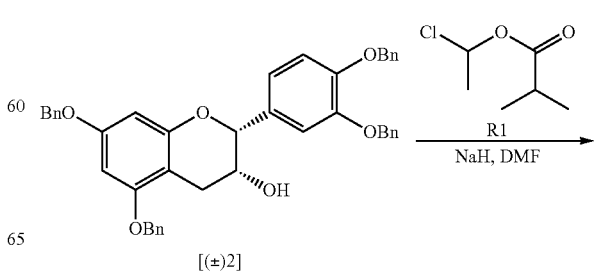

-continued

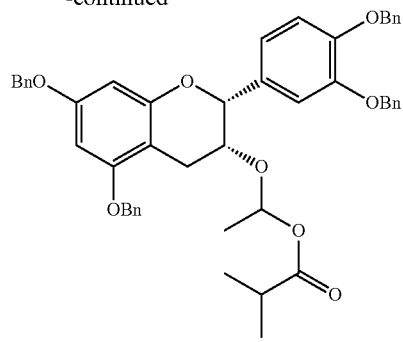

[(±)6]

To a stirred solution of 2 (0.15 gm, 0.23 mmol) in DMF, NaH (0.01 gm, 0.35 mmol) was added portion wise at 0° C. under nitrogen atmosphere. After an additional stirring of 1 h at 0° C., reagent (R1) (0.07 gm, 0.46 mmol) was added portion-wise. The reaction temperature was allowed to increase upto 25° C. and stirring was continued for overnight. After complete consumption of 2, water (25 ml) was added and organic layer was extracted with ethyl acetate (2×100 ml). The combined organic layers were washed with water, brine and dried over sodium sulphate. The organic layer was concentrated to afford light brown sticky material which was further purified using silica gel column chromatography using 5% ethyl acetate in hexane as eluent to afford 6 (0.06 gm, 37%) as white sticky material.

ESIMS: 765 [M$^+$+1]

Step 2

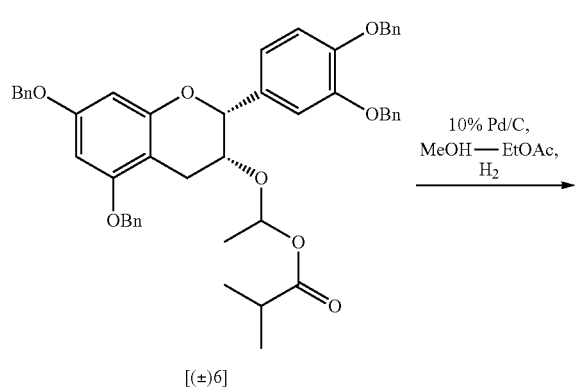

[(±)6]

To a stirred solution of 6 (0.06 g, 0.09 mmol) in a mixture of ethyl acetate and methanol (1;1, 5 ml), was added a slurry of 10% Pd/C (0.01 g) at room temperature. The reaction mixture was stirred for 1 hr at RT, followed by additional stirring of overnight at 50° C.-55° C. Reaction was monitored using TLC. The reaction mass was filtered over celite and excess of solvent was removed under vacuum to afford light brown sticky material, which was further purified using silica gel column and 3% methanol in dichloromethane as eluent to afford 1-(((2R,3R)-2-(3,4-dihydroxyphenyl)-5,7-dihydroxy-chroman-3-yl)oxy)ethyl isobutyrate as off white solid powder (0.02 gm, 47%).

ESIMS: 405 [M$^+$+1]

EXAMPLE 18

(((2R,3R)-2-(3,4-dihydroxyphenyl)-5,7-dihydroxy-chroman-3-yl)oxy)methyl diisopropylcarbamate

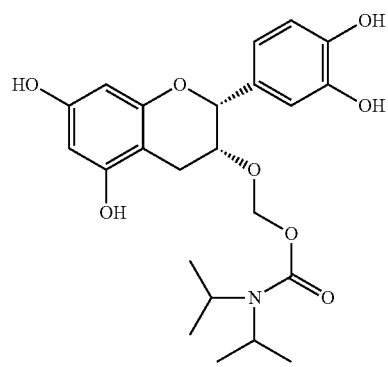 [SMILES: CC(C)N(C(=O)OCO[C@@H]1Cc2c(O)cc(O)cc2O[C@@H]1c1ccc(O)c(O)c1)C(C)C]

The compound of Example 18 was synthesized according to the procedure of Example 17.

EXAMPLE 19 tert-butyl ((((2R,3R)-2-(3,4-dihydroxyphenyl)-5,7-dihydroxychroman-3-yl)oxy)methyl)carbonate

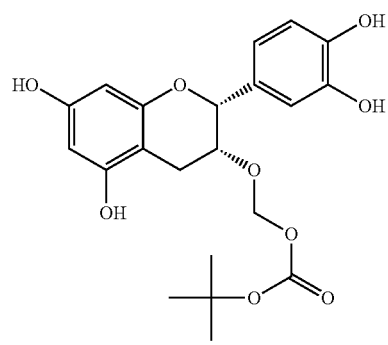 [SMILES: CC(C)(C)OC(=O)OCO[C@@H]1Cc2c(O)cc(O)cc2O[C@@H]1c1ccc(O)c(O)c1]

The compound of Example 19 was synthesized according to the procedure of Example 17.

EXAMPLE 20

4-((2R,3R)-3,5,7-trihydroxychroman-2-yl)-1,2-phenylene dioctanoate

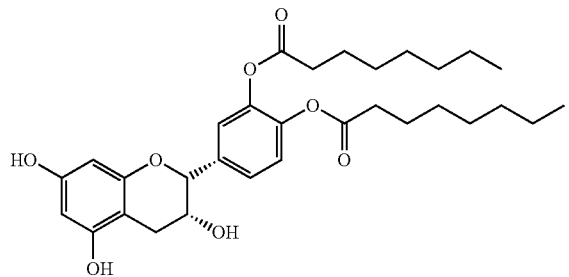

Step 1

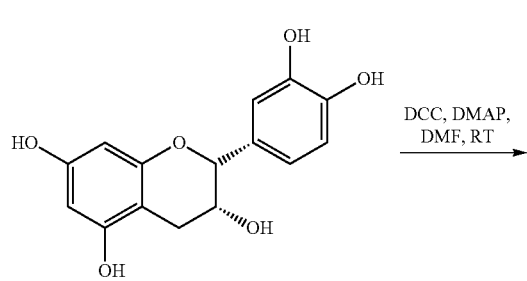

To a stirred solution of (±)1 (100.0 mg, 0.34 mmol) in DMF at room temperature was added DCC (0.106 gm, 0.51 mmol) and DMAP (0.012 mg, 0.10 mmol) followed by dropwise addition of caprylic acid as a DMF solution (0.065 ml, 0.41 mmol). The stirring was continued overnight before addition of water followed by extraction with ethyl acetate (2×50 ml). The combined organic layer was washed with brine and dried over sodium sulphate. The crude reaction mixture was purified using silca gel column and 3% MeOH in DCM as eluent to afford 4-((2R,3R)-3,5,7-trihydroxychroman-2-yl)-1,2-phenylene dioctanoate (0.025 gm, 13%) as a colorless sticky material.

ESIMS: 543 [M$^+$+1]

EXAMPLE 21

(2R,3R)-2-(3,4-dihydroxyphenyl)-5,7-dihydroxychroman-3-yl octanoate

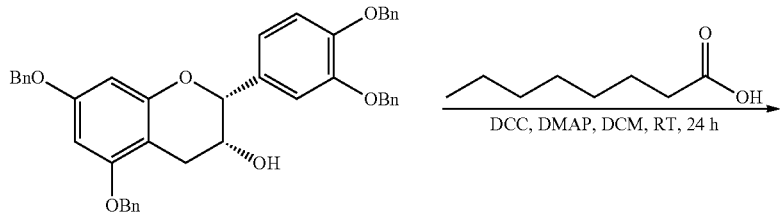

Step 1

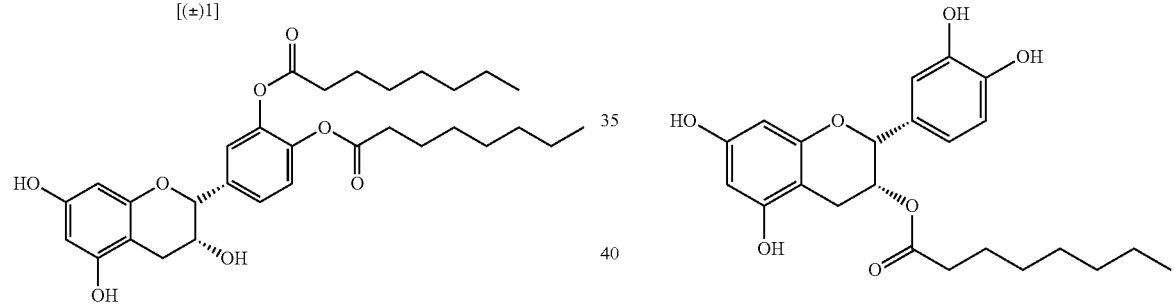

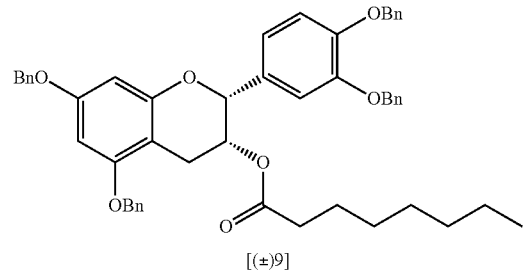

To a stirred solution of 2 (0.20 gm, 0.3 mmol) in DCM, DCC (0.14 gm, 0.67 mmol) and DMAP (0.01 mg, 0.10 mmol) was added at room temperature. After an additional stirring for 10 min, caprylic acid (0.18 ml, 0.67 mmol) was added as a DCM solution. The stirring was continued overnight before addition of water followed by extraction with ethyl acetate (2×50 ml). The combined organic layer was washed with brine and dried over sodium sulphate. The crude reaction mixture was purified using silica gel column and 10% EtOAC in hexane as eluent to afford 9 (0.01 gm, 60%) as a colorless sticky material.

ESIMS: 777 [M$^+$+1]

Step 2

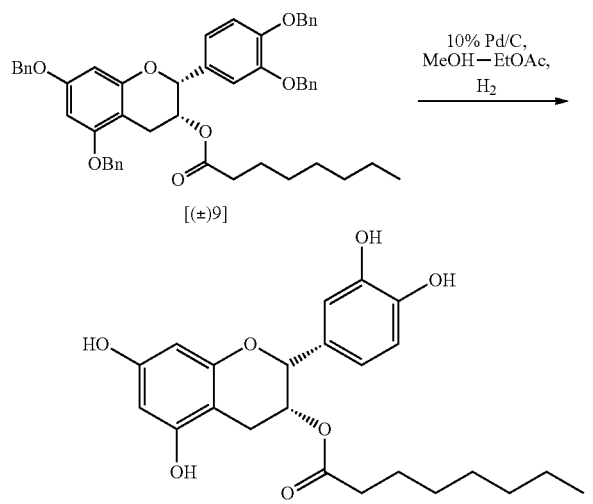

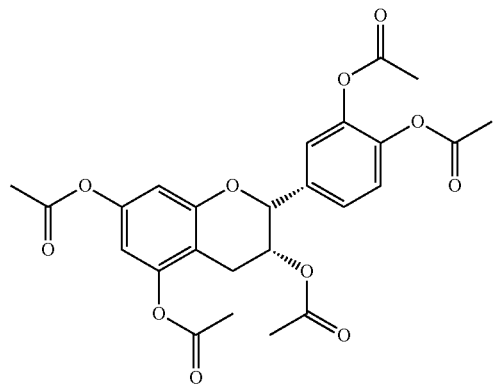

To a stirred solution of 9 (0.09 g, 0.01 mmol) in a mixture of ethyl acetate and methanol (1;1, 5 ml), was added a slurry of 10% Pd/C (0.02 g) at room temperature. The reaction mixture was stirred for 1 hr at RT, followed by additional stirring of overnight at 50° C.-55° C. Reaction was monitored using TLC. The reaction mass was filtered over celite and excess of solvent was removed under vacuum to afford light brown sticky material, which was further purified using silica gel column using 4% methanol in dichloromethane as eluent to afford (2R,3R)-2-(3,4-dihydroxyphenyl)-5,7-dihydroxychroman-3-yl octanoate as off white sticky material (0.02 gm, 53%).

ESIMS: 417 [M$^+$+1]

EXAMPLE 22

(2R,3R)-2-(3,4-diacetoxyphenyl)chroman-3,5,7-triyl triacetate

Step 1

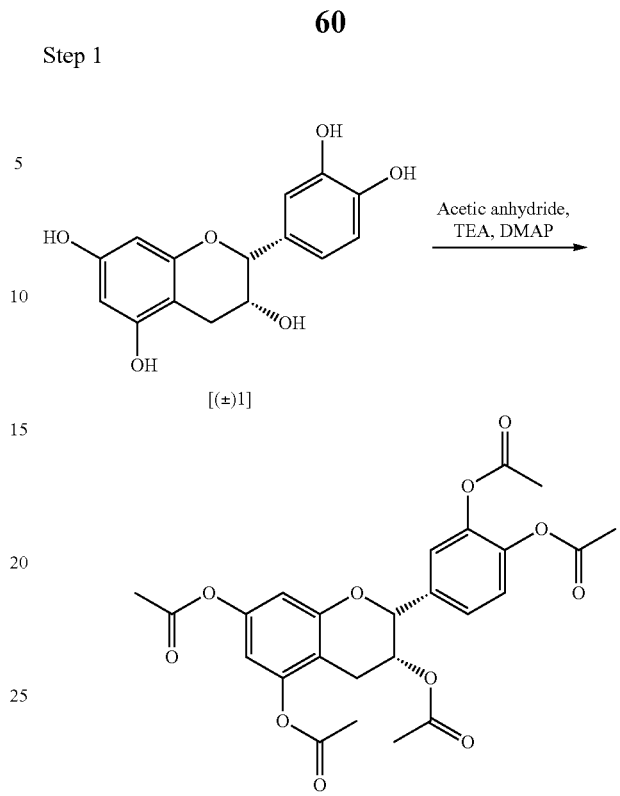

To a stirred solution of (±)epicatechin 1 (0.050 mg, 0.17 mmol) in dry DCM at room temperature, TEA (0.104 ml, 1.34 mmol) and acetic anhydride (0.098 ml, 1.34 mmol) was added. After an additional stirring for 10 min, catalytic amount of DMAP was also added. The reaction mixture was stirred at this temperature for 5-6h. Consumption of 1 was monitored by TLC. After complete consumption of 1, water (25 ml) was added and organic layer was extracted with DCM (2×100 ml). The combined organic layer was washed with brine and dried over sodium sulphate. The crude reaction mixture was further purified using silica gel column using 10% EtOAC in hexane as eluent to afford (2R,3R)-2-(3,4-diacetoxyphenyl)chroman-3,5,7-triyl triacetate as a off white solid powder (0.04 mg, 46%).

ESIMS: 501 [M$^+$+1]

EXAMPLES 23-24

4-((2R,3R)-3,5,7-trihydroxychroman-2-yl)-1,2-phenylene diacetate (Example 23)

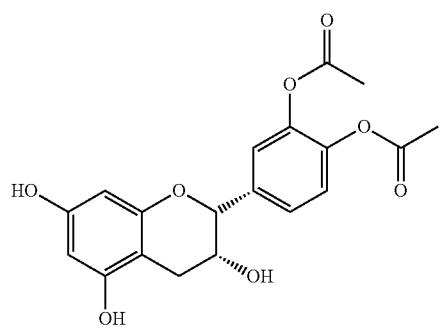

and 4-((2R,3R)-3,5,7-trihydroxychroman-2-yl)-1,2-phenylene diacetate (Example 24)

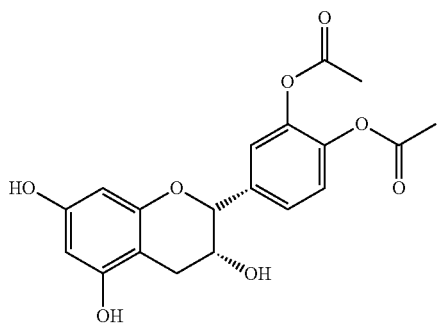

Step 1

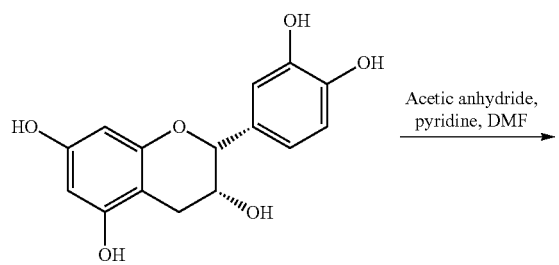

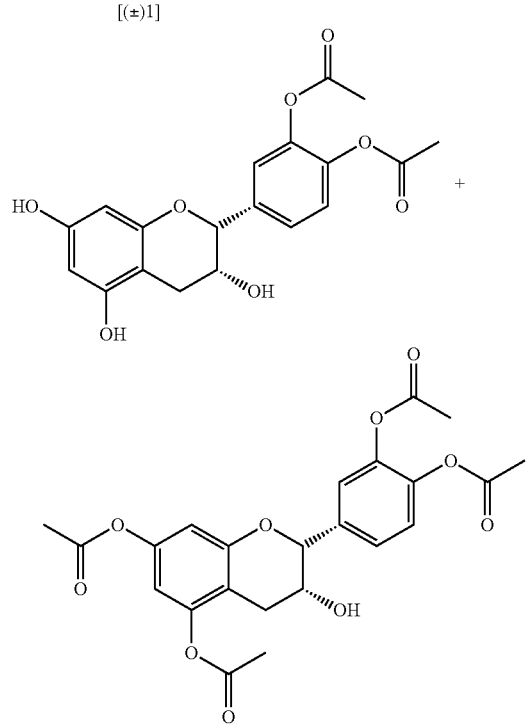

To a stirred solution of (±) epicatechin 1 (0.10 gm, 0.34 mmol) in DMF, Acetic anhydride (0.11 ml, 0.10 mmol) and pyridine (0.08 ml, 0.10 mmol) was added at room temperature. After an additional stirring at this for 24 h, 2N HCl was added and extracted with ethyl acetate (2×50 ml). The combined organic layer was washed with brine and dried over sodium sulphate. The crude reaction mixture was purified using preparative HPLC to afford 4-((2R,3R)-3,5,7-trihydroxychroman-2-yl)-1,2-phenylene diacetate (0.004 gm) and 4-((2R,3R)-3,5,7-trihydroxychroman-2-yl)-1,2-phenylene diacetate (0.008 gm) as a white solid material.

ESIMS: 375 [M$^+$+1] 4-((2R,3R)-3,5,7-trihydroxychroman-2-yl)-1,2-phenylene diacetate.

ESIMS: 459 [M$^+$+1] 4-((2R,3R)-3,5,7-trihydroxychroman-2-yl)-1,2-phenylene diacetate

EXAMPLE 25

(2R,3R)-2-(3,4-dihydroxyphenyl)-3-methylchroman-3,5,7-triol

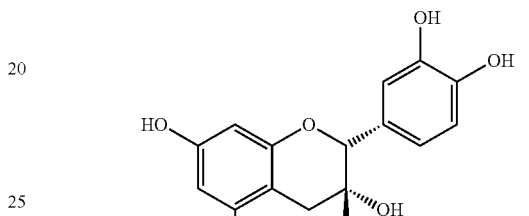

Step 1

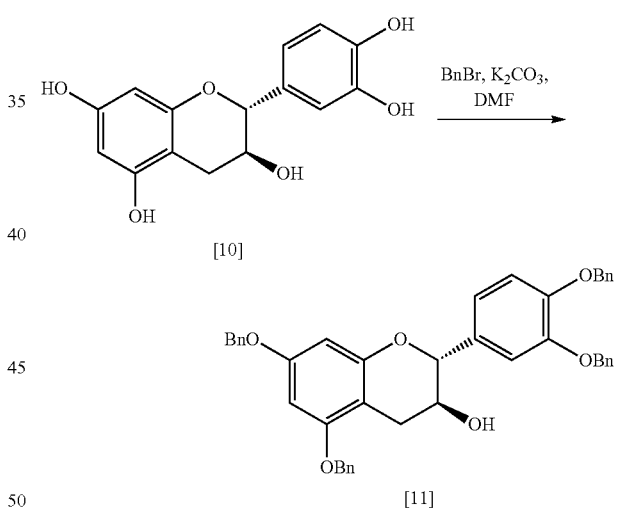

To a stirred solution of 10 (1.0 gm, 3.4 mmol) in DMF, anhydrous K$_2$CO$_3$ (2.3 gm, 17.0 mmol) was added at 0° C. under nitrogen atmosphere. After an additional stirring at this for 15 minutes at same temperature, benzyl bromide (2.0 ml, 17.0 mmol) was added drop-wise. The reaction temperature was allowed to increase upto 25° C. and stiffing was continued for overnight. Consumption of 10 was monitored by TLC. After complete consumption of 10, water (50 ml) was added and organic layer was extracted with ethyl acetate (3×100 ml). The combined organic layers were washed with water, brine and dried over sodium sulphate. The organic layer was concentrated to afford light brown sticky material which was further purified using silica gel column chromatography using 8% ethyl acetate in hexane as eluent to afford 11 as white powder (1.5 gm, 68%).

ESIMS: 651 [M$^+$+1]

Step 2

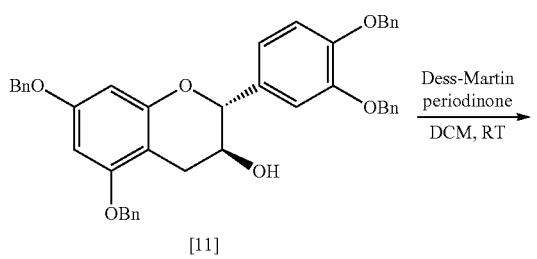

To a stirred solution of (+) 11 (1.0 gm, 1.53 mmol) in Dry DCM, Dess-Martin Peridinone (0.98 gm, 2.3 mmol) was added in one portion at room temperature. After an additional stirring for 6-7h, saturated NaHCO3 (20 ml) was added and was extracted with DCM (3×100 ml). The combined organic layers were washed with water and dried over sodium sulphate. The organic layer was concentrated to afford light pink sticky material which was further purified using silica gel flash column chromatography using DCM as eluent to afford off 12 as a white-pinkish solid powder (0.65 gm, 71%)

ESIMS: 649 [M$^+$+1]

Step 3

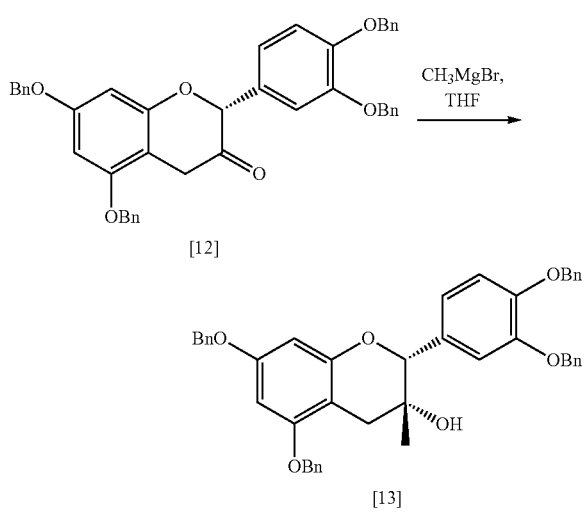

To a stirred solution of 12 (0.20 gm, 0.30 mmol) in dry THF, Methyl magnesium bromide (0.25 ml, 0.61 mmol) was added drop wise at 0° C. under nitrogen atmosphere. After an additional stirring for 3 h at same temperature, the reaction temperature was allowed to increase upto 25° C. and stirring was continued for overnight. Consumption of 12 was monitored by TLC. After complete consumption of 12, saturated NaHCO$_3$ (10 ml) was added and organic layer was extracted with ethyl acetate (2×50 ml). The combined organic layers were washed with water, brine and dried over sodium sulphate. The organic layer was concentrated to afford light brown sticky material. This crude product (+) 13 (0.12 gm, 58%) was used as such for further steps.

ESIMS: 665 [M$^+$+1]

Step 4

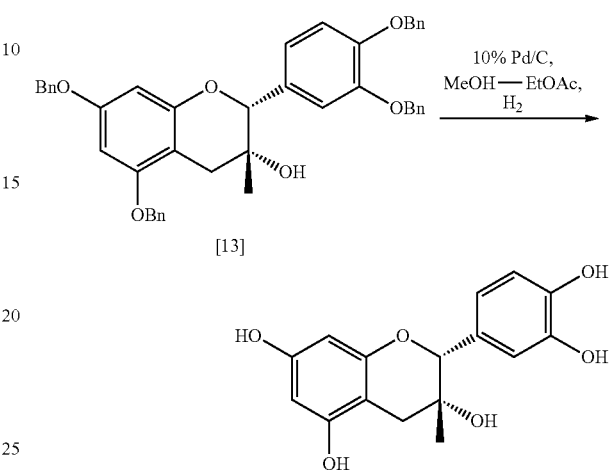

To a stirred solution of (+) 13 (0.10 g, 0.15 mmol) in a mixture of ethyl acetate and methanol (1;1, 5 ml), was added a slurry of 10% Pd/C (0.01 g) at room temperature. The reaction mixture was stirred for 1 hr at RT, followed by additional stirring of overnight at 50° C.-55° C. Reaction was monitored using TLC. The reaction mass was filtered over celite and excess of solvent was removed under vacuum to afford light brown sticky material, which was further purified using silica gel column using 6% methanol in dichloromethane as eluent to afford (2R,3R)-2-(3,4-dihydroxyphenyl)-3-methylchroman-3,5,7-triol as off white sticky material (0.03 gm, 66%).

ESIMS: 305 [M$^+$+1]

EXAMPLE 26

The effect of (−)-epicatechin analogs on mitochondrial complex proteins (MCP) I and V was studied human (HCAEC) or bovine (BCAEC) Coronary Artery Endothelial cells. Western blots were performed as follows: Approximately 50 mg of cells were homogenized with a polytron in 500 µl lysis buffer (1% triton X-100, 20 mM Tris, 140 mM NaCl, 2 mM EDTA, and 0.1% SDS) with protease and phosphatase inhibitor cocktails (P2714 and P2850, Sigma-Aldrich, St. Louis, Mo.) supplemented with 0.15 mM PMSF, 5 mM Na3VO4 and 3 mM NaF. Homogenates were passed through an insulin syringe five times, sonicated for 30 min at 4° C. and centrifuged (12,000 g) for 10 min. The total protein content was measured in the supernatant using the Bradford method. A total of 40 µg of protein was loaded onto a 4%-15% precast TGX polyacrylamide gel (Bio-rad), electrotransferred (12 V, 50 minutes), incubated for 1 h in blocking solution (5% nonfat dry milk in TBS plus 0.1% Tween 20 [TBS-T]). Blots were probed with a cocktail of monoclonal antibodies to electron transport chain proteins (OXPHOS) (20 KDa subunit of complex I, 26 KDa subunit of complex IV, subunit core 2 of complex III, 30 Kda complex II and ATP synthase 54 Kda complex V). MitoProfile (Total OXPHOS from MitoSciences), Porin (Cell Signaling), and mitofilin (Cell Signaling) primary antibodies were diluted 1:1000 and GAPDH (rabbit polyclonal, Cell Signaling) primary antibody was diluted 1:2000 in TBS-T plus 5% nonfat dry milk. Membranes were washed (3× for 5 min) in TBS-T and incubated 1 h at room temperature in the presence of HRP-conjugated secondary antibodies (Cell Signaling) diluted 1:10,000 in blocking solution. Membranes were again washed 3 times in TBS-T, and the immunoblots were developed using an ECL Plus detection kit (Amersham-GE). The band intensities were digitally quantified using ImageJ software (http://www.nih.gov).

Figure 2:
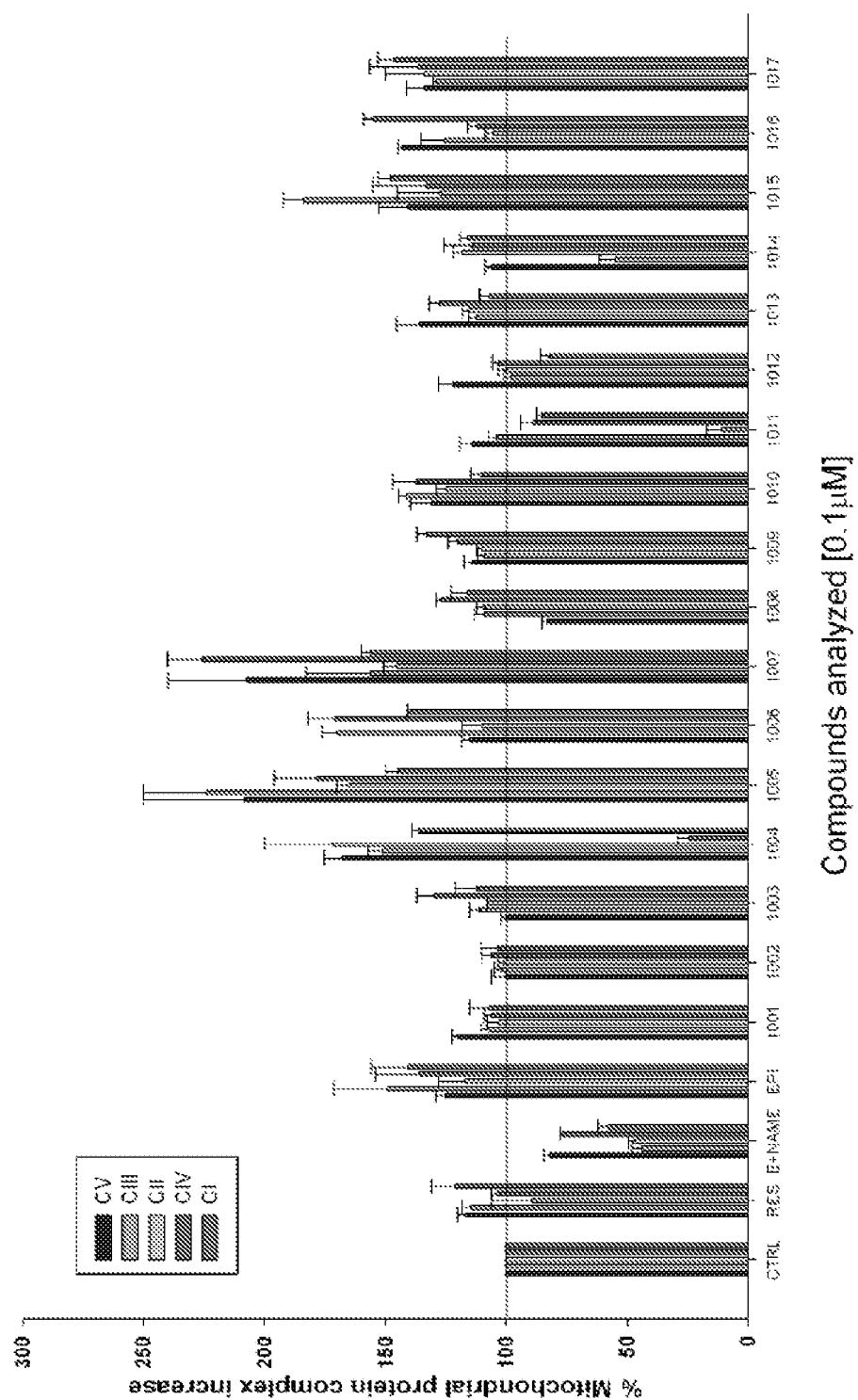
FIG. 2 depicts the results of the assays disclosed herein.

FIG. 1 depicts the structures of some epicatechin derivatives tested, and FIG. 2 depicts the results in graphical form. Monosubstitution on the B-ring hydroxyls with small alkyl groups generally resulted in an increase in MCP equal to or greater than that seen for (−)-epicatechin. The methyl, ethyl, and propyl analogs all showed a significant increase in effect relative to (−)-epicatechin. Ethyl 2-acetyl derivatives also showed a significant increase in effect at complex I but a reduction of effect at complex V relative to (−)-epicatechin. The trifluoropropyl, 3-methyl-2-butenyl, and benzyl all lost activity relative to (−)-epicatechin. Replacement of either of the B-ring hydroxyls with carboxymethyl resulted in compounds which showed a moderate increase in effect at complex I relative to (−)-epicatechin. Hydrolysis to the corresponding acids, amidation with methyl piperidine or reduction to the corresponding hydroxymethyl derivatives generally resulted in reduced activity relative to (−)-epicatechin. Substitution on the C-ring hydroxyl by propyl resulted in a particularly high response at both complex I and V. However, alkylation with S-glycidyl chloride provided a derivative which showed a dramatic loss of potency. Oxidation of the C-ring hydroxyl to the 3-keto compound resulted in a loss in potency. Reductive amination of the 3-keto compound with benzyl amine provided two diastereomers both of which also showed a loss in potency. Substitution of the A-ring generated compounds which were universally less potent than (−)-epicatechin unless there were also potency-enhancing substitutions on the other rings. The 8-position, on the A-ring, was substituted with a diverse set of functional groups with respect to sterics, electronics, polarity and charge. The 5,7-dimethyl substituted (−)-epicatechin was less potent than the unsubstituted parent, but further alkylation at the 3' or 4' position to give the trimethylated derivatives improved potency to slightly better than the parent (−)-epicatechin. Further substitution with benzyl, on the remaining phenolic hydroxyl, of the trimethylated derivatives had little effect.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A compound selected from the group consisting of:
   i. 2-(4-Hydroxy-3-propoxy-phenyl)-chroman-3,5,7-triol;
   ii. 2-(3-Hydroxy-4-propoxy-phenyl)-chroman-3,5,7-triol;
   iii. 2-(3-ethoxy-4-Hydroxy-phenyl)-chroman-3,5,7-triol;
   iv. 2-(4-ethoxy-3-Hydroxy-phenyl)-chroman-3,5,7-triol;
   v. 2-(3,4-Dihydroxy-phenyl)-3-propoxy-chroman-5,7-diol;
   vi. methyl 4-((2R,3R)-3-hydroxy-5,7-dimethoxychroman-2-yl)-2-methoxybenzoate;
   vii. methyl 5-((2R,3R)-3-hydroxy-5,7-dimethoxychroman-2-yl)-2-methoxybenzoate;
   viii. (4-((2R,3R)-3-hydroxy-5,7-dimethoxychroman-2-yl)-2-methoxyphenyl)(4-methylpiperazin-1-yl)methanone;
   ix. ethyl 2-(4-((2R,3R)-3-hydroxy-5,7-dimethoxychroman-2-yl)-2-methoxyphenoxy)acetate;
   x. ethyl 2-(5-((2R,3R)-3-hydroxy-5,7-dimethoxychroman-2-yl)-2-methoxyphenoxy)acetate;
   xi. 2-(4-((2R,3R)-3-hydroxy-5,7-dimethoxychroman-2-yl)-2-methoxyphenoxy) acetic acid;
   xii. ethyl 2-(2-hydroxy-4-((2R,3R)-3,5,7-dimethoxychroman-2-yl)phenoxy)acetate;
   xiii. ethyl 2-(2-hydroxy-5-((2R,3R)-3,5,7-dimethoxychroman-2-yl)phenoxy)acetate;
   xiv. (2R,3R)-2-(3,4-dihydroxyphenyl)-3-methoxychroman-5,7-diol;
   xv. (2R,3R)-2-(3,4-dihydroxyphenyl)-5,7-dihydroxychroman-3-yl acetate;
   xvi. 1-(((2R,3R)-2-(3,4-dihydroxyphenyl)-5,7-dihydroxychroman-3-yl)oxy)ethyl isobutyrate;
   xvii. (((2R,3R)-2-(3,4-dihydroxyphenyl)-5,7-dihydroxychroman-3-yl)oxy)methyl diisopropylcarbamate;
   xviii. tert-butyl (((((2R,3R)-2-(3,4-dihydroxyphenyl)-5,7-dihydroxychroman-3-yl)oxy)methyl)carbonate;
   xix. 4-((2R,3R)-3,5,7-trihydroxychroman-2-yl)-1,2-phenylene dioctanoate;
   xx. (2R,3R)-2-(3,4-dihydroxyphenyl)-5,7-dihydroxychroman-3-yl octanoate;
   xxi. (2R,3R)-2-(3,4-diacetoxyphenyl)chroman-3,5,7-triyl triacetate;
   xxii. 4-((2R,3R)-3,5,7-trihydroxychroman-2-yl)-1 phenylene diacetate;
   xxiii. 4-((2R,3R)-3,5,7-trihydroxychroman-2-yl)-1,2-phenylene diacetate;
   xxiv. (2R,3R)-2-(3,4-dihydroxyphenyl)-3-methylchroman-3,5,7-triol; and
   xxv. a racemic mixture or a pharmaceutically acceptable salt thereof of any of (i) to (xxiv).

2. A compound selected from the group consisting of:
   (i) 1-(((2R,3R)-2-(3,4-dihydroxyphenyl)-5,7-dihydroxychroman-3-yl)oxy)ethyl isobutyrate
   (ii) (((2R,3R)-2-(3,4-dihydroxyphenyl)-5,7-dihydroxychroman-3-yl)oxy)methyl diisopropylcarbamate; and
   (iii) tert-butyl (((((2R,3R)-2-(3,4-dihydroxyphenyl)-5,7-dihydroxychroman-3-yl)oxy)methyl)carbonate.

3. A compound selected from the group consisting of:
   (i) 4-((2R,3R)-3-hydroxy-5,7-dimethoxychroman-2-yl)-2- methoxybenzoic acid
   (ii) Ethyl 2-(2-hydroxy-4-((2R,3R)-3,5,7-trihydroxychroman-2-yl)phenoxy)acetate
   (iii) Ethyl 2-(2-hydroxy-5-((2R,3R)-3,5,7-trihydroxychroman-2-yl)phenoxy)acetate
   (iv) Ethyl 2-(4-((2R,3R)-3-hydroxy-5,7-dimethoxychroman-2-yl)-2-methoxyphenoxy)acetate
   (v) 2-(4-((2R,3R)-3-hydroxy-5,7-dimethoxychroman-2-yl)-2-methoxyphenoxy)acetic acid
   (vi) 4-((2R,3R)-3,5,7-trihydroxychroman-2-yl)1,2-phenylene dioctanoate.

* * * * *